US006291743B2

(12) United States Patent
Stout et al.

(10) Patent No.: US 6,291,743 B2
(45) Date of Patent: *Sep. 18, 2001

(54) TRANSGENIC PLANTS EXPRESSING MUTANT GEMINIVIRUS AC1 OR C1 GENES

(75) Inventors: John T. Stout, Kalamazoo, MI (US); Hang T. Luu, Baltimore, MD (US); Steven F. Hanson, Madison, WI (US); Douglas P. Maxwell, Verona, WI (US); Paul G. Ahlquist, Madison, WI (US); Robert L. Gilbertson, Davis, CA (US)

(73) Assignees: Seminis Vegetable Seeds, Inc., Oxnard, CA (US); Wisconsin Alymni Research Foundation, Madison, WI (US); Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/838,151

(22) Filed: Apr. 15, 1997

Related U.S. Application Data

(60) Provisional application No. 60/015,517, filed on Apr. 16, 1996.

(51) Int. Cl.$^7$ .................................................. A01H 5/00

(52) U.S. Cl. .............................................................. 800/301

(58) Field of Search ...................... 536/23.72; 435/320.1, 435/419, 468, 69.1, 440; 800/280, 279, 301

(56) References Cited

U.S. PATENT DOCUMENTS 5,850,023 * 12/1998 Elmer et al. .......................... 800/205

FOREIGN PATENT DOCUMENTS

WO 96/08573    3/1996  (WO) .

OTHER PUBLICATIONS

Kunkel et al., "Rapid and Efficient Site–Specific Mutagenesis without Phenotypic Selection", *Recombinant DNA Methodology*, 1989, pp. 587–601.
Gilbertson et al., "Differentiation of Bean–Infecting Geminiviruses by Nucleic Acid Hybridization Probes and Aspects of Bean Golden Mosaic in Brazil", *Plant Disease*, vol. 75, No. 4, 1991, pp. 336–342.
Gilbertson et al., "Pseudorecombination between infectious cloned DNA components of tomato mottle and bean dwarf mosaic geminiviruses", *Journal of General Virology*, vol. 74, 1993, pp. 23–31.
Navot et al., "Tomato Yellow Leaf Curl Virus: A Whitefly–Transmitted Geminivirus with a Single Genomic Component", *Virology*, vol. 185, 1991, pp. 151–161.

Faria et al., "Bean Golden Mosaic Geminivirus Type II Isolates from the Dominican Republic and Guatemala: Nucleotide Sequences, Infectious Pseudorecombinants, and Phylogenetic Relationships", *The American Phytopathological Society*, vol. 84, No. 3, 1994, pp. 321–329.
Torres–Pacheco et al., "Complete nucleotide sequence of pepper huasteco virus: analysis and comparison with bipartite geminivirus", *Journal of General Virology*, vol. 74, 1993, pp. 2225–2231.
Kunik et al., "Transgenic Tomato Plants Expressing the Tomato Yellow Leaf Curl Virus Capsid Protein are Resistant to the Virus", *Bio/Technology*, vol. 12, May 1994, pp. 500–504.
Hanson et al., "Mutational Analysis of a Putative NTP–Binding Domain the the Replication–Associated Protein (AC1) of Bean Golden Mosaic Geminivirus", *Virology*, vol. 211, 1995, pp. 1–9.
Noris et al., "Resistance to Tomato Yellow Leaf Curl Geminivirus in *Nicotiana benthamiana* Plants Transformed with a Truncated Viral C1 Gene", *Virology*, vol. 224, 1996, pp. 130–138.
Bendahmane et al. "Engineering resistance against tomato yellow leaf curl virus (TYLCV) using antisense RNA", *Plant Molecular Biology*, vol. 33, 1997, pp. 351–357.
Blokland et al., "Transgene–mediated Suppression of Chalcone Synthase Expression in *Petunia hybrida* results from an Increase in RNA Turnover", *The Plant Journal*, vol. 6(6), 1994, pp. 861–877.
Lazarowitz, "Geminivirus: Genome Structure and Gene Function", *Critical Reviews in Plant Science*, vol. 4(11), 1992, pp. 327–349.
Kouchkovsky et al., "Molecular Biology of Tomato Yellow Leaf Curl Virus (TYLCV) and Potential Ways to Control the Disease", Chapter 22, pp. 227–237, Molecular Biology of the Tomato: Fundamental Advances and Crop Improvement, 1993.
CA Abstract 125:27658 (Abstract of WO 96/08573), Mar. 21, 1996.*
Hanson, S.F. et al., Phytopathy, from the Annual Meeting of the American Phytopathological Society Conference, St. Louis, Missouri, 81(10):1247, (1991).
Nakhla et al., *Plant Disease*, 76(5):538, (1992).
EMBL Acc No. M90495, (Oct. 14, 1993).
EMBL Acc No. L02618, (Mar. 17, 1993).
EMBL Acc No. M90494, (Oct. 4, 1993).

(List continued on next page.)

Primary Examiner—Amy J. Nelson
(74) Attorney, Agent, or Firm—Rockey, Milnamow & Katz, Ltd.

(57) ABSTRACT

The invention involves production of transgenic plants containing DNA encoding AC1/C1 wildtype and mutant sequences that negatively interfere in trans with geminiviral replication during infection. The transgenic plants produced by the invention are resistant to viral infection.

5 Claims, 1 Drawing Sheet

OTHER PUBLICATIONS

Kooin, Eugene V. et al., Geminivirus replication proteins are related to prokaryotic plasmid rolling circle DNA replication initiator proteins, *Journal of General Virology*, 73:2763–2766, (1992).

Laufs, J. et al., Geminivirus replication: genetic and biochemical characterization of Rep protein function, a review, *Biochimi*, 77:765–773, (1995).

Timmermans, Marja C., et al., Geminiviruses and Their Uses as Extrachromosomal Replicons, *Annu. Rev. Plant Physiol. Plant Mol. Biol.*, 45:79–112, (1994).

An, Gynheung, Development of Plant Promoter Expression Vectors and Their Use for Analysis of Differential Activity of Nopaline Synthase Promoter in Transformed Tobacco Cells, *Plant Physiol.* 81:86–91, (1986).

Bejarano, Eduardo R., et al., Expression of TGMV antisense RNA in transgenic tobacco inhibits replication of BCTV but not ACMV geminiviruses, *Plant Molecular Biology*, 24:241–248, (1994).

Carr, John P., et al., Resistance in Transgenic Tobacco Plants Expressing a Nonstructural Gene Sequence of Tobacco Mosaic Virus Is a Consequence of Markedly Reduced Virus Replication, *Molecular Plant–Microbe Interactions* 4(6):579–585, (1991).

Chejanovsky, Nor et al., Mutation of a Consensus Purine Nucleotide Binding Site in the Adeno–Associated Virus rep Gene Generates a Dominant Negative Phenotype for DNA Replication, *Journal of Virology*, 64(4):1764–1770, (1990).

Currier, Thomas C. et al., Isolation of Covalently Closed Circular DNA of High Molecular Weight from Bacteria, *Biochemistry*, 76:431–441, (1976).

Day, A.G., et al., Expression of an antisense viral gene in transgenic tobacco confers resistance to the DNA virus tomato golden mosaic virus, *Proc. Natl. Acad. Sci. USA*, 88:6721–6725, (1991).

Editorial, Protection of plants against viral diseases by cloned viral genes and anti–genes, *Gene*, 107:177–179, (1991).

Friedman, Alan D. et al., Expression of a truncated viral trans–activator selectively impedes lytic infection by its cognate virus, *Nature*, 335:452–454, (1988).

Gilbertson, Robert L., et al., Cloning of the Complete DNA Genomes of Four Bean–Infecting Geminiviruses and Determining Their Infectively by Electric Discharge Particle Acceleration, *The American Phytopathological Society*, 81(9):980–985, (1991).

Grierson, D., et al., Fruit ripening and quality, The Tomato Crop: A Scientific Basis For Improvement, Chapman and Hall, pp. 241–280, (1986).

Grierson, D., et al., Sequencing and identification of a cDNA clone for tomato polygalacturonase, *Nucleic Acids Research*, 14(21):8595–8803, (1986).

Hanson, Stephen F., et al., Mutational Analysis of a Putative NTP–Binding Domain in the Replication–Associated Protein (AC1) of Bean Golden Mosaic Geminivirus, *Virology*, 211:1–9, (1995).

Hemerly, Adriana, et al., Dominant negative mutants of the Cdc2 kinase uncouple cell division from iterative plant development, *The EMBO Journal*, 14(16):3925–3936, (1995).

Heyraud–Nitschke, Francoise, et al., Determination of the origin cleavage and joining domain of geminivirus Rep proteins, *Nucleic Acids Research*, 23(6):910–916, (1995).

Hoogstraten, R.A., et al., Mutational Analysis of the Putative Nicking Motif in the Replication–Associated Protein (AC1) of Bean Golden Mosaic Geminivirus, Molecular Plant Microbe Interactions, 9(7):594–599, (1996).

Ilyina, Tatyana V. et al., Conserved sequence motifs in the initiator proteins for rolling circle DNA replication encoded by diverse replicons from eubacteria, eucaryotes and archaebacteria, *Nucleic Acids Research*, 20(13):3279–3285, (1992).

Jupin, Isabelle, et al., DNA replication specificity of TYLCV geminivirus is medicated by the amino–terminal 116 amino acids of the Rep protein, *FEBS Letters*, 362:116–120, (1995).

Laufs, Jurgen, et al., In vitro cleavage and joining at the viral origin of replication by the replication initiator protein of tomato yellow leaf curl virus. *Proc. Natl. Acad. Sci. USA*, 92:3879–3883, (1995).

Li, Xu, et al., Mutation of Lysine 405 to Serine in the Parvovirus H–1 NS1 Abolishes Its Functions for Viral DNA Replication, Late Promoter trans Activation, and Cytotoxicity, *Journal of Virology*, 64(10):4654–4660, (1990).

Longstaff, Marian, et al., Extreme resistance to potato virus X infection in plants expressing a modified component of the putative viral replicase, *The EMBO Journal*, 12(2):379–386, (1993).

Medberry, Scott L., et al., The Commelina Yellow Mottle Virus Promoter Is a Strong Promoter in Vascular and Reproductive Tissues, *The Plant Cell*, 4:185–192, (1992).

Nakhla, M.K., et al., Molecular characterization of four tomato yellow leaf curl virus isolates from Egypt and development of diagnostic methods, *Phytopath, medit*, 32;163–173, (1993).

Ni, Min, et al., Strength and tissue specificity of chimeric promoters derived from the octopine and mannopine synthase genes, *The Plant Journal*, 7(4):661–676, (1995).

Owens, Roland A., et al., Adeno–Associated Virus Rep Proteins Produced in Insect and Mammalian Expression Systems: Wild–Type and Dominant–Negative Mutant Proteins Bind to the Viral Replication Origin, *Virology*, 184:14–22, (1991).

Pietrzak, Maciej, et al., Expression in plants of two bacterial antibiotic resistance genes after protoplast transformation with a new plant expression vector, *Abstract, Nuleic Acids Research*, 14(14):5857–5868, (1986).

Pogson, Barry L., et al., Differential Expression of Two 1–Aminocyclopropane–1–Carboxylic Acid Oxidase Genes in Broccoli after Harvest, *Plant Physiol.* 108:651–657, (1995).

Pogson, Barry L., et al., Nucleotide Sequence of a cDNA Clone Encoding 1–Aminocyclopropane–1–Carboxylic Acid Synthase from Broccoli, *Plant Physiol.* 108:857–858, (1995).

Sanford, J.C., et al., The Concept of Parasite–Derived Resistance–Deriving Resistance Genes from the Parasite's Own Genome, *J. theor. Biol.* 113:395–405, (1985).

Stanley, John, et al., Defective viral DNA ameliorates symptoms of geminivirus infection in transgenic plants, *Proc. Natl. Acad. Sci. USA*, 87:6291–6295, (1990).

Stow, Nigel, D., et al., Inhibition of Herpes Simplex Virus Type 1 DNA Replication by Mutant Forms of the Origin–Binding Protein, *Virology*, 196:413–418, (1993).

Twell, David, et al., Isolation and expression of an anther–specific gene from tomato, *Mol. Gen. Genet*, 217:240–245, (1989).

Twell, David, et al., Pollen–specific gene expression in transgenic plants: coordinate regulation of two different tomato gene promoters during microsporogenesis, *Development,* 109:705–713, (1990).

Unger, Erica, et al., Dominant Negative Mutants of Opaque2 Suppress Transactivation of a 22–kD Zein Promoter by Opaque2 in Maize Endosperm Cells, *The Plant Cell,* 5:831–841, (1993).

Weiner, Beth, et al., Specific Mutation of a Regulatory Site within the ATP–Binding Region of Simian Virus 40 Large T Antigen, *Journal of Virology,* pp. 4973–4984, (1991).

Whitaker–Dowling, Patricia et al., Viral Interference–Dominance of Mutant Viruses over Wild–Type Virus in Mixed Infection, *Microbiological Reviews,* 51(2):179–191, (1987).

Yeung, Michael C. and Lau, Allan S., Fast and Economical Large–Scale Preparation of High–Quality Plasmid DNA, *Biotechnology,* 15(3):149–150, (1993).

Inokuchi, Yoshio, et al., Interference with Viral Infection by Defective RNA Replicase, *Journal of Virology,* 61(12):3946–3949, (1987).

Hanson, S.F., et al., Mutational Analysis of a Putative NTP–Binding Domain of the AC1 ORF of Bean Golden Mosaic Geminivirus, *Amer. Soc. Virology,* 13th Ann. Mtg., Jul. 9–13, 1994, Madison, WI.

Gorbalenyam et al., Viral protein containing the purine NTR–binding sequence pattern, *Nucleic Acid Research,* 17(21):8413–8440, (1989).

Murrilas, R., et al. Expression of a dominant negative mutant of epidermal growth factor receptor in the epidermis of transgenic mice elicits striking alterations in hair follicle development and skin structure, *The EMBO Journal,* 14(21):5216–5223, (1995).

Aono, Mitsuko et al., "Resistance to Active Oxygen Toxicity of Transgenic *Nicotiana tabacum* that Expresses the Gene for Glutathione Reductase from *Escherichia coli*", *Plant Cell Physiol.* 32(5):691–697 (1991).

Hanley–Bowdoin, Linda, et al., "Expression of functional replication protein from tomato golden mosaic virus in transgenic tobacco plants", *Proc. Natl. Acad. Sci USA,* 87:1446–1450 (1990).

Fields Virology, 3rd Editon, vol. 1, Chap. 17, pp. 507–508 (1996).

Gleave, Andrew, P., "A Versatile Binary Vector System With A T–DNA Organisational Structure Conducive To Efficient Integration of Cloned DNA Into The Plant Genome", *Plant Molecular Biology,* 20:1203–1207 (1992).

Nishihara, Masahiro, et al., "Transgenic haploid plants of *Nicotiana rustica* produced by bombardment–mediated transformation of pollen", *Transgenic Research,* 4:341–348 (1995).

Noris, E., et al., "Resistance to Tomato Yellow Leaf Curl Geminivirus in *Nicotiana benthamiana* Plants Transformed with a Truncated Viral C1 Gene" *Virology* 224:130–138 (1996).

Rigden, Justin E., et al., "ORF C4 of Tomato Leaf Curl Geminivirus is a Determinant of Symptom Severity", *Virology,* 204:847–850 (1994).

Schroeder, Hartmut, E., et al., "Expression of a Chicken Ovalbumin Gene in Three Lucerne Cultivars" *Aust. J. Physiol.,* 18:495–505 (1991).

Sawasaki, Tatsuya, et al., "Stable transformation of *Arabidopsis* with the bar gene using particle bombardment", *Transgenic Research* 3:279–286 (1994).

Stanley, John, et al., A Symptom Variant of Beef Curly Top Geminivirus Produced by Mutation of Open Reading Frame C4, *Virology* 190:506–509 (1992).

\* cited by examiner

SEQUENCE LISTING (1) GENERAL INFORMATION:

(iii) NUMBER OF SEQUENCES: 63

(2) INFORMATION FOR SEQ ID NO:1:

(i) SEQUENCE CHARACTERISTICS:
      (A) LENGTH: 1162 base pairs
      (B) TYPE: nucleic acid
      (C) STRANDEDNESS: single
      (D) TOPOLOGY: circular (ii) MOLECULE TYPE: DNA (genomic)

(iii) HYPOTHETICAL: NO (iv) ANTI-SENSE: NO (vi) ORIGINAL SOURCE:
      (A) ORGANISM: Tomato Mottle Gemini Virus
      (C) INDIVIDUAL ISOLATE: Florida (ix) FEATURE:
      (A) NAME/KEY: CDS
      (B) LOCATION: 44..1127

(x) PUBLICATION INFORMATION:
      (A) AUTHORS: Gilbertson, RL
         Hidayat, SH
         Paplomatas, EJ
         Rojas, MR
         Hou, YM
         Maxwell, DP
      (B) TITLE: Pseudorecombination between the infectious
         cloned DNA components of tomato mottle and bean
         dwarf mosaic geminiviruses.
      (C) JOURNAL: Jour. General Virol.
      (D) VOLUME: 74
      (F) PAGES: 23-31
      (G) DATE: 1993

(xi) SEQUENCE DESCRIPTION: SEQ ID NO:1:

```
GGATCCGAGT AACTCATCTG GAGTACCCCT TCTTATTACA AAA ATG CCC CCA CCA        55
                                              Met Pro Pro Pro
                                                1

AAG AAA TTT AGA GTT CAG TCA AAG AAC TAT TTC CTC ACT TAT CCA CAG       103
Lys Lys Phe Arg Val Gln Ser Lys Asn Tyr Phe Leu Thr Tyr Pro Gln
  5              10                  15                  20

TGC TCT TTG TCT AAA GAA GAA GCA CTT TCC CAA TTA CAA AAC CTA AAT       151
Cys Ser Leu Ser Lys Glu Glu Ala Leu Ser Gln Leu Gln Asn Leu Asn
                25                  30                  35

ACC CCA GTC AAT AAG AAA TTC ATC AAA ATT TGC AGA GAG CTT CAT GAA       199
Thr Pro Val Asn Lys Lys Phe Ile Lys Ile Cys Arg Glu Leu His Glu
            40                  45                  50
```

```
                                                          -continued

AAT GGG GAA CCT CAT CTC CAT GTG CTT GTT CAG TTC GAA GGA AAG TAC      247
Asn Gly Glu Pro His Leu His Val Leu Val Gln Phe Glu Gly Lys Tyr
             55                  60                  65

CAG TGC ACG AAT AAC AGA TTC TTC GAC CTG GTC TCC CCA ACC CGG TCA      295
Gln Cys Thr Asn Asn Arg Phe Phe Asp Leu Val Ser Pro Thr Arg Ser
         70                  75                  80

GCA CAT TTC CAT CCG AAT ATT CAG GGA GCT AAA TCG AGC TCC GAC GTC      343
Ala His Phe His Pro Asn Ile Gln Gly Ala Lys Ser Ser Ser Asp Val
 85                  90                  95                 100

AAA TCG TAC ATC GAC AAG GAC GGA GAT ACA ATC GAA TGG GGA GAT TTC      391
Lys Ser Tyr Ile Asp Lys Asp Gly Asp Thr Ile Glu Trp Gly Asp Phe
                105                 110                 115

CAG ATC GAC GGC AGA TCT GCC AGA GGA GGC CAG CAG TCT GCT AAT GAT      439
Gln Ile Asp Gly Arg Ser Ala Arg Gly Gly Gln Gln Ser Ala Asn Asp
            120                 125                 130

TCA TAT GCG AAA GCG TTA AAT GCA AGT TCG GTT CAA TCT GCC TTA GCA      487
Ser Tyr Ala Lys Ala Leu Asn Ala Ser Ser Val Gln Ser Ala Leu Ala
        135                 140                 145

GTT CTA AGG GAA GAA CAA CCA AAA GAT TTT GTA TTA CAA AAT CAT AAC      535
Val Leu Arg Glu Glu Gln Pro Lys Asp Phe Val Leu Gln Asn His Asn
    150                 155                 160

ATC CGC TCT AAC CTA GAA CGA ATA TTC GCA AAG GCT CCG GAA CCG TGG      583
Ile Arg Ser Asn Leu Glu Arg Ile Phe Ala Lys Ala Pro Glu Pro Trp
165                 170                 175                 180

GTT CCT CCA TTT CAA GTC TCT TCT TTC ACT AAC GTT CCT GAC GAG ATG      631
Val Pro Pro Phe Gln Val Ser Ser Phe Thr Asn Val Pro Asp Glu Met
                185                 190                 195

CAG GAA TGG GCG GAT AAT TAT TTC GGG ACG GGT GCA GCT GCG CGG CCA      679
Gln Glu Trp Ala Asp Asn Tyr Phe Gly Thr Gly Ala Ala Ala Arg Pro
            200                 205                 210

GAG AGA CCT GTA AGT ATC ATC GTC GAG GGT GAT TCA AGA ACA GGG AAG      727
Glu Arg Pro Val Ser Ile Ile Val Glu Gly Asp Ser Arg Thr Gly Lys
        215                 220                 225

ACG ATG TGG GCA CGT GCG TTA GGC CCA CAT AAC TAT CTC AGT GGA CAC      775
Thr Met Trp Ala Arg Ala Leu Gly Pro His Asn Tyr Leu Ser Gly His
    230                 235                 240

CTA GAC TTC AAT GGT CGA GTC TTC TCG AAT GAT GTG CAG TAT AAC GTC      823
Leu Asp Phe Asn Gly Arg Val Phe Ser Asn Asp Val Gln Tyr Asn Val
245                 250                 255                 260

ATT GAT GAC ATC GCA CCG CAT TAT CTA AAG CTA AAG CAC TGG AAA GAA      871
Ile Asp Asp Ile Ala Pro His Tyr Leu Lys Leu Lys His Trp Lys Glu
                265                 270                 275

TTG CTA GGG GCC CAG AAA GAT TGG CAA TCA AAT TGC AAG TAC GGT AAG      919
Leu Leu Gly Ala Gln Lys Asp Trp Gln Ser Asn Cys Lys Tyr Gly Lys
            280                 285                 290

CCA GTT CAA ATT AAA GGC GGA ATC CCA GCA ATC GTG CTT TGC AAT CCT      967
Pro Val Gln Ile Lys Gly Gly Ile Pro Ala Ile Val Leu Cys Asn Pro
        295                 300                 305

GGT GAG GGT GCC AGC TAT AAA GAG TTC TTA GAC AAA GCA GAA AAT ACA     1015
Gly Glu Gly Ala Ser Tyr Lys Glu Phe Leu Asp Lys Ala Glu Asn Thr
    310                 315                 320

GGT CTA AAG AAC TGG ACT GTC AAG AAT GCG ATC TTC ATC ACC CTC ACA     1063
Gly Leu Lys Asn Trp Thr Val Lys Asn Ala Ile Phe Ile Thr Leu Thr
325                 330                 335                 340

GCC CCC CTC TAT CAA GAC AGC ACA CAG GCA AGC CAA GAA ACG GGC AAT     1111
Ala Pro Leu Tyr Gln Asp Ser Thr Gln Ala Ser Gln Glu Thr Gly Asn
                345                 350                 355

CAG AAG GCG CAG GGT   T GATCTACAGT GCGGGTGCTC CATCTACTTC CTAGG      1162
Gln Lys Ala Gln Gly
            360
```

(2) INFORMATION FOR SEQ ID NO:2:

(i) SEQUENCE CHARACTERISTICS:
        (A) LENGTH: 361 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Pro Lys Lys Phe Arg Val Gln Ser Lys Asn Tyr Phe Leu
 1               5                  10                  15

Thr Tyr Pro Gln Cys Ser Leu Ser Lys Glu Glu Ala Leu Ser Gln Leu
                20                  25                  30

Gln Asn Leu Asn Thr Pro Val Asn Lys Lys Phe Ile Lys Ile Cys Arg
                35                  40                  45

Glu Leu His Glu Asn Gly Glu Pro His Leu His Val Leu Val Gln Phe
     50                  55                  60

Glu Gly Lys Tyr Gln Cys Thr Asn Asn Arg Phe Phe Asp Leu Val Ser
 65                  70                  75                  80

Pro Thr Arg Ser Ala His Phe His Pro Asn Ile Gln Gly Ala Lys Ser
                85                  90                  95

Ser Ser Asp Val Lys Ser Tyr Ile Asp Lys Asp Gly Asp Thr Ile Glu
                100                 105                 110

Trp Gly Asp Phe Gln Ile Asp Gly Arg Ser Ala Arg Gly Gly Gln Gln
                115                 120                 125

Ser Ala Asn Asp Ser Tyr Ala Lys Ala Leu Asn Ala Ser Ser Val Gln
                130                 135                 140

Ser Ala Leu Ala Val Leu Arg Glu Glu Gln Pro Lys Asp Phe Val Leu
145                 150                 155                 160

Gln Asn His Asn Ile Arg Ser Asn Leu Glu Arg Ile Phe Ala Lys Ala
                165                 170                 175

Pro Glu Pro Trp Val Pro Pro Phe Gln Val Ser Ser Phe Thr Asn Val
                180                 185                 190

Pro Asp Glu Met Gln Glu Trp Ala Asp Asn Tyr Phe Gly Thr Gly Ala
                195                 200                 205

Ala Ala Arg Pro Glu Arg Pro Val Ser Ile Ile Val Glu Gly Asp Ser
                210                 215                 220

Arg Thr Gly Lys Thr Met Trp Ala Arg Ala Leu Gly Pro His Asn Tyr
225                 230                 235                 240

Leu Ser Gly His Leu Asp Phe Asn Gly Arg Val Phe Ser Asn Asp Val
                245                 250                 255

Gln Tyr Asn Val Ile Asp Asp Ile Ala Pro His Tyr Leu Lys Leu Lys
                260                 265                 270

His Trp Lys Glu Leu Leu Gly Ala Gln Lys Asp Trp Gln Ser Asn Cys
                275                 280                 285

Lys Tyr Gly Lys Pro Val Gln Ile Lys Gly Gly Ile Pro Ala Ile Val
                290                 295                 300

Leu Cys Asn Pro Gly Glu Gly Ala Ser Tyr Lys Glu Phe Leu Asp Lys
305                 310                 315                 320

Ala Glu Asn Thr Gly Leu Lys Asn Trp Thr Val Lys Asn Ala Ile Phe
                325                 330                 335

Ile Thr Leu Thr Ala Pro Leu Tyr Gln Asp Ser Thr Gln Ala Ser Gln
                340                 345                 350
```

```
Glu Thr Gly Asn Gln Lys Ala Gln Gly
        355                 360
```

(2) INFORMATION FOR SEQ ID NO:3:

(i) SEQUENCE CHARACTERISTICS:
        (A) LENGTH: 1169 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Tomato Mottle Gemini Virus
        (B) STRAIN: Florida (ix) FEATURE:
        (A) NAME/KEY: CDS
        (B) LOCATION: 44..1127

(x) PUBLICATION INFORMATION:
        (A) AUTHORS: Gilbertson, RL et al.
        (B) TITLE: Pseudorecombination between the infectious
            cloned DNA components of tomato mottle and bean
            dwarf mosaic geminivirus.
        (C) JOURNAL: Journal of General Virology
        (D) VOLUME: 74
        (F) PAGES: 23-31
        (G) DATE: 1993

(xi) SEQUENCE DESCRIPTION: SEQ ID NO:3:

```
GGATCCGAGT AACTCATCTG GAGTACCCCT TCTTATTACA AAA ATG CCC CCA CCA      55
                                              Met Pro Pro Pro
                                               1

AAG AAA TTT AGA GTT CAG TCA AAG AAC TAT TTC CTC ACT TAT CCA CAG     103
Lys Lys Phe Arg Val Gln Ser Lys Asn Tyr Phe Leu Thr Tyr Pro Gln
 5              10                  15                  20

TGC TCT TTG TCT AAA GAA GAA GCA CTT TCC CAA TTA CAA AAC CTA AAT     151
Cys Ser Leu Ser Lys Glu Glu Ala Leu Ser Gln Leu Gln Asn Leu Asn
             25                  30                  35

ACC CCA GTC AAT AAG AAA TTC ATC AAA ATT TGC AGA GAG CTT CAT GAA     199
Thr Pro Val Asn Lys Lys Phe Ile Lys Ile Cys Arg Glu Leu His Glu
         40                  45                  50

AAT GGG GAA CCT CAT CTC CAT GTG CTT GTT CAG TTC GAA GGA AAG TAC     247
Asn Gly Glu Pro His Leu His Val Leu Val Gln Phe Glu Gly Lys Tyr
     55                  60                  65

CAG TGC ACG AAT AAC AGA TTC TTC GAC CTG GTC TCC CCA ACC CGG TCA     295
Gln Cys Thr Asn Asn Arg Phe Phe Asp Leu Val Ser Pro Thr Arg Ser
 70                  75                  80

GCA CAT TTC CAT CCG AAT ATT CAG GGA GCT AAA TCG AGC TCC GAC GTC     343
Ala His Phe His Pro Asn Ile Gln Gly Ala Lys Ser Ser Ser Asp Val
 85                  90                  95                 100

AAA TCG TAC ATC GAC AAG GAC GGA GAT ACA ATC GAA TGG GGA GAT TTC     391
Lys Ser Tyr Ile Asp Lys Asp Gly Asp Thr Ile Glu Trp Gly Asp Phe
                 105                 110                 115

CAG ATC GAC GGC AGA TCT GCC AGA GGA GGC CAG CAG TCT GCT AAT GAT     439
Gln Ile Asp Gly Arg Ser Ala Arg Gly Gly Gln Gln Ser Ala Asn Asp
             120                 125                 130

TCA TAT GCG AAA GCG TTA AAT GCA AGT TCG GTT CAA TCT GCC TTA GCA     487
Ser Tyr Ala Lys Ala Leu Asn Ala Ser Ser Val Gln Ser Ala Leu Ala
         135                 140                 145

GTT CTA AGG GAA GAA CAA CCA AAA GAT TTT GTA TTA CAA AAT CAT AAC     535
```

```
Val Leu Arg Glu Glu Gln Pro Lys Asp Phe Val Leu Gln Asn His Asn
    150                 155                 160

ATC CGC TCT AAC CTA GAA CGA ATA TTC GCA AAG GCT CCG GAA CCG TGG      583
Ile Arg Ser Asn Leu Glu Arg Ile Phe Ala Lys Ala Pro Glu Pro Trp
165             170                 175                 180

GTT CCT CCA TTT CAA GTC TCT TCT TTC ACT AAC GTT CCT GAC GAG ATG      631
Val Pro Pro Phe Gln Val Ser Ser Phe Thr Asn Val Pro Asp Glu Met
                185                 190                 195

CAG GAA TGG GCG GAT AAT TAT TTC GGG ACG GGT GCA GCT GCG CGG CCA      679
Gln Glu Trp Ala Asp Asn Tyr Phe Gly Thr Gly Ala Ala Ala Arg Pro
            200                 205                 210

GAG AGA CCT GTA AGT ATC ATC GTC GAG GGT GAT TCA AGA ACA GGG CAC      727
Glu Arg Pro Val Ser Ile Ile Val Glu Gly Asp Ser Arg Thr Gly His
        215                 220                 225

ACG ATG TGG GCA CGT GCG TTA GGC CCA CAT AAC TAT CTC AGT GGA CAC      775
Thr Met Trp Ala Arg Ala Leu Gly Pro His Asn Tyr Leu Ser Gly His
    230                 235                 240

CTA GAC TTC AAT GGT CGA GTC TTC TCG AAT GAT GTG CAG TAT AAC GTC      823
Leu Asp Phe Asn Gly Arg Val Phe Ser Asn Asp Val Gln Tyr Asn Val
245                 250                 255                 260

ATT AAA TAC ATC GCA CCG CAT TAT CTA AAG CTA AAG CAC TGG AAA GAA      871
Ile Lys Tyr Ile Ala Pro His Tyr Leu Lys Leu Lys His Trp Lys Glu
                265                 270                 275

TTG CTA GGG GCC CAG AAA GAT TGG CAA TCA AAT TGC AAG TAC GGT AAG      919
Leu Leu Gly Ala Gln Lys Asp Trp Gln Ser Asn Cys Lys Tyr Gly Lys
            280                 285                 290

CCA GTT CAA ATT AAA GGC GGA ATC CCA GCA ATC GTG CTT TGC AAT CCT      967
Pro Val Gln Ile Lys Gly Gly Ile Pro Ala Ile Val Leu Cys Asn Pro
        295                 300                 305

GGT GAG GGT GCC AGC TAT AAA GAG TTC TTA GAC AAA GCA GAA AAT ACA     1015
Gly Glu Gly Ala Ser Tyr Lys Glu Phe Leu Asp Lys Ala Glu Asn Thr
    310                 315                 320

GGT CTA AAG AAC TGG ACT GTC AAG AAT GCG ATC TTC ATC ACC CTC ACA     1063
Gly Leu Lys Asn Trp Thr Val Lys Asn Ala Ile Phe Ile Thr Leu Thr
325                 330                 335                 340

GCC CCC CTC TAT CAA GAC AGC ACA CAG GCA AGC CAA GAA ACG GGC AAT     1111
Ala Pro Leu Tyr Gln Asp Ser Thr Gln Ala Ser Gln Glu Thr Gly Asn
                345                 350                 355

CAG AAG GCG CAG GGT T GATCTACAGT GCGGGTGCTC CATCTACTTC              1157
Gln Lys Ala Gln Gly
            360

CACTTAGACT GT                                                       1169

(2) INFORMATION FOR SEQ ID NO:4:

(i) SEQUENCE CHARACTERISTICS:
        (A) LENGTH: 361 amino acids
        (B) TYPE: amino acid
        (D) TOPOLOGY: linear (ii) MOLECULE TYPE: protein (xi) SEQUENCE DESCRIPTION: SEQ ID NO:4:

Met Pro Pro Lys Lys Phe Arg Val Gln Ser Lys Asn Tyr Phe Leu
1               5                   10                  15

Thr Tyr Pro Gln Cys Ser Leu Ser Lys Glu Glu Ala Leu Ser Gln Leu
            20                  25                  30

Gln Asn Leu Asn Thr Pro Val Asn Lys Lys Phe Ile Lys Ile Cys Arg
        35                  40                  45

Glu Leu His Glu Asn Gly Glu Pro His Leu His Val Leu Val Gln Phe
```

-continued

```
                    50                      55                      60
Glu Gly Lys Tyr Gln Cys Thr Asn Asn Arg Phe Phe Asp Leu Val Ser
 65                      70                      75                      80

Pro Thr Arg Ser Ala His Phe His Pro Asn Ile Gln Gly Ala Lys Ser
                     85                      90                      95

Ser Ser Asp Val Lys Ser Tyr Ile Asp Lys Asp Gly Asp Thr Ile Glu
                    100                     105                     110

Trp Gly Asp Phe Gln Ile Asp Gly Arg Ser Ala Arg Gly Gly Gln Gln
                    115                     120                     125

Ser Ala Asn Asp Ser Tyr Ala Lys Ala Leu Asn Ala Ser Ser Val Gln
130                     135                     140

Ser Ala Leu Ala Val Leu Arg Glu Glu Gln Pro Lys Asp Phe Val Leu
145                     150                     155                     160

Gln Asn His Asn Ile Arg Ser Asn Leu Glu Arg Ile Phe Ala Lys Ala
                    165                     170                     175

Pro Glu Pro Trp Val Pro Pro Phe Gln Val Ser Ser Phe Thr Asn Val
                    180                     185                     190

Pro Asp Glu Met Gln Glu Trp Ala Asp Asn Tyr Phe Gly Thr Gly Ala
                    195                     200                     205

Ala Ala Arg Pro Glu Arg Pro Val Ser Ile Ile Val Glu Gly Asp Ser
210                     215                     220

Arg Thr Gly His Thr Met Trp Ala Arg Ala Leu Gly Pro His Asn Tyr
225                     230                     235                     240

Leu Ser Gly His Leu Asp Phe Asn Gly Arg Val Phe Ser Asn Asp Val
                    245                     250                     255

Gln Tyr Asn Val Ile Lys Tyr Ile Ala Pro His Tyr Leu Lys Leu Lys
                    260                     265                     270

His Trp Lys Glu Leu Leu Gly Ala Gln Lys Asp Trp Gln Ser Asn Cys
                    275                     280                     285

Lys Tyr Gly Lys Pro Val Gln Ile Lys Gly Gly Ile Pro Ala Ile Val
                    290                     295                     300

Leu Cys Asn Pro Gly Glu Gly Ala Ser Tyr Lys Glu Phe Leu Asp Lys
305                     310                     315                     320

Ala Glu Asn Thr Gly Leu Lys Asn Trp Thr Val Lys Asn Ala Ile Phe
                    325                     330                     335

Ile Thr Leu Thr Ala Pro Leu Tyr Gln Asp Ser Thr Gln Ala Ser Gln
                    340                     345                     350

Glu Thr Gly Asn Gln Lys Ala Gln Gly
                    355                     360
```

(2) INFORMATION FOR SEQ ID NO:5:

(i) SEQUENCE CHARACTERISTICS:
       (A) LENGTH: 1169 base pairs
       (B) TYPE: nucleic acid
       (C) STRANDEDNESS: single
       (D) TOPOLOGY: circular (ii) MOLECULE TYPE: DNA (genomic)

(iii) HYPOTHETICAL: NO (iv) ANTI-SENSE: NO (vi) ORIGINAL SOURCE:
       (A) ORGANISM: Tomato Mottle Gemini Virus
       (B) STRAIN: Florida (ix) FEATURE:

(A) NAME/KEY: CDS
        (B) LOCATION: 44..1127

(xi) SEQUENCE DESCRIPTION: SEQ ID NO:5:

```
GGATCCGAGT AACTCATCTG GAGTACCCCT TCTTATTACA AAA ATG CCC CCA CCA          55
                                              Met Pro Pro Pro
                                                1

AAG AAA TTT AGA GTT CAG TCA AAG AAC TAT TTC CTC ACT TAT CCA CAG         103
Lys Lys Phe Arg Val Gln Ser Lys Asn Tyr Phe Leu Thr Tyr Pro Gln
  5              10                  15                  20

TGC TCT TTG TCT AAA GAA GAA GCA CTT TCC CAA TTA CAA AAC CTA AAT         151
Cys Ser Leu Ser Lys Glu Glu Ala Leu Ser Gln Leu Gln Asn Leu Asn
             25                  30                  35

ACC CCA GTC AAT AAG AAA TTC ATC AAA ATT TGC AGA GAG CTT CAT GAA         199
Thr Pro Val Asn Lys Lys Phe Ile Lys Ile Cys Arg Glu Leu His Glu
         40                  45                  50

AAT GGG GAA CCT CAT CTC CAT GTG CTT GTT CAG TTC GAA GGA AAG TAC         247
Asn Gly Glu Pro His Leu His Val Leu Val Gln Phe Glu Gly Lys Tyr
     55                  60                  65

CAG TGC ACG AAT AAC AGA TTC TTC GAC CTG GTC TCC CCA ACC CGG TCA         295
Gln Cys Thr Asn Asn Arg Phe Phe Asp Leu Val Ser Pro Thr Arg Ser
 70                  75                  80

GCA CAT TTC CAT CCG AAT ATT CAG GGA GCT AAA TCG AGC TCC GAC GTC         343
Ala His Phe His Pro Asn Ile Gln Gly Ala Lys Ser Ser Ser Asp Val
 85                  90                  95                 100

AAA TCG TAC ATC GAC AAG GAC GGA GAT ACA ATC GAA TGG GGA GAT TTC         391
Lys Ser Tyr Ile Asp Lys Asp Gly Asp Thr Ile Glu Trp Gly Asp Phe
                105                 110                 115

CAG ATC GAC GGC AGA TCT GCC AGA GGA GGC CAG CAG TCT GCT AAT GAT         439
Gln Ile Asp Gly Arg Ser Ala Arg Gly Gly Gln Gln Ser Ala Asn Asp
            120                 125                 130

TCA TAT GCG AAA GCG TTA AAT GCA AGT TCG GTT CAA TCT GCC TTA GCA         487
Ser Tyr Ala Lys Ala Leu Asn Ala Ser Ser Val Gln Ser Ala Leu Ala
        135                 140                 145

GTT CTA AGG GAA GAA CAA CCA AAA GAT TTT GTA TTA CAA AAT CAT AAC         535
Val Leu Arg Glu Glu Gln Pro Lys Asp Phe Val Leu Gln Asn His Asn
    150                 155                 160

ATC CGC TCT AAC CTA GAA CGA ATA TTC GCA AAG GCT CCG GAA CCG TGG         583
Ile Arg Ser Asn Leu Glu Arg Ile Phe Ala Lys Ala Pro Glu Pro Trp
165                 170                 175                 180

GTT CCT CCA TTT CAA GTC TCT TCT TTC ACT AAC GTT CCT GAC GAG ATG         631
Val Pro Pro Phe Gln Val Ser Ser Phe Thr Asn Val Pro Asp Glu Met
                185                 190                 195

CAG GAA TGG GCG GAT AAT TAT TTC GGG ACG GGT GCA GCT GCG CGG CCA         679
Gln Glu Trp Ala Asp Asn Tyr Phe Gly Thr Gly Ala Ala Ala Arg Pro
            200                 205                 210

GAG AGA CCT GTA AGT ATC ATC GTC GAG GGT GAT TCA AGA ACA GGG CAC         727
Glu Arg Pro Val Ser Ile Ile Val Glu Gly Asp Ser Arg Thr Gly His
        215                 220                 225

ACG ATG TGG GCA CGT GCG TTA GGC CCA CAT AAC TAT CTC AGT GGA CAC         775
Thr Met Trp Ala Arg Ala Leu Gly Pro His Asn Tyr Leu Ser Gly His
    230                 235                 240

CTA GAC TTC AAT GGT CGA GTC TTC TCG AAT GAT GTG CAG TAT AAC GTC         823
Leu Asp Phe Asn Gly Arg Val Phe Ser Asn Asp Val Gln Tyr Asn Val
245                 250                 255                 260

ATT GAT GAC ATC GCA CCG CAT TAT CTA AAG CTA AAG CAC TGG AAA GAA         871
Ile Asp Asp Ile Ala Pro His Tyr Leu Lys Leu Lys His Trp Lys Glu
                265                 270                 275

TTG CTA GGG GCC CAG AAA GAT TGG CAA TCA AAT TGC AAG TAC GGT AAG         919
Leu Leu Gly Ala Gln Lys Asp Trp Gln Ser Asn Cys Lys Tyr Gly Lys
```

-continued

```
                 280                 285                 290
CCA GTT CAA ATT AAA GGC GGA ATC CCA GCA ATC GTG CTT TGC AAT CCT    967
Pro Val Gln Ile Lys Gly Gly Ile Pro Ala Ile Val Leu Cys Asn Pro
        295                 300                 305

GGT GAG GGT GCC AGC TAT AAA GAG TTC TTA GAC AAA GCA GAA AAT ACA   1015
Gly Glu Gly Ala Ser Tyr Lys Glu Phe Leu Asp Lys Ala Glu Asn Thr
310                 315                 320

GGT CTA AAG AAC TGG ACT GTC AAG AAT GCG ATC TTC ATC ACC CTC ACA   1063
Gly Leu Lys Asn Trp Thr Val Lys Asn Ala Ile Phe Ile Thr Leu Thr
325                 330                 335                 340

GCC CCC CTC TAT CAA GAC AGC ACA CAG GCA AGC CAA GAA ACG GGC AAT   1111
Ala Pro Leu Tyr Gln Asp Ser Thr Gln Ala Ser Gln Glu Thr Gly Asn
                345                 350                 355

CAG AAG GCG CAG GGT T GATCTACAGT GCGGGTGCTC CATCTACTTC            1157
Gln Lys Ala Gln Gly
            360

CACTTAGACT GT                                                      1169
```

(2) INFORMATION FOR SEQ ID NO:6:

(i) SEQUENCE CHARACTERISTICS:
        (A) LENGTH: 361 amino acids
        (B) TYPE: amino acid
        (D) TOPOLOGY: linear (ii) MOLECULE TYPE: protein (xi) SEQUENCE DESCRIPTION: SEQ ID NO:6:

```
Met Pro Pro Lys Lys Phe Arg Val Gln Ser Lys Asn Tyr Phe Leu
 1               5                  10                  15

Thr Tyr Pro Gln Cys Ser Leu Ser Lys Glu Ala Leu Ser Gln Leu
                20                  25                  30

Gln Asn Leu Asn Thr Pro Val Asn Lys Lys Phe Ile Lys Ile Cys Arg
            35                  40                  45

Glu Leu His Glu Asn Gly Glu Pro His Leu His Val Leu Val Gln Phe
        50                  55                  60

Glu Gly Lys Tyr Gln Cys Thr Asn Asn Arg Phe Phe Asp Leu Val Ser
65                  70                  75                  80

Pro Thr Arg Ser Ala His Phe His Pro Asn Ile Gln Gly Ala Lys Ser
                85                  90                  95

Ser Ser Asp Val Lys Ser Tyr Ile Asp Lys Asp Gly Asp Thr Ile Glu
            100                 105                 110

Trp Gly Asp Phe Gln Ile Asp Gly Arg Ser Ala Arg Gly Gly Gln Gln
        115                 120                 125

Ser Ala Asn Asp Ser Tyr Ala Lys Ala Leu Asn Ala Ser Ser Val Gln
    130                 135                 140

Ser Ala Leu Ala Val Leu Arg Glu Glu Pro Lys Asp Phe Val Leu
145                 150                 155                 160

Gln Asn His Asn Ile Arg Ser Asn Leu Glu Arg Ile Phe Ala Lys Ala
                165                 170                 175

Pro Glu Pro Trp Val Pro Pro Phe Gln Val Ser Ser Phe Thr Asn Val
            180                 185                 190

Pro Asp Glu Met Gln Glu Trp Ala Asp Asn Tyr Phe Gly Thr Gly Ala
        195                 200                 205

Ala Ala Arg Pro Glu Arg Pro Val Ser Ile Ile Val Glu Gly Asp Ser
    210                 215                 220

Arg Thr Gly His Thr Met Trp Ala Arg Ala Leu Gly Pro His Asn Tyr
```

```
225                    230                    235                    240
Leu Ser Gly His Leu Asp Phe Asn Gly Arg Val Phe Ser Asn Asp Val
                245                    250                    255

Gln Tyr Asn Val Ile Asp Asp Ile Ala Pro His Tyr Leu Lys Leu Lys
                260                    265                    270

His Trp Lys Glu Leu Leu Gly Ala Gln Lys Asp Trp Gln Ser Asn Cys
                275                    280                    285

Lys Tyr Gly Lys Pro Val Gln Ile Lys Gly Gly Ile Pro Ala Ile Val
                290                    295                    300

Leu Cys Asn Pro Gly Glu Gly Ala Ser Tyr Lys Glu Phe Leu Asp Lys
305                    310                    315                    320

Ala Glu Asn Thr Gly Leu Lys Asn Trp Thr Val Lys Asn Ala Ile Phe
                325                    330                    335

Ile Thr Leu Thr Ala Pro Leu Tyr Gln Asp Ser Thr Gln Ala Ser Gln
                340                    345                    350

Glu Thr Gly Asn Gln Lys Ala Gln Gly
                355                    360
```

(2) INFORMATION FOR SEQ ID NO:7:

(i) SEQUENCE CHARACTERISTICS:
        (A) LENGTH: 1169 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Tomato Mottle Gemini Virus
        (B) STRAIN: Florida (ix) FEATURE:
        (A) NAME/KEY: CDS
        (B) LOCATION: 44..1127

(xi) SEQUENCE DESCRIPTION: SEQ ID NO:7:

```
GGATCCGAGT AACTCATCTG GAGTACCCCT TCTTATTACA AAA ATG CCC CCA CCA         55
                                              Met Pro Pro Pro
                                                1

AAG AAA TTT AGA GTT CAG TCA AAG AAC TAT TTC CTC ACT TAT CCA CAG        103
Lys Lys Phe Arg Val Gln Ser Lys Asn Tyr Phe Leu Thr Tyr Pro Gln
 5              10                  15                  20

TGC TCT TTG TCT AAA GAA GAA GCA CTT TCC CAA TTA CAA AAC CTA AAT        151
Cys Ser Leu Ser Lys Glu Glu Ala Leu Ser Gln Leu Gln Asn Leu Asn
            25                  30                  35

ACC CCA GTC AAT AAG AAA TTC ATC AAA ATT TGC AGA GAG CTT CAT GAA        199
Thr Pro Val Asn Lys Lys Phe Ile Lys Ile Cys Arg Glu Leu His Glu
        40                  45                  50

AAT GGG GAA CCT CAT CTC CAT GTG CTT GTT CAG TTC GAA GGA AAG TAC        247
Asn Gly Glu Pro His Leu His Val Leu Val Gln Phe Glu Gly Lys Tyr
    55                  60                  65

CAG TGC ACG AAT AAC AGA TTC TTC GAC CTG GTC TCC CCA ACC GGT TCA        295
Gln Cys Thr Asn Asn Arg Phe Phe Asp Leu Val Ser Pro Thr Arg Ser
 70                  75                  80

GCA CAT TTC CAT CCG AAT ATT CAG GGA GCT AAA TCG AGC TCC GAC GTC        343
Ala His Phe His Pro Asn Ile Gln Gly Ala Lys Ser Ser Ser Asp Val
 85                  90                  95                 100
```

```
AAA TCG TAC ATC GAC AAG GAC GGA GAT ACA ATC GAA TGG GGA GAT TTC        391
Lys Ser Tyr Ile Asp Lys Asp Gly Asp Thr Ile Glu Trp Gly Asp Phe
            105                 110                 115

CAG ATC GAC GGC AGA TCT GCC AGA GGA GGC CAG CAG TCT GCT AAT GAT        439
Gln Ile Asp Gly Arg Ser Ala Arg Gly Gly Gln Gln Ser Ala Asn Asp
            120                 125                 130

TCA TAT GCG AAA GCG TTA AAT GCA AGT TCG GTT CAA TCT GCC TTA GCA        487
Ser Tyr Ala Lys Ala Leu Asn Ala Ser Ser Val Gln Ser Ala Leu Ala
            135                 140                 145

GTT CTA AGG GAA GAA CAA CCA AAA GAT TTT GTA TTA CAA AAT CAT AAC        535
Val Leu Arg Glu Glu Gln Pro Lys Asp Phe Val Leu Gln Asn His Asn
    150                 155                 160

ATC CGC TCT AAC CTA GAA CGA ATA TTC GCA AAG GCT CCG GAA CCG TGG        583
Ile Arg Ser Asn Leu Glu Arg Ile Phe Ala Lys Ala Pro Glu Pro Trp
165                 170                 175                 180

GTT CCT CCA TTT CAA GTC TCT TCT TTC ACT AAC GTT CCT GAC GAG ATG        631
Val Pro Pro Phe Gln Val Ser Ser Phe Thr Asn Val Pro Asp Glu Met
            185                 190                 195

CAG GAA TGG GCG GAT AAT TAT TTC GGG ACG GGT GCA GCT GCG CGG CCA        679
Gln Glu Trp Ala Asp Asn Tyr Phe Gly Thr Gly Ala Ala Ala Arg Pro
            200                 205                 210

GAG AGA CCT GTA AGT ATC ATC GTC GAG GGT GAT TCA AGA ACA GGG AAG        727
Glu Arg Pro Val Ser Ile Ile Val Glu Gly Asp Ser Arg Thr Gly Lys
            215                 220                 225

ACG ATG TGG GCA CGT GCG TTA GGC CCA CAT AAC TAT CTC AGT GGA CAC        775
Thr Met Trp Ala Arg Ala Leu Gly Pro His Asn Tyr Leu Ser Gly His
    230                 235                 240

CTA GAC TTC AAT GGT CGA GTC TTC TCG AAT GAT GTG CAG TAT AAC GTC        823
Leu Asp Phe Asn Gly Arg Val Phe Ser Asn Asp Val Gln Tyr Asn Val
245                 250                 255                 260

ATT AAA TAC ATC GCA CCG CAT TAT CTA AAG CTA AAG CAC TGG AAA GAA        871
Ile Lys Tyr Ile Ala Pro His Tyr Leu Lys Leu Lys His Trp Lys Glu
            265                 270                 275

TTG CTA GGG GCC CAG AAA GAT TGG CAA TCA AAT TGC AAG TAC GGT AAG        919
Leu Leu Gly Ala Gln Lys Asp Trp Gln Ser Asn Cys Lys Tyr Gly Lys
            280                 285                 290

CCA GTT CAA ATT AAA GGC GGA ATC CCA GCA ATC GTG CTT TGC AAT CCT        967
Pro Val Gln Ile Lys Gly Gly Ile Pro Ala Ile Val Leu Cys Asn Pro
            295                 300                 305

GGT GAG GGT GCC AGC TAT AAA GAG TTC TTA GAC AAA GCA GAA AAT ACA       1015
Gly Glu Gly Ala Ser Tyr Lys Glu Phe Leu Asp Lys Ala Glu Asn Thr
    310                 315                 320

GGT CTA AAG AAC TGG ACT GTC AAG AAT GCG ATC TTC ATC ACC CTC ACA       1063
Gly Leu Lys Asn Trp Thr Val Lys Asn Ala Ile Phe Ile Thr Leu Thr
325                 330                 335                 340

GCC CCC CTC TAT CAA GAC AGC ACA CAG GCA AGC CAA GAA ACG GGC AAT       1111
Ala Pro Leu Tyr Gln Asp Ser Thr Gln Ala Ser Gln Glu Thr Gly Asn
            345                 350                 355

CAG AAG GCG CAG GGT T GATCTACAGT GCGGGTGCTC CATCTACTTC               1157
Gln Lys Ala Gln Gly
            360

CACTTAGACT GT                                                         1169
```

(2) INFORMATION FOR SEQ ID NO:8:

(i) SEQUENCE CHARACTERISTICS:
        (A) LENGTH: 361 amino acids
        (B) TYPE: amino acid
        (D) TOPOLOGY: linear (ii) MOLECULE TYPE: protein (xi) SEQUENCE DESCRIPTION: SEQ ID NO:8:

```
Met Pro Pro Lys Lys Phe Arg Val Gln Ser Lys Asn Tyr Phe Leu
  1               5                  10                  15

Thr Tyr Pro Gln Cys Ser Leu Ser Lys Glu Ala Leu Ser Gln Leu
                 20                  25                  30

Gln Asn Leu Asn Thr Pro Val Asn Lys Lys Phe Ile Lys Ile Cys Arg
             35                  40                  45

Glu Leu His Glu Asn Gly Glu Pro His Leu His Val Leu Val Gln Phe
         50                  55                  60

Glu Gly Lys Tyr Gln Cys Thr Asn Asn Arg Phe Phe Asp Leu Val Ser
 65                  70                  75                  80

Pro Thr Arg Ser Ala His Phe His Pro Asn Ile Gln Gly Ala Lys Ser
                 85                  90                  95

Ser Ser Asp Val Lys Ser Tyr Ile Asp Lys Asp Gly Asp Thr Ile Glu
            100                 105                 110

Trp Gly Asp Phe Gln Ile Asp Gly Arg Ser Ala Arg Gly Gly Gln Gln
            115                 120                 125

Ser Ala Asn Asp Ser Tyr Ala Lys Ala Leu Asn Ala Ser Ser Val Gln
130                 135                 140

Ser Ala Leu Ala Val Leu Arg Glu Glu Gln Pro Lys Asp Phe Val Leu
145                 150                 155                 160

Gln Asn His Asn Ile Arg Ser Asn Leu Glu Arg Ile Phe Ala Lys Ala
                165                 170                 175

Pro Glu Pro Trp Val Pro Pro Phe Gln Val Ser Ser Phe Thr Asn Val
                180                 185                 190

Pro Asp Glu Met Gln Glu Trp Ala Asp Asn Tyr Phe Gly Thr Gly Ala
                195                 200                 205

Ala Ala Arg Pro Glu Arg Pro Val Ser Ile Ile Val Glu Gly Asp Ser
210                 215                 220

Arg Thr Gly Lys Thr Met Trp Ala Arg Ala Leu Gly Pro His Asn Tyr
225                 230                 235                 240

Leu Ser Gly His Leu Asp Phe Asn Gly Arg Val Phe Ser Asn Asp Val
                245                 250                 255

Gln Tyr Asn Val Ile Lys Tyr Ile Ala Pro His Tyr Leu Lys Leu Lys
                260                 265                 270

His Trp Lys Glu Leu Leu Gly Ala Gln Lys Asp Trp Gln Ser Asn Cys
    275                 280                 285

Lys Tyr Gly Lys Pro Val Gln Ile Lys Gly Gly Ile Pro Ala Ile Val
    290                 295                 300

Leu Cys Asn Pro Gly Glu Gly Ala Ser Tyr Lys Glu Phe Leu Asp Lys
305                 310                 315                 320

Ala Glu Asn Thr Gly Leu Lys Asn Trp Thr Val Lys Asn Ala Ile Phe
                325                 330                 335

Ile Thr Leu Thr Ala Pro Leu Tyr Gln Asp Ser Thr Gln Ala Ser Gln
                340                 345                 350

Glu Thr Gly Asn Gln Lys Ala Gln Gly
                355                 360
```

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single (D) TOPOLOGY: linear (ii) MOLECULE TYPE: other nucleic acid
        (A) DESCRIPTION: /desc = "Oligonucleotide primer"

(iii) HYPOTHETICAL: NO (iv) ANTI-SENSE: NO (vi) ORIGINAL SOURCE:
        (A) ORGANISM: FL2549B (xi) SEQUENCE DESCRIPTION: SEQ ID NO:9:

TATCGGATCC GAGTAACTCA TCTGGAGTAC C                31

(2) INFORMATION FOR SEQ ID NO:10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(iii) HYPOTHETICAL: NO (iv) ANTI-SENSE: NO (vi) ORIGINAL SOURCE:
        (A) ORGANISM: FL1108B (xi) SEQUENCE DESCRIPTION: SEQ ID NO:10:

TATCGGATCC GGAAGTAGAT GGAGCACCCG C                31

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(iii) HYPOTHETICAL: NO (iv) ANTI-SENSE: NO (vi) ORIGINAL SOURCE:
        (A) ORGANISM: PFAC1680

(xi) SEQUENCE DESCRIPTION: SEQ ID NO:11:

CAAGAACAGG GCACACGATG TGGG                        24

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(iii) HYPOTHETICAL: NO (iv) ANTI-SENSE: NO (vi) ORIGINAL SOURCE:

(A) ORGANISM: PFAC1781

(xi) SEQUENCE DESCRIPTION: SEQ ID NO:12:

GTATAACGTC ATTAAATACA TCGCACCGC                                29

(2) INFORMATION FOR SEQ ID NO:13:

(i) SEQUENCE CHARACTERISTICS:
(A) LENGTH: 1166 base pairs
(B) TYPE: nucleic acid
(C) STRANDEDNESS: single
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Tomato Mottle Geminivirus
(C) INDIVIDUAL ISOLATE: Florida (ix) FEATURE:
(A) NAME/KEY: CDS
(B) LOCATION: 44..436

(xi) SEQUENCE DESCRIPTION: SEQ ID NO:13:

```
GGATCCGAGT AACTCATCTG GAGTACCCCT TCTTATTACA AAA ATG CCC CCA CCA        55
                                              Met Pro Pro Pro
                                                1

AAG AAA TTT AGA GTT CAG TCA AAG AAC TAT TTC CTC ACT TAT CCA CAG       103
Lys Lys Phe Arg Val Gln Ser Lys Asn Tyr Phe Leu Thr Tyr Pro Gln
  5              10                  15                  20

TGC TCT TTG TCT AAA GAA GAA GCA CTT TCC CAA TTA CAA AAC CTA AAT       151
Cys Ser Leu Ser Lys Glu Glu Ala Leu Ser Gln Leu Gln Asn Leu Asn
             25                  30                  35

ACC CCA GTC AAT AAG AAA TTC ATC AAA ATT TGC AGA GAG CTT CAT GAA       199
Thr Pro Val Asn Lys Lys Phe Ile Lys Ile Cys Arg Glu Leu His Glu
         40                  45                  50

AAT GGG GAA CCT CAT CTC CAT GTG CTT GTT CAG TTC GAA GGA AAG TAC       247
Asn Gly Glu Pro His Leu His Val Leu Val Gln Phe Glu Gly Lys Tyr
     55                  60                  65

CAG TGC ACG AAT AAC AGA TTC TTC GAC CTG GTC TCC CCA ACC CGG TCA       295
Gln Cys Thr Asn Asn Arg Phe Phe Asp Leu Val Ser Pro Thr Arg Ser
 70                  75                  80

GCA CAT TTC CAT CCG AAT ATT CAG GGA GCT AAA TCG AGC TCC GAC GTC       343
Ala His Phe His Pro Asn Ile Gln Gly Ala Lys Ser Ser Ser Asp Val
 85                  90                  95                 100

AAA TCG TAC ATC GAC AAG GAC GGA GAT ACA ATC GAA TGG GGA GAT TTC       391
Lys Ser Tyr Ile Asp Lys Asp Gly Asp Thr Ile Glu Trp Gly Asp Phe
                105                 110                 115

CAG ATC GAC GGC AGA TCG ATC TGC CAG AGG AGG CCA GCA GTC TGC           436
Gln Ile Asp Gly Arg Ser Ile Cys Gln Arg Arg Pro Ala Val Cys
                120                 125                 130

TAATGATTCA TATGCGAAAG CGTTAAATGC AAGTTCGGTT CAATCTGCCT TAGCAGTTCT     496

AAGGGAAGAA CAACCAAAAG ATTTTGTATT ACAAAATCAT AACATCCGCT CTAACCTAGA     556

ACGAATATTC GCAAAGGCTC CGGAACCGTG GGTTCCTCCA TTTCAAGTCT CTTCTTTCAC     616

TAACGTTCCT GACGAGATGC AGGAATGGGC GGATAATTAT TTCGGGACGG GTGCAGCTGC     676

GCGGCCAGAG AGACCTGTAA GTATCATCGT CGAGGGTGAT TCAAGAACAG GAAGACGAT      736

GTGGGCACGT GCGTTAGGCC CACATAACTA TCTCAGTGGA CACCTAGACT TCAATGGTCG     796
```

| AGTCTTCTCG AATGATGTGC AGTATAACGT CATTGATGAC ATCGCACCGC ATTATCTAAA | 856 |
| GCTAAAGCAC TGGAAAGAAT TGCTAGGGGC CCAGAAAGAT TGGCAATCAA ATTGCAAGTA | 916 |
| CGGTAAGCCA GTTCAAATTA AAGGCGGAAT CCCAGCAATC GTGCTTTGCA ATCCTGGTGA | 976 |
| GGGTGCCAGC TATAAAGAGT TCTTAGACAA AGCAGAAAAT ACAGGTCTAA AGAACTGGAC | 1036 |
| TGTCAAGAAT GCGATCTTCA TCACCCTCAC AGCCCCCCTC TATCAAGACA GCACACAGGC | 1096 |
| AAGCCAAGAA ACGGGCAATC AGAAGGCGCA GGGTTGATCT ACAGTGCGGG TGCTCCATCT | 1156 |
| ACTTCCTAGG | 1166 |

(2) INFORMATION FOR SEQ ID NO:14:

(i) SEQUENCE CHARACTERISTICS:
        (A) LENGTH: 131 amino acids
        (B) TYPE: amino acid
        (D) TOPOLOGY: linear (ii) MOLECULE TYPE: protein (xi) SEQUENCE DESCRIPTION: SEQ ID NO:14:

```
Met Pro Pro Pro Lys Lys Phe Arg Val Gln Ser Lys Asn Tyr Phe Leu
 1               5                  10                  15

Thr Tyr Pro Gln Cys Ser Leu Ser Lys Glu Glu Ala Leu Ser Gln Leu
            20                  25                  30

Gln Asn Leu Asn Thr Pro Val Asn Lys Lys Phe Ile Lys Ile Cys Arg
        35                  40                  45

Glu Leu His Glu Asn Gly Glu Pro His Leu His Val Leu Val Gln Phe
 50                  55                  60

Glu Gly Lys Tyr Gln Cys Thr Asn Asn Arg Phe Phe Asp Leu Val Ser
 65                  70                  75                  80

Pro Thr Arg Ser Ala His Phe His Pro Asn Ile Gln Gly Ala Lys Ser
                85                  90                  95

Ser Ser Asp Val Lys Ser Tyr Ile Asp Lys Asp Gly Asp Thr Ile Glu
            100                 105                 110

Trp Gly Asp Phe Gln Ile Asp Gly Arg Ser Ile Cys Gln Arg Arg Pro
            115                 120                 125

Ala Val Cys
    130
```

(2) INFORMATION FOR SEQ ID NO:15:

(i) SEQUENCE CHARACTERISTICS:
        (A) LENGTH: 1246 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Tomato Mottle Geminivirus
        (B) STRAIN: Florida (x) PUBLICATION INFORMATION:
        (A) AUTHORS: Gilbertson, RL
            Hidayat, SH
            Paplomatas, EJ
            Rojas, MR
            Hou, YM
            Maxwell, DP (B) TITLE: Pseudorecombination between the infectious
            cloned DNA components of tomato mottle and bean
            dwarf mosaic geminiviruses.
        (C) JOURNAL: Journal of General Virology
        (D) VOLUME: 74
        (F) PAGES: 23-31
        (G) DATE: 1993

(xi) SEQUENCE DESCRIPTION: SEQ ID NO:15:

```
AGATCTGCCA GAGGAGGCCA GCAGTCTGCT AATGATTCAT ATGCGAAAGC GTTAAATGCA      60

AGTTCGGTTC AATCTGCCTT AGCAGTTCTA AGGGAAGAAC AACCAAAAGA TTTTGTATTA     120

CAAAATCATA ACATCCGCTC TAACCTAGAA CGAATATTCG CAAAGGCTCC GGAACCGTGG     180

GTTCCTCCAT TTCAAGTCTC TTCTTTCACT AACGTTCCTG ACGAGATGCA GGAATGGGCG     240

GATAATTATT TCGGGACGGG TGCAGCTGCG CGGCCAGAGA GACCTGTAAG TATCATCGTC     300

GAGGGTGATT CAAGAACAGG GAAGACGATG TGGGCACGTG CGTTAGGCCC ACATAACTAT     360

CTCAGTGGAC ACCTAGACTT CAATGGTCGA GTCTTCTCGA ATGATGTGCA GTATAACGTC     420

ATTGATGACA TCGCACCGCA TTATCTAAAG CTAAAGCACT GGAAAGAATT GCTAGGGGCC     480

CAGAAAGATT GGCAATCAAA TTGCAAGTAC GGTAAGCCAG TTCAAATTAA AGGCGGAATC     540

CCAGCAATCG TGCTTTGCAA TCCTGGTGAG GGTGCCAGCT ATAAAGAGTT CTTAGACAAA     600

GCAGAAAATA CAGGTCTAAA GAACTGGACT GTCAAGAATG CGATCTTCAT CACCCTCACA     660

GCCCCCCTCT ATCAAGACAG CACACAGGCA AGCCAAGAAA CGGGCAATCA GAAGGCGCAG     720

GGTTGATCTA CAGTGCGGGT GCTCCATCTA CTTCCACTTA GACTGTGCGG GACATGGATT     780

CACGCACAGG GGAACTCATC ACTGCACATC AGGCGGAGAA TGGCGTGTAT ATCTGGGAGC     840

TAAAAAATCC CCTTTATTTC AAGATACACA GGGTAGAGGA ACCACTGTAT ACCAGAACGA     900

GGGTATACCA CGTACAGATA CGGTTCAACC ACAACCTGAG GAAAGCGTTG CATCTCCACA     960

AAGCCTACCT GAACTTCCAA GTTTGGACGA CGTGGATGAC AGCTTCTGGA TCAATTTATT    1020

TAGCTAGATT TAGATATTTA GTCAACATGT ATCTAGATCA ATTAGGTGTT ATTTCAATAA    1080

ACAATGTAAT TAGAGCTGTA CGTTTCGCAA CAAACAGAGT GTATGTAAAT CATGTATTGG    1140

AGAATCATTC AATAAAATTC AAATTTTATT AATTCATGAT CGAATCATAA AAATAGATTC    1200

GAATTTTCAA AGTTGCATAT ACAGGGTTAG ACGCATGAGT GCATGC                   1246
```

(2) INFORMATION FOR SEQ ID NO:16:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (vi) ORIGINAL SOURCE:
        (A) ORGANISM: FL-2549H (xi) SEQUENCE DESCRIPTION: SEQ ID NO:16:

```
TATCAAAGCT TGAGTAACTC ATCTGGAGTA CC                                    32
```

(2) INFORMATION FOR SEQ ID NO:17:

(i) SEQUENCE CHARACTERISTICS:
        (A) LENGTH: 2602 base pairs
        (B) TYPE: nucleic acid (C) STRANDEDNESS: single
        (D) TOPOLOGY: circular (ii) MOLECULE TYPE: DNA (genomic)

(iii) HYPOTHETICAL: NO (vi) ORIGINAL SOURCE:
        (A) ORGANISM: Tomato Mottle Geminivirus
        (B) STRAIN: Florida (xi) SEQUENCE DESCRIPTION: SEQ ID NO:17:

```
GGGGCATTTT TGTAATAAGA AGGGGTACTC CAGATGAGTT ACTCCAATTG AGCCTTCTCA        60

AACTTGCTCA TTCAATTGGA GTATTAGAGT AACTTATATA TAAGAACCCT CTATAGAACT       120

ATTAATCTGG TTCATACACG TGGCGGCCAT CCGATATAAT ATTACCGGAT GGCCGCGCGC       180

TTTTTTTTAA TCCGTACAGT CCAATACTCT CACATCCAAT CATAATGCGT CGTACAAGCC       240

TATATATTTC CAACAACTTG GGCCTTAAGT TGTTGGAGGC CCATTATAAA TTAAAGTGAT       300

CTTGGCCCAA TGTCTTTAAC TCAAAATGCC TAAGCGTGAT TTGCCATGGC GATCGATGGC       360

GGGAACCTCA AAGGTTAGCC GCAATGCTAA TTATTCTCCT CGTGCAGGTA TTAGGCCAAG       420

AATTAACAAG GCCGCTGAAT GGGTGAATCG GCCCATGTAT AGGAAGCCCA GGATCTATCG       480

GACTCTTAGT ACAACTGACG TGCCCAGGGG CTGTGAAGGC CCATGTAAGG TCCAGTCTTT       540

CGAACAGCGC CATGACATCT CACATATCGG TAAGGTCATG TGCATATCCG ATGTGACACG       600

TGGTAATGGC ATAACCCACC GTGTTGGTAA GCGTTTCTGT GTTAAGTCTG TGTATATCCT       660

TGGTAAGATT TGGATGGATG AGAACATCAA GCTCAAGAAC CACACGAATA GTGTCATGTT       720

CTGGTTGGTC AGAGATCGTA GACCCTATGG TACTCCAATG GATTTTGGAC AGGTGTTCAA       780

CATGTTCGAT AACGAGCCTA GCACTGCTAC TGTCAAAAAC GATCTACGCG ATCGTTACCA       840

GGTCATGCAT AAGTTCTATG CAAGGTGAC AGGTGGACAG TATGCCAGCA ACGAGCAGGC       900

TATAGTTAAG AGGTTCTGGA AGGTGAACAA TCATGTAGTC TATAATCATC AAGAGGCTGG       960

CAAGTACGAG AATCACACAG AGAACGCCTT GTTATTGTAT ATGGCATGCA CTCATGCGTC      1020

TAACCCTGTA TATGCAACTT TGAAAATTCG AATCTATTTT TATGATTCGA TCATGAATTA      1080

ATAAAATTTG AATTTTATTG AATGATTCTC CAATACATGA TTTACATACA CTCTGTTTGT      1140

TGCGAAACGT ACAGCTCTAA TTACATTGTT TATTGAAATA ACACCTAATT GATCTAGATA      1200

CATGTTGACT AAATATCTAA ATCTAGCTAA ATAAATTGAT CCAGAAGCTG TCATCCACGT      1260

CGTCCAAACT TGGAAGTTCA GGTAGGCTTT GTGGAGATGC AACGCTTTCC TCAGGTTGTG      1320

GTTGAACCGT ATCTGTACGT GGTATACCCT CGTTCTGGTA TACAGTGGTT CCTCTACCCT      1380

GTGTATCTTG AAATAAAGGG GATTTTTTAG CTCCCAGATA TACACGCCAT TCTCCGCCTG      1440

ATGTGCAGTG ATGAGTTCCC CTGTGCGTGA ATCCATGTCC CGCACAGTCT AAGTGGAAGT      1500

AGATGGAGCA CCCGCACTGT AGATCAACCC TGCGCCTTCT GATTGCCCGT TTCTTGGCTT      1560

GCCTGTGTGC TGTCTTGATA GAGGGGGGCT GTGAGGGTGA TGAAGATCGC ATTCTTGACA      1620

GTCCAGTTCT TTAGACCTGT ATTTTCTGCT TTGTCTAAGA ACTCTTTATA GCTGGCACCC      1680

TCACCAGGAT TGCAAAGCAC GATTGCTGGG ATTCCGCCTT TAATTTGAAC TGGCTTACCG      1740

TACTTGCAAT TTGATTGCCA ATCTTTCTGG GCCCCTAGCA ATTCTTTCCA GTGCTTTAGC      1800

TTTAGATAAT GCGGTGCGAT GTCATCAATG ACGTTATACT GCACATCATT CGAGAAGACT      1860

CGACCATTGA AGTCTAGGTG TCCACTGAGA TAGTTATGTG GGCCTAACGC ACGTGCCCAC      1920

ATCGTCTTCC CTGTTCTTGA ATCACCCTCG ACGATGATAC TTACAGGTCT CTCTGGCCGC      1980
```

```
GCAGCTGCAC CCGTCCCGAA ATAATTATCC GCCCATTCCT GCATCTCGTC AGGAACGTTA      2040

GTGAAAGAAG AGACTTGAAA TGGAGGAACC CACGGTTCCG GAGCCTTTGC GAATATTCGT      2100

TCTAGGTTAG AGCGGATGTT ATGATTTTGT AATACAAAAT CTTTTGGTTG TTCTTCCCTT      2160

AGAACTGCTA AGGCAGATTG AACCGAACTT GCATTTAACG CTTTCGCATA TGAATCATTA      2220

GCAGACTGCT GGCCTCCTCT GGCAGATCTG CCGTCGATCT GGAAATCTCC CCATTCGATT      2280

GTATCTCCGT CCTTGTCGAT GTACGATTTG ACGTCGGAGC TCGATTTAGC TCCCTGAATA      2340

TTCGGATGGA AATGTGCTGA CCGGGTTGGG GAGACCAGGT CGAAGAATCT GTTATTCGTG      2400

CACTGGTACT TTCCTTCGAA CTGAACAAGC ACATGGAGAT GAGGTTCCCC ATTTTCATGA      2460

AGCTCTCTGC AAATTTTGAT GAATTTCTTA TTGACTGGGG TATTTAGGTT TTGTAATTGG      2520

GAAAGTGCTT CTTCTTTAGA CAAAGAGCAC TGTGGATAAG TGAGGAAATA GTTCTTTGAC      2580

TGAACTCTAA ATTTCTTTGG TG                                              2602
```

(2) INFORMATION FOR SEQ ID NO:18:

(i) SEQUENCE CHARACTERISTICS:
        (A) LENGTH: 2540 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (vi) ORIGINAL SOURCE:
        (A) ORGANISM: Tomato Mottle Geminivirus
        (B) STRAIN: Florida (xi) SEQUENCE DESCRIPTION: SEQ ID NO:18:

```
GTGGCATTTT TGTAATAAGA AGGGGTACTC CAGATGAGTT ACTCCAATTG AGCCTTCTCA        60

AACTTGCTCA TTCAATTGGA GTATTAGAGT AACTTATATA TAAGAACCCT CTATAGAATT       120

ATTAATCTGG TTCATACACG TGGCGGCCAT CCGATATAAT ATTACCGGAT GGCCGCGCCC       180

CCCCCCCTTT TATACGCGCG CCTCTTTTGT CGTATTTCCA CGCTTCTTCC TGTTGGTGCG       240

TATCCTTCAC TTCCCATCTT TTTGAGTAGC CTTTAATTTG AATTAAAGGT TAAAACTTTA       300

TCGCGATGAC TAATCATATC ACATTGACCA TGTGAAGGAC GTGGCATTAT TTCGACCATG       360

CTGCTGAGTT TATTTGCTAT TATTGTTCTA TCCATAATCT ATATATTGGA TTGGTCAGGA       420

ATATTTTGTT TATCCAACTC AGCTGCATAC CACGTTTATA TCGTTAGCTA AATTTTGATT       480

AATCTTAGTT AAGTGTTTGA CTATGTATCC TTTAAAGTGT AAACGTGGTT TATCATATTC       540

AAATCGAAGA TTTAACTCAC GTAATAATGT GTTTAACCGT CCAGTTTCTG GTAAGAGACA       600

TGATGGAAAG CGTCGGGGAG GTAATTTCGT GAAGCCCAAT GATGAGCCCA AGATGTTAGC       660

CCAACGCATA CATGAGAATC AGTATGGGCC TGAATTTGTA TTGGCCCATA ACTCAGCTAT       720

CTCCACATTT ATCAGTTATC CCATCTTGGG CAAGTCCGAA GCCAGTCGAA GTAGGTCCTA       780

TATCAAGTTG AAACGTCTTC GTTTCAAAGG GACTGTGAAG ATTGAGCGTG TTCAATCTGA       840

TTTGAACATG GATGGCTTTA TGCCTAAAGT CGAAGGAGTA TTCTCTATGG TTGTTGTTGT       900

GGATCGTAAA CCACACTTGG GTCCCTCCGG GTGTTTGCAT ACATTCGACG AGCTATTGG       960

TGCAAGGATC AATAGTCATG GCAACCTCAC TATAGTACCT TCTCTGAAAG ACCGCTTCTA      1020

CATTAGACAT GTGTTCAAGC GAGTGCTCTC AGTTGAGAAG GATACGTTGA TGGTGGACGT      1080

TGAAGGATCC ACAACACTCT CTAACAGGCG TTACAACTGC TGGTCTACGT TTAAAGACCT      1140
```

```
TGATCGTGAA TCATGCAAGG GTGTTTATGA TAACATTAGC AAGAACGCCT TGTTAGTTTA    1200

TTATTGCTGG ATGTCTGACA CGCCTGCGAA TGCATCCTCT TTTGTATCTT TTGATCTTGA    1260

TTATATTGGT TAACTTAACG AAGTGTGTTT GTCTAAAGAT GATTAAAAAA ATGAAAATGT    1320

AAAAATAAAA TTTTATTTTA ATGGTTTCGT CTGAGACGCC TTACAATTAC TATTAATACA    1380

TTCATGGACC GTAGTCCGTA TTAATTCATT CAACTGTCCC ATAGACATTG TAATGTTGGA    1440

CTCTGTTCTC TGGGCCCCCA CAATAGAAGC AGACTCTCCC GGGTCCAGTA TGCCTGTTCC    1500

TAGCCTGTTT AGATGTCTGT ACGGGTGGAG TTCGTTCTCC ACATCTGAGT CCGCATCTGA    1560

ATGCCCTATG CCTATTGTAC TCCTTGAAGC CCATGACTCA CCAGGCCTGA TCTCAATTGG    1620

ACCTCTAAGC CCAAGTCTGG ACATGGACGC GCATCTAATG GCTTCCTCT CCCATTTACC     1680

GTAATCCACA TGGGAAAAGT CCACATCTTT ATCTGTGAAC TGTTTGGACA GGATTTTTAC    1740

TGTTGGTGCC CGGAAGGGGA TGTCTACTGA GTGTTTTGCT GTGGACAATT TCAGCTTCCC    1800

CTTAAACTTG GCGAAGTGGG TCCGTTGATG AACATTCGTA TCGCAAACCC TGTAATACAA    1860

TTTCCATGGA ATTGGGTCTT TCAAGGAGAA GAAGGAAGCT GAGAAATAGT GGAGATCTAT    1920

GTTGCACCTG ATCGGAAATG TCCATGATGC CTGTAAAGAC TCATTCTCCG TCATTCTTTT    1980

GTCGTGAATC TCCACTATTA CCGACCCAGT GGCGTTTATT GGTACTTGTT GTCTGTACTC    2040

TATGACACAG TGGTCGATTT TCATGCAGCT ACGGCTGAGC CTAGCGGTTA ACTGCGACGC    2100

CGTGGACGGA AATTGCAGTA TTATTTCAGT TAGGTCATGA GAAAGCTGAT ATTCGTCACG    2160

GTGTGCATCT ATGTAGTTGA ATGCGCTAGG AGGATTAACT AACTGAGAAT CCATATGAAG    2220

AAAATAAGGC CGCGCAGGAC TGATTGCTGA AGTTGAATCA GAAAGAAGTC GAACAAGCTA    2280

TGAAACGGCA GTTTCGAACT CGAAGAAGAA AGACAGCCAA CTATATTTTC TTTTTTCCAA    2340

GAATTCAGCT GTGCTGAATA TAAAGTTTAT GAAGAGCGGA AATGAAAAAA AGTATATCAG    2400

GATTCGAAGT GTTTGAGAAA GAAAAGAAAT ATGAAAGAGA ATTTTGGAGA AATTTGAGTA    2460

AGAAGGAATT TGTATATGAA CTAAGAAACC TAGGGTTGAT GGGTATTTAA ATTGGTAAAG    2520

TGTTCATCCC ATGAGATAGA                                               2540
```

(2) INFORMATION FOR SEQ ID NO:19:

(i) SEQUENCE CHARACTERISTICS:
        (A) LENGTH: 1145 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (iv) ANTI-SENSE: NO (v) FRAGMENT TYPE: N-terminal (vi) ORIGINAL SOURCE:
        (A) ORGANISM: Tomato Yellow Leaf Curl Virus
        (B) STRAIN: Israel (ix) FEATURE:
        (A) NAME/KEY: CDS
        (B) LOCATION: 37..1107

(x) PUBLICATION INFORMATION:
        (A) AUTHORS: Navot, N
               Pichersky, R
               Zeidan, D
               Zamir, D
               Czosnek, H (B) TITLE: Tomato yellow leaf curl virus: A
    whitefly-transmitted geminivirus with a single
    genomic component.
(C) JOURNAL: Virology
(D) VOLUME: 185
(F) PAGES: 151-168
(G) DATE: 1991

(xi) SEQUENCE DESCRIPTION: SEQ ID NO:19:

```
GCCATAGAGC TTTGAGGGAT CCCGATTCAT TTCAAC ATG CCT CGT TTA TTT AAA           54
                                           Met Pro Arg Leu Phe Lys
                                           1               5

ATA TAT GCC AAA AAT TAT TTC CTA ACA TAT CCC AAT TGT TCT CTC TCT          102
Ile Tyr Ala Lys Asn Tyr Phe Leu Thr Tyr Pro Asn Cys Ser Leu Ser
        10              15              20

AAA GAG GAA GCA CTT TCC CAA TTA AAA AAA CTA GAA ACC CCA ACA AAT          150
Lys Glu Glu Ala Leu Ser Gln Leu Lys Lys Leu Glu Thr Pro Thr Asn
    25              30              35

AAA AAA TAC ATC AAA GTT TGC AAA GAA CTC CAC GAG AAT GGG GAA CCA          198
Lys Lys Tyr Ile Lys Val Cys Lys Glu Leu His Glu Asn Gly Glu Pro
40              45              50

CAT CTC CAT GTG CTT ATC CAA TTC GAA GGC AAA TAC CAA TGT AAG AAC          246
His Leu His Val Leu Ile Gln Phe Glu Gly Lys Tyr Gln Cys Lys Asn
55              60              65              70

CAA CGG TTC TTC GAC TTG GTA TCC CCA AAC AGG TCA GCA CAT TTC CAT          294
Gln Arg Phe Phe Asp Leu Val Ser Pro Asn Arg Ser Ala His Phe His
            75              80              85

CCG AAC ATT CAG GCA GCT AAG AGC TCA ACA GAT GTC AAG ACC TAC GTG          342
Pro Asn Ile Gln Ala Ala Lys Ser Ser Thr Asp Val Lys Thr Tyr Val
        90              95              100

GAG AAA GAC GGA AAC TTC ATT GAT TTT GGA GTT TCC CAA ATC GAT GGC          390
Glu Lys Asp Gly Asn Phe Ile Asp Phe Gly Val Ser Gln Ile Asp Gly
    105             110             115

AGA TCA GCT AGA GGA GGT CAG CAA TCT GCC AAC GAC GCA TAT GCC GAA          438
Arg Ser Ala Arg Gly Gly Gln Gln Ser Ala Asn Asp Ala Tyr Ala Glu
120             125             130

GCA CTC AAT TCA GGC AGT ATA TCC GAG GCC CTC AAT ATA TTA AAA GAG          486
Ala Leu Asn Ser Gly Ser Ile Ser Glu Ala Leu Asn Ile Leu Lys Glu
135             140             145             150

AAG GCC CCA AAG GAC TAT ATT TTA CAA TTT CAT AAT TTA AGT TCA AAT          534
Lys Ala Pro Lys Asp Tyr Ile Leu Gln Phe His Asn Leu Ser Ser Asn
            155             160             165

TTA GAT AGG ATT TTT AGT CCT CCT TTA GAA GTT TAT GTT TCT CCA TTT          582
Leu Asp Arg Ile Phe Ser Pro Pro Leu Glu Val Tyr Val Ser Pro Phe
        170             175             180

CTT TCT TCT TCT TTT AAT CAA GTT CCA GAT GAA CTT GAA GAG TGG GTC          630
Leu Ser Ser Ser Phe Asn Gln Val Pro Asp Glu Leu Glu Glu Trp Val
    185             190             195

GCC GAG AAC GTC GTG TAT TCC GCT GCG CGG CCA TGG AGA CCC ATA AGT          678
Ala Glu Asn Val Val Tyr Ser Ala Ala Arg Pro Trp Arg Pro Ile Ser
200             205             210

ATT GTC ATT GAG GGT GAT AGC AGA ACA GGC AAA ACA ATG TGG GCC AGG          726
Ile Val Ile Glu Gly Asp Ser Arg Thr Gly Lys Thr Met Trp Ala Arg
215             220             225             230

TCT CTA GGC CCA CAT AAT TAT TTA TGT GGA CAT CTA GAC CTA AGC CCA          774
Ser Leu Gly Pro His Asn Tyr Leu Cys Gly His Leu Asp Leu Ser Pro
            235             240             245

AAG GTG TAC AGT AAT GAT GCG TGG TAC AAC GTC ATT GAT GAC GTA AAC          822
Lys Val Tyr Ser Asn Asp Ala Trp Tyr Asn Val Ile Asp Asp Val Asn
        250             255             260

CCG CAT TAT TTA AAG CAC TTC AAG GAA TTC ATT TGG GCC AGG GGA GAC          870
Pro His Tyr Leu Lys His Phe Lys Glu Phe Ile Trp Ala Arg Gly Asp
```

```
                                                                              918
Pro His Tyr Leu Lys His Phe Lys Glu Phe Ile Trp Ala Gln Arg Asp
        265                 270                 275
TGG CAA AGC AAC ACA AAG TAC GGG AAG CCC ATT CAA ATT AAA GGG GGA              918
Trp Gln Ser Asn Thr Lys Tyr Gly Lys Pro Ile Gln Ile Lys Gly Gly
        280                 285                 290

ATT CCC ACT ATC TTC CTC TGC AAT CCA GGA CCT ACC TCC TCA TAT AGG              966
Ile Pro Thr Ile Phe Leu Cys Asn Pro Gly Pro Thr Ser Ser Tyr Arg
295             300                 305                 310

GAA TAT CTA GAC GAA GAA AAA AAC ATA TCC TTG AAA AAT TGG GCT CTC              1014
Glu Tyr Leu Asp Glu Glu Lys Asn Ile Ser Leu Lys Asn Trp Ala Leu
                315                 320                 325

AAG AAT GCA ACC TTC GTC ACC CTC TAC GAG CCA CTG TTC GCA AGT ATC              1062
Lys Asn Ala Thr Phe Val Thr Leu Tyr Glu Pro Leu Phe Ala Ser Ile
            330                 335                 340

AAT CAA GGT CCA ACA CAA GAT AGC CAA GAA GAA ACC AAT AAG GCG                  1107
Asn Gln Gly Pro Thr Gln Asp Ser Gln Glu Glu Thr Asn Lys Ala
        345                 350                 355

TAAGCGTGTA GACCTAGACT GTGGCTGCTC ATACTACC                                    1145
```

(2) INFORMATION FOR SEQ ID NO:20:

(i) SEQUENCE CHARACTERISTICS:
        (A) LENGTH: 357 amino acids
        (B) TYPE: amino acid
        (D) TOPOLOGY: linear (ii) MOLECULE TYPE: protein (xi) SEQUENCE DESCRIPTION: SEQ ID NO:20:

```
Met Pro Arg Leu Phe Lys Ile Tyr Ala Lys Asn Tyr Phe Leu Thr Tyr
1               5                   10                  15

Pro Asn Cys Ser Leu Ser Lys Glu Glu Ala Leu Ser Gln Leu Lys Lys
                20                  25                  30

Leu Glu Thr Pro Thr Asn Lys Lys Tyr Ile Lys Val Cys Lys Glu Leu
            35                  40                  45

His Glu Asn Gly Glu Pro His Leu His Val Leu Ile Gln Phe Glu Gly
        50                  55                  60

Lys Tyr Gln Cys Lys Asn Gln Arg Phe Phe Asp Leu Val Ser Pro Asn
65                  70                  75                  80

Arg Ser Ala His Phe His Pro Asn Ile Gln Ala Ala Lys Ser Ser Thr
                85                  90                  95

Asp Val Lys Thr Tyr Val Glu Lys Asp Gly Asn Phe Ile Asp Phe Gly
                100                 105                 110

Val Ser Gln Ile Asp Gly Arg Ser Ala Arg Gly Gly Gln Gln Ser Ala
            115                 120                 125

Asn Asp Ala Tyr Ala Glu Ala Leu Asn Ser Gly Ser Ile Ser Glu Ala
        130                 135                 140

Leu Asn Ile Leu Lys Glu Lys Ala Pro Lys Asp Tyr Ile Leu Gln Phe
145                 150                 155                 160

His Asn Leu Ser Ser Asn Leu Asp Arg Ile Phe Ser Pro Pro Leu Glu
                165                 170                 175

Val Tyr Val Ser Pro Phe Leu Ser Ser Ser Phe Asn Gln Val Pro Asp
                180                 185                 190

Glu Leu Glu Glu Trp Val Ala Glu Asn Val Val Tyr Ser Ala Ala Arg
            195                 200                 205

Pro Trp Arg Pro Ile Ser Ile Val Ile Glu Gly Asp Ser Arg Thr Gly
        210                 215                 220
```

```
Lys Thr Met Trp Ala Arg Ser Leu Gly Pro His Asn Tyr Leu Cys Gly
225                 230                 235                 240

His Leu Asp Leu Ser Pro Lys Val Tyr Ser Asn Asp Ala Trp Tyr Asn
                245                 250                 255

Val Ile Asp Asp Val Asn Pro His Tyr Leu Lys His Phe Lys Glu Phe
                260                 265                 270

Ile Trp Ala Gln Arg Asp Trp Gln Ser Asn Thr Lys Tyr Gly Lys Pro
            275                 280                 285

Ile Gln Ile Lys Gly Gly Ile Pro Thr Ile Phe Leu Cys Asn Pro Gly
        290                 295                 300

Pro Thr Ser Ser Tyr Arg Glu Tyr Leu Asp Glu Lys Asn Ile Ser
305                 310                 315                 320

Leu Lys Asn Trp Ala Leu Lys Asn Ala Thr Phe Val Thr Leu Tyr Glu
                325                 330                 335

Pro Leu Phe Ala Ser Ile Asn Gln Gly Pro Thr Gln Asp Ser Gln Glu
                340                 345                 350

Glu Thr Asn Lys Ala
        355
```

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (iv) ANTI-SENSE: NO (vi) ORIGINAL SOURCE:
        (A) ORGANISM: PTYIRC4

(xi) SEQUENCE DESCRIPTION: SEQ ID NO:21:

GCCATAGAGC TTTGAGGGAT CCCGATTCAT TTC                                      33

(2) INFORMATION FOR SEQ ID NO:22:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (iv) ANTI-SENSE: NO (vi) ORIGINAL SOURCE:
        (A) ORGANISM: PTYC1V1679

(xi) SEQUENCE DESCRIPTION: SEQ ID NO:22:

GGTAGTATGA GGATCCACAG TCTAGGTCTA CACGCTTAC                              39

(2) INFORMATION FOR SEQ ID NO:23:

(i) SEQUENCE CHARACTERISTICS:
        (A) LENGTH: 1145 base pairs
        (B) TYPE: nucleic acid

```
          (C) STRANDEDNESS: single
          (D) TOPOLOGY: circular (ii) MOLECULE TYPE: DNA (genomic)

(iii) HYPOTHETICAL: NO (iv) ANTI-SENSE: NO (vi) ORIGINAL SOURCE:
          (A) ORGANISM: Tomato Yellow Leaf Curl Geminivirus
          (B) STRAIN: Israel (ix) FEATURE:
          (A) NAME/KEY: CDS
          (B) LOCATION: 37..1107

(xi) SEQUENCE DESCRIPTION: SEQ ID NO:23:

GCCATAGAGC TTTGAGGGAT CCCGATTCAT TTCAAC ATG CCT CGT TTA TTT AAA          54
                                         Met Pro Arg Leu Phe Lys
                                          1               5

ATA TAT GCC AAA AAT TAT TTC CTA ACA TAT CCC AAT TGT TCT CTC TCT         102
Ile Tyr Ala Lys Asn Tyr Phe Leu Thr Tyr Pro Asn Cys Ser Leu Ser
         10                  15                  20

AAA GAG GAA GCA CTT TCC CAA TTA AAA AAA CTA GAA ACC CCA ACA AAT         150
Lys Glu Glu Ala Leu Ser Gln Leu Lys Lys Leu Glu Thr Pro Thr Asn
     25                  30                  35

AAA AAA TAC ATC AAA GTT TGC AAA GAA CTC CAC GAG AAT GGG GAA CCA         198
Lys Lys Tyr Ile Lys Val Cys Lys Glu Leu His Glu Asn Gly Glu Pro
 40                  45                  50

CAT CTC CAT GTG CTT ATC CAA TTC GAA GGC AAA TAC CAA TGT AAG AAC         246
His Leu His Val Leu Ile Gln Phe Glu Gly Lys Tyr Gln Cys Lys Asn
 55                  60                  65                  70

CAA CGG TTC TTC GAC TTG GTA TCC CCA AAC AGG TCA GCA CAT TTC CAT         294
Gln Arg Phe Phe Asp Leu Val Ser Pro Asn Arg Ser Ala His Phe His
             75                  80                  85

CCG AAC ATT CAG GCA GCT AAG AGC TCA ACA GAT GTC AAG ACC TAC GTG         342
Pro Asn Ile Gln Ala Ala Lys Ser Ser Thr Asp Val Lys Thr Tyr Val
             90                  95                 100

GAG CGA GAC GGA AAC TTC ATT GAT TTT GGA GTT TCC CAA ATC GAT GGC         390
Glu Arg Asp Gly Asn Phe Ile Asp Phe Gly Val Ser Gln Ile Asp Gly
            105                 110                 115

AGA TCA GCT AGA GGA GGT CAG CAA TCT GCC AAC GAC GCA TAT GCC GAA         438
Arg Ser Ala Arg Gly Gly Gln Gln Ser Ala Asn Asp Ala Tyr Ala Glu
        120                 125                 130

GCA CTC AAT TCA GGC AGT AAA TCC GAG GCC CTC AAT ATA TTA AAA GAG         486
Ala Leu Asn Ser Gly Ser Lys Ser Glu Ala Leu Asn Ile Leu Lys Glu
135                 140                 145                 150

AAG GCC CCA AAG GAC TAT ATT TTA CAA TTT CAT AAT TTA AGT TCA AAT         534
Lys Ala Pro Lys Asp Tyr Ile Leu Gln Phe His Asn Leu Ser Ser Asn
                155                 160                 165

TTA GAT AGG ATT TTT AGT CCT CCT TTA GAA GTT TAT GTT TCT CCA TTT         582
Leu Asp Arg Ile Phe Ser Pro Pro Leu Glu Val Tyr Val Ser Pro Phe
            170                 175                 180

CTT TCT TCT TCT TTT AAT CAA GTT CCA GAT GAA CTT GAA GAG TGG GTC         630
Leu Ser Ser Ser Phe Asn Gln Val Pro Asp Glu Leu Glu Glu Trp Val
        185                 190                 195

GCC GAG AAC GTC GTG TAT TCC GCT GCG CGG CCA TGG AGA CCC ATA AGT         678
Ala Glu Asn Val Val Tyr Ser Ala Ala Arg Pro Trp Arg Pro Ile Ser
    200                 205                 210

ATT GTC ATT GAG GGT GAT AGC AGA ACA GGC AAA ACA ATG TGG GCC AGG         726
Ile Val Ile Glu Gly Asp Ser Arg Thr Gly Lys Thr Met Trp Ala Arg
215                 220                 225                 230
```

```
TCT CTA GGC CCA CAT AAT TAT TTA TGT GGA CAT CTA GAC CTA AGC CCA    774
Ser Leu Gly Pro His Asn Tyr Leu Cys Gly His Leu Asp Leu Ser Pro
                235                 240                 245

AAG GTG TAC AGT AAT GAT GCG TGG TAC AAC GTC ATT GAT GAC GTA GAC    822
Lys Val Tyr Ser Asn Asp Ala Trp Tyr Asn Val Ile Asp Asp Val Asp
            250                 255                 260

CCG CAT TAT TTA AAG CAC TTC AAG GAA TTC ATG GGG GCC CAG AGG GAC    870
Pro His Tyr Leu Lys His Phe Lys Glu Phe Met Gly Ala Gln Arg Asp
                265                 270                 275

TGG CAA AGC AAC ACA AAG TAC GGG AAG CCC ATT CAA ATT AAA GGG GGA    918
Trp Gln Ser Asn Thr Lys Tyr Gly Lys Pro Ile Gln Ile Lys Gly Gly
    280                 285                 290

ATT CCC ACT ATC TTC CTC TGC AAT CCA GGA CCT ACC TCC TCA TAT AGG    966
Ile Pro Thr Ile Phe Leu Cys Asn Pro Gly Pro Thr Ser Ser Tyr Arg
295                 300                 305                 310

GAA TAT CTA GAC GAA GAA AAA AAC ATA TCC TTG AAA AAT TGG GCT CTC   1014
Glu Tyr Leu Asp Glu Glu Lys Asn Ile Ser Leu Lys Asn Trp Ala Leu
                315                 320                 325

AAG AAT GCA ACC TTC GTC ACC CTC TAC GAG CCA CTG TTC GCA AGT ATC   1062
Lys Asn Ala Thr Phe Val Thr Leu Tyr Glu Pro Leu Phe Ala Ser Ile
            330                 335                 340

AAT CAA GGT CCA ACA CAA GAT AGC CAA GAA GAA ACC AAT AAG GCG       1107
Asn Gln Gly Pro Thr Gln Asp Ser Gln Glu Glu Thr Asn Lys Ala
                345                 350                 355

TAAGCGTGTA GACCTAGACT GTGGCTGCTC ATACTACC                         1145

(2) INFORMATION FOR SEQ ID NO:24:

(i) SEQUENCE CHARACTERISTICS:
        (A) LENGTH: 357 amino acids
        (B) TYPE: amino acid
        (D) TOPOLOGY: linear (ii) MOLECULE TYPE: protein (xi) SEQUENCE DESCRIPTION: SEQ ID NO:24:

Met Pro Arg Leu Phe Lys Ile Tyr Ala Lys Asn Tyr Phe Leu Thr Tyr
 1               5                  10                  15

Pro Asn Cys Ser Leu Ser Lys Glu Glu Ala Leu Ser Gln Leu Lys Lys
                20                  25                  30

Leu Glu Thr Pro Thr Asn Lys Lys Tyr Ile Lys Val Cys Lys Glu Leu
            35                  40                  45

His Glu Asn Gly Glu Pro His Leu His Val Leu Ile Gln Phe Glu Gly
        50                  55                  60

Lys Tyr Gln Cys Lys Asn Gln Arg Phe Phe Asp Leu Val Ser Pro Asn
65                  70                  75                  80

Arg Ser Ala His Phe His Pro Asn Ile Gln Ala Ala Lys Ser Ser Thr
                85                  90                  95

Asp Val Lys Thr Tyr Val Glu Arg Asp Gly Asn Phe Ile Asp Phe Gly
            100                 105                 110

Val Ser Gln Ile Asp Gly Arg Ser Ala Arg Gly Gly Gln Gln Ser Ala
        115                 120                 125

Asn Asp Ala Tyr Ala Glu Ala Leu Asn Ser Gly Ser Lys Ser Glu Ala
    130                 135                 140

Leu Asn Ile Leu Lys Glu Lys Ala Pro Lys Asp Tyr Ile Leu Gln Phe
145                 150                 155                 160

His Asn Leu Ser Ser Asn Leu Asp Arg Ile Phe Ser Pro Pro Leu Glu
                165                 170                 175
```

Val Tyr Val Ser Pro Phe Leu Ser Ser Ser Phe Asn Gln Val Pro Asp
            180                 185                 190

Glu Leu Glu Glu Trp Val Ala Glu Asn Val Val Tyr Ser Ala Ala Arg
            195                 200                 205

Pro Trp Arg Pro Ile Ser Ile Val Ile Glu Gly Asp Ser Arg Thr Gly
            210                 215                 220

Lys Thr Met Trp Ala Arg Ser Leu Gly Pro His Asn Tyr Leu Cys Gly
225                 230                 235                 240

His Leu Asp Leu Ser Pro Lys Val Tyr Ser Asn Asp Ala Trp Tyr Asn
                245                 250                 255

Val Ile Asp Asp Val Asp Pro His Tyr Leu Lys His Phe Lys Glu Phe
            260                 265                 270

Met Gly Ala Gln Arg Asp Trp Gln Ser Asn Thr Lys Tyr Gly Lys Pro
            275                 280                 285

Ile Gln Ile Lys Gly Gly Ile Pro Thr Ile Phe Leu Cys Asn Pro Gly
            290                 295                 300

Pro Thr Ser Ser Tyr Arg Glu Tyr Leu Asp Glu Glu Lys Asn Ile Ser
305                 310                 315                 320

Leu Lys Asn Trp Ala Leu Lys Asn Ala Thr Phe Val Thr Leu Tyr Glu
                325                 330                 335

Pro Leu Phe Ala Ser Ile Asn Gln Gly Pro Thr Gln Asp Ser Gln Glu
            340                 345                 350

Glu Thr Asn Lys Ala
            355

(2) INFORMATION FOR SEQ ID NO:25:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (iv) ANTI-SENSE: NO (vi) ORIGINAL SOURCE:
        (A) ORGANISM: C1V2467

(xi) SEQUENCE DESCRIPTION: SEQ ID NO:25:

GTTTCCGTCT CGCTCCACGT AGG                                           23

(2) INFORMATION FOR SEQ ID NO:26:

(i) SEQUENCE CHARACTERISTICS:
        (A) LENGTH: 1145 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (iv) ANTI-SENSE: NO (v) FRAGMENT TYPE: N-terminal (vi) ORIGINAL SOURCE:
        (A) ORGANISM: Tomato Yellow Leaf Curl Virus
        (B) STRAIN: Israel

```
    (ix) FEATURE:
         (A) NAME/KEY: CDS
         (B) LOCATION: 37..1107

(x) PUBLICATION INFORMATION:
         (A) AUTHORS: Navot, N
                      Pichersky, R
                      Zeidan, D
                      Zamir, D
                      Czosnek, H
         (B) TITLE: Tomato yellow leaf curl virus:  A
                    whitefly-transmitted geminivirus with a single
                    genomic component.
         (C) JOURNAL: Virology
         (D) VOLUME: 185
         (F) PAGES: 151-168
         (G) DATE: 1991

(xi) SEQUENCE DESCRIPTION: SEQ ID NO:26:

GCCATAGAGC TTTGAGGGAT CCCGATTCAT TCAAC ATG CCT CGT TTA TTT AAA          54
                                       Met Pro Arg Leu Phe Lys
                                         1               5

ATA TAT GCC AAA AAT TAT TTC CTA ACA TAT CCC AAT TGT TCT CTC TCT        102
Ile Tyr Ala Lys Asn Tyr Phe Leu Thr Tyr Pro Asn Cys Ser Leu Ser
         10                  15                  20

AAA GAG GAA GCA CTT TCC CAA TTA AAA AAA CTA GAA ACC CCA ACA AAT        150
Lys Glu Glu Ala Leu Ser Gln Leu Lys Lys Leu Glu Thr Pro Thr Asn
             25                  30                  35

AAA AAA TAC ATC AAA GTT TGC AAA GAA CTC CAC GAG AAT GGG GAA CCA        198
Lys Lys Tyr Ile Lys Val Cys Lys Glu Leu His Glu Asn Gly Glu Pro
 40                  45                  50

CAT CTC CAT GTG CTT ATC CAA TTC GAA GGC AAA TAC CAA TGT AAG AAC        246
His Leu His Val Leu Ile Gln Phe Glu Gly Lys Tyr Gln Cys Lys Asn
 55                  60                  65                  70

CAA CGG TTC TTC GAC TTG GTA TCC CCA AAC AGG TCA GCA CAT TTC CAT        294
Gln Arg Phe Phe Asp Leu Val Ser Pro Asn Arg Ser Ala His Phe His
             75                  80                  85

CCG AAC ATT CAG GCA GCT AAG AGC TCA ACA GAT GTC AAG ACC TAC GTG        342
Pro Asn Ile Gln Ala Ala Lys Ser Ser Thr Asp Val Lys Thr Tyr Val
             90                  95                 100

GAG AAA GAC GGA AAC TTC ATT GAT TTT GGA GTT TCC CAA ATC GAT GGC        390
Glu Lys Asp Gly Asn Phe Ile Asp Phe Gly Val Ser Gln Ile Asp Gly
            105                 110                 115

AGA TCA GCT AGA GGA GGT CAG CAA TCT GCC AAC GAC GCA TAT GCC GAA        438
Arg Ser Ala Arg Gly Gly Gln Gln Ser Ala Asn Asp Ala Tyr Ala Glu
120                 125                 130

GCA CTC AAT TCA GGC AGT AAA TCC GAG GCC CTC AAT ATA TTA AAA GAG        486
Ala Leu Asn Ser Gly Ser Lys Ser Glu Ala Leu Asn Ile Leu Lys Glu
135                 140                 145                 150

AAG GCC CCA AAG GAC TAT ATT TTA CAA TTT CAT AAT TTA AGT TCA AAT        534
Lys Ala Pro Lys Asp Tyr Ile Leu Gln Phe His Asn Leu Ser Ser Asn
                155                 160                 165

TTA GAT AGG ATT TTT AGT CCT CCT TTA GAA GTT TAT GTT TCT CCA TTT        582
Leu Asp Arg Ile Phe Ser Pro Pro Leu Glu Val Tyr Val Ser Pro Phe
            170                 175                 180

CTT TCT TCT TCT TTT AAT CAA GTT CCA GAT GAA CTT GAA GAG TGG GTC        630
Leu Ser Ser Ser Phe Asn Gln Val Pro Asp Glu Leu Glu Glu Trp Val
            185                 190                 195

GCC GAG AAC GTC GTG TAT TCC GCT GCG CGG CCA TGG AGA CCC ATA AGT        678
Ala Glu Asn Val Val Tyr Ser Ala Ala Arg Pro Trp Arg Pro Ile Ser
200                 205                 210

ATT GTC ATT GAG GGT GAT AGC AGA ACA GGC GCA ACA ATG TGG GCC AGG        726
Ile Val Ile Glu Gly Asp Ser Arg Thr Gly Ala Thr Met Trp Ala Arg
```

```
                215                 220                 225                 230
TCT CTA GGC CCA CAT AAT TAT TTA TGT GGA CAT CTA GAC CTA AGC CCA         774
Ser Leu Gly Pro His Asn Tyr Leu Cys Gly His Leu Asp Leu Ser Pro
                    235                 240                 245

AAG GTG TAC AGT AAT GAT GCG TGG TAC AAC GTC ATT GAT GAC GTA GAC         822
Lys Val Tyr Ser Asn Asp Ala Trp Tyr Asn Val Ile Asp Asp Val Asp
                250                 255                 260

CCG CAT TAT TTA AAG CAC TTC AAG GAA TTC ATG GGG GCC CAG AGG GAC         870
Pro His Tyr Leu Lys His Phe Lys Glu Phe Met Gly Ala Gln Arg Asp
                265                 270                 275

TGG CAA AGC AAC ACA AAG TAC GGG AAG CCC ATT CAA ATT AAA GGG GGA         918
Trp Gln Ser Asn Thr Lys Tyr Gly Lys Pro Ile Gln Ile Lys Gly Gly
            280                 285                 290

ATT CCC ACT ATC TTC CTC TGC AAT CCA GGA CCT ACC TCC TCA TAT AGG         966
Ile Pro Thr Ile Phe Leu Cys Asn Pro Gly Pro Thr Ser Ser Tyr Arg
295                 300                 305                 310

GAA TAT CTA GAC GAA GAA AAA AAC ATA TCC TTG AAA AAT TGG GCT CTC         1014
Glu Tyr Leu Asp Glu Glu Lys Asn Ile Ser Leu Lys Asn Trp Ala Leu
                315                 320                 325

AAG AAT GCA ACC TTC GTC ACC CTC TAC GAG CCA CTG TTC GCA AGT ATC         1062
Lys Asn Ala Thr Phe Val Thr Leu Tyr Glu Pro Leu Phe Ala Ser Ile
                330                 335                 340

AAT CAA GGT CCA ACA CAA GAT AGC CAA GAA GAA ACC AAT AAG GCG             1107
Asn Gln Gly Pro Thr Gln Asp Ser Gln Glu Glu Thr Asn Lys Ala
            345                 350                 355

TAAGCGTGTA GACCTAGACT GTGGCTGCTC ATACTACC                               1145

(2) INFORMATION FOR SEQ ID NO:27:

(i) SEQUENCE CHARACTERISTICS:
        (A) LENGTH: 357 amino acids
        (B) TYPE: amino acid
        (D) TOPOLOGY: linear (ii) MOLECULE TYPE: protein (xi) SEQUENCE DESCRIPTION: SEQ ID NO:27:

Met Pro Arg Leu Phe Lys Ile Tyr Ala Lys Asn Tyr Phe Leu Thr Tyr
 1               5                  10                  15

Pro Asn Cys Ser Leu Ser Lys Glu Glu Ala Leu Ser Gln Leu Lys Lys
            20                  25                  30

Leu Glu Thr Pro Thr Asn Lys Lys Tyr Ile Lys Val Cys Lys Glu Leu
        35                  40                  45

His Glu Asn Gly Glu Pro His Leu His Val Leu Ile Gln Phe Glu Gly
    50                  55                  60

Lys Tyr Gln Cys Lys Asn Gln Arg Phe Phe Asp Leu Val Ser Pro Asn
65                  70                  75                  80

Arg Ser Ala His Phe His Pro Asn Ile Gln Ala Ala Lys Ser Ser Thr
                85                  90                  95

Asp Val Lys Thr Tyr Val Glu Lys Asp Gly Asn Phe Ile Asp Phe Gly
            100                 105                 110

Val Ser Gln Ile Asp Gly Arg Ser Ala Arg Gly Gly Gln Gln Ser Ala
        115                 120                 125

Asn Asp Ala Tyr Ala Glu Ala Leu Asn Ser Gly Ser Lys Ser Glu Ala
    130                 135                 140

Leu Asn Ile Leu Lys Glu Lys Ala Pro Lys Asp Tyr Ile Leu Gln Phe
145                 150                 155                 160

His Asn Leu Ser Ser Asn Leu Asp Arg Ile Phe Ser Pro Pro Leu Glu
```

```
                165                 170                 175
Val Tyr Val Ser Pro Phe Leu Ser Ser Phe Asn Gln Val Pro Asp
                180                 185                 190

Glu Leu Glu Glu Trp Val Ala Glu Asn Val Val Tyr Ser Ala Ala Arg
            195                 200                 205

Pro Trp Arg Pro Ile Ser Ile Val Ile Glu Gly Asp Ser Arg Thr Gly
    210                 215                 220

Ala Thr Met Trp Ala Arg Ser Leu Gly Pro His Asn Tyr Leu Cys Gly
225                 230                 235                 240

His Leu Asp Leu Ser Pro Lys Val Tyr Ser Asn Asp Ala Trp Tyr Asn
                245                 250                 255

Val Ile Asp Asp Val Asp Pro His Tyr Leu Lys His Phe Lys Glu Phe
            260                 265                 270

Met Gly Ala Gln Arg Asp Trp Gln Ser Asn Thr Lys Tyr Gly Lys Pro
        275                 280                 285

Ile Gln Ile Lys Gly Gly Ile Pro Thr Ile Phe Leu Cys Asn Pro Gly
290                 295                 300

Pro Thr Ser Ser Tyr Arg Glu Tyr Leu Asp Glu Lys Asn Ile Ser
305                 310                 315                 320

Leu Lys Asn Trp Ala Leu Lys Asn Ala Thr Phe Val Thr Leu Tyr Glu
            325                 330                 335

Pro Leu Phe Ala Ser Ile Asn Gln Gly Pro Thr Gln Asp Ser Gln Glu
            340                 345                 350

Glu Thr Asn Lys Ala
        355

(2) INFORMATION FOR SEQ ID NO:28:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (iv) ANTI-SENSE: NO (vi) ORIGINAL SOURCE:
        (A) ORGANISM: C1V2101

(xi) SEQUENCE DESCRIPTION: SEQ ID NO:28:

GGCCCACATT GTTGCGCCTG TTCTGC                                      26

(2) INFORMATION FOR SEQ ID NO:29:

(i) SEQUENCE CHARACTERISTICS:
        (A) LENGTH: 1145 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (iv) ANTI-SENSE: NO (v) FRAGMENT TYPE: N-terminal (vi) ORIGINAL SOURCE:
```

(A) ORGANISM: Tomato Yellow Leaf Curl Virus
        (B) STRAIN: Israel (ix) FEATURE:
        (A) NAME/KEY: CDS
        (B) LOCATION: 37..1107

(x) PUBLICATION INFORMATION:
        (A) AUTHORS: Navot, N
            Pichersky, R
            Zeidan, D
            Zamir, D
            Czosnek, H
        (B) TITLE: Tomato yellow leaf curl virus: A
            whitefly-transmitted geminivirus with a single
            genomic component.
        (C) JOURNAL: Virology
        (D) VOLUME: 185
        (F) PAGES: 151-168
        (G) DATE: 1991

(xi) SEQUENCE DESCRIPTION: SEQ ID NO:29:

```
GCCATAGAGC TTTGAGGGAT CCCGATTCAT TCAAC ATG CCT CGT TTA TTT AAA           54
                                      Met Pro Arg Leu Phe Lys
                                       1               5

ATA TAT GCC AAA AAT TAT TTC CTA ACA TAT CCC AAT TGT TCT CTC TCT         102
Ile Tyr Ala Lys Asn Tyr Phe Leu Thr Tyr Pro Asn Cys Ser Leu Ser
         10                  15                  20

AAA GAG GAA GCA CTT TCC CAA TTA AAA AAA CTA GAA ACC CCA ACA AAT         150
Lys Glu Glu Ala Leu Ser Gln Leu Lys Lys Leu Glu Thr Pro Thr Asn
     25                  30                  35

AAA AAA TAC ATC AAA GTT TGC AAA GAA CTC CAC GAG AAT GGG GAA CCA         198
Lys Lys Tyr Ile Lys Val Cys Lys Glu Leu His Glu Asn Gly Glu Pro
 40                  45                  50

CAT CTC CAT GTG CTT ATC CAA TTC GAA GGC AAA TAC CAA TGT AAG AAC         246
His Leu His Val Leu Ile Gln Phe Glu Gly Lys Tyr Gln Cys Lys Asn
 55                  60                  65                  70

CAA CGG TTC TTC GAC TTG GTA TCC CCA AAC AGG TCA GCA CAT TTC CAT         294
Gln Arg Phe Phe Asp Leu Val Ser Pro Asn Arg Ser Ala His Phe His
             75                  80                  85

CCG AAC ATT CAG GCA GCT AAG AGC TCA ACA GAT GTC AAG ACC TAC GTG         342
Pro Asn Ile Gln Ala Ala Lys Ser Ser Thr Asp Val Lys Thr Tyr Val
                 90                  95                 100

GAG AAA GAC GGA AAC TTC ATT GAT TTT GGA GTT TCC CAA ATC GAT GGC         390
Glu Lys Asp Gly Asn Phe Ile Asp Phe Gly Val Ser Gln Ile Asp Gly
            105                 110                 115

AGA TCA GCT AGA GGA GGT CAG CAA TCT GCC AAC GAC GCA TAT GCC GAA         438
Arg Ser Ala Arg Gly Gly Gln Gln Ser Ala Asn Asp Ala Tyr Ala Glu
        120                 125                 130

GCA CTC AAT TCA GGC AGT AAA TCC GAG GCC CTC AAT ATA TTA AAA GAG         486
Ala Leu Asn Ser Gly Ser Lys Ser Glu Ala Leu Asn Ile Leu Lys Glu
135                 140                 145                 150

AAG GCC CCA AAG GAC TAT ATT TTA CAA TTT CAT AAT TTA AGT TCA AAT         534
Lys Ala Pro Lys Asp Tyr Ile Leu Gln Phe His Asn Leu Ser Ser Asn
                155                 160                 165

TTA GAT AGG ATT TTT AGT CCT CCT TTA GAA GTT TAT GTT TCT CCA TTT         582
Leu Asp Arg Ile Phe Ser Pro Pro Leu Glu Val Tyr Val Ser Pro Phe
            170                 175                 180

CTT TCT TCT TCT TTT AAT CAA GTT CCA GAT GAA CTT GAA GAG TGG GTC         630
Leu Ser Ser Ser Phe Asn Gln Val Pro Asp Glu Leu Glu Glu Trp Val
        185                 190                 195

GCC GAG AAC GTC GTG TAT TCC GCT GCG CGG CCA TGG AGA CCC ATA AGT         678
Ala Glu Asn Val Val Tyr Ser Ala Ala Arg Pro Trp Arg Pro Ile Ser
200                 205                 210
```

```
ATT GTC ATT GAG GGT GAT AGC AGA ACA GGC AAA ACA ATG TGG GCC AGG      726
Ile Val Ile Glu Gly Asp Ser Arg Thr Gly Lys Thr Met Trp Ala Arg
215                 220                 225                 230

TCT CTA GGC CCA CAT AAT TAT TTA TGT GGA CAT CTA GAC CTA AGC CCA      774
Ser Leu Gly Pro His Asn Tyr Leu Cys Gly His Leu Asp Leu Ser Pro
                235                 240                 245

AAG GTG TAC AGT AAT GAT GCG TGG TAC AAC GTC ATT AGA GAC GTA GAC      822
Lys Val Tyr Ser Asn Asp Ala Trp Tyr Asn Val Ile Arg Asp Val Asp
                250                 255                 260

CCG CAT TAT TTA AAG CAC TTC AAG GAA TTC ATG GGG GCC CAG AGG GAC      870
Pro His Tyr Leu Lys His Phe Lys Glu Phe Met Gly Ala Gln Arg Asp
                265                 270                 275

TGG CAA AGC AAC ACA AAG TAC GGG AAG CCC ATT CAA ATT AAA GGG GGA      918
Trp Gln Ser Asn Thr Lys Tyr Gly Lys Pro Ile Gln Ile Lys Gly Gly
280                 285                 290

ATT CCC ACT ATC TTC CTC TGC AAT CCA GGA CCT ACC TCC TCA TAT AGG      966
Ile Pro Thr Ile Phe Leu Cys Asn Pro Gly Pro Thr Ser Ser Tyr Arg
295                 300                 305                 310

GAA TAT CTA GAC GAA GAA AAA AAC ATA TCC TTG AAA AAT TGG GCT CTC      1014
Glu Tyr Leu Asp Glu Glu Lys Asn Ile Ser Leu Lys Asn Trp Ala Leu
                315                 320                 325

AAG AAT GCA ACC TTC GTC ACC CTC TAC GAG CCA CTG TTC GCA AGT ATC      1062
Lys Asn Ala Thr Phe Val Thr Leu Tyr Glu Pro Leu Phe Ala Ser Ile
                330                 335                 340

AAT CAA GGT CCA ACA CAA GAT AGC CAA GAA GAA ACC AAT AAG GCG          1107
Asn Gln Gly Pro Thr Gln Asp Ser Gln Glu Glu Thr Asn Lys Ala
                345                 350                 355

TAAGCGTGTA GACCTAGACT GTGGCTGCTC ATACTACC                            1145

(2) INFORMATION FOR SEQ ID NO:30:

(i) SEQUENCE CHARACTERISTICS:
        (A) LENGTH: 357 amino acids
        (B) TYPE: amino acid
        (D) TOPOLOGY: linear (ii) MOLECULE TYPE: protein (xi) SEQUENCE DESCRIPTION: SEQ ID NO:30:

Met Pro Arg Leu Phe Lys Ile Tyr Ala Lys Asn Tyr Phe Leu Thr Tyr
1               5                   10                  15

Pro Asn Cys Ser Leu Ser Lys Glu Glu Ala Leu Ser Gln Leu Lys Lys
                20                  25                  30

Leu Glu Thr Pro Thr Asn Lys Lys Tyr Ile Lys Val Cys Lys Glu Leu
            35                  40                  45

His Glu Asn Gly Glu Pro His Leu His Val Leu Ile Gln Phe Glu Gly
        50                  55                  60

Lys Tyr Gln Cys Lys Asn Gln Arg Phe Phe Asp Leu Val Ser Pro Asn
65                  70                  75                  80

Arg Ser Ala His Phe His Pro Asn Ile Gln Ala Ala Lys Ser Ser Thr
                85                  90                  95

Asp Val Lys Thr Tyr Val Glu Lys Asp Gly Asn Phe Ile Asp Phe Gly
                100                 105                 110

Val Ser Gln Ile Asp Gly Arg Ser Ala Arg Gly Gly Gln Gln Ser Ala
            115                 120                 125

Asn Asp Ala Tyr Ala Glu Ala Leu Asn Ser Gly Ser Lys Ser Glu Ala
        130                 135                 140

Leu Asn Ile Leu Lys Glu Lys Ala Pro Lys Asp Tyr Ile Leu Gln Phe
145                 150                 155                 160
```

```
His Asn Leu Ser Ser Asn Leu Asp Arg Ile Phe Ser Pro Pro Leu Glu
            165                 170                 175

Val Tyr Val Ser Pro Phe Leu Ser Ser Ser Phe Asn Gln Val Pro Asp
            180                 185                 190

Glu Leu Glu Glu Trp Val Ala Glu Asn Val Val Tyr Ser Ala Ala Arg
            195                 200                 205

Pro Trp Arg Pro Ile Ser Ile Val Ile Glu Gly Asp Ser Arg Thr Gly
    210                 215                 220

Lys Thr Met Trp Ala Arg Ser Leu Gly Pro His Asn Tyr Leu Cys Gly
225                 230                 235                 240

His Leu Asp Leu Ser Pro Lys Val Tyr Ser Asn Asp Ala Trp Tyr Asn
                245                 250                 255

Val Ile Arg Asp Val Asp Pro His Tyr Leu Lys His Phe Lys Glu Phe
                260                 265                 270

Met Gly Ala Gln Arg Asp Trp Gln Ser Asn Thr Lys Tyr Gly Lys Pro
            275                 280                 285

Ile Gln Ile Lys Gly Gly Ile Pro Thr Ile Phe Leu Cys Asn Pro Gly
    290                 295                 300

Pro Thr Ser Ser Tyr Arg Glu Tyr Leu Asp Glu Glu Lys Asn Ile Ser
305                 310                 315                 320

Leu Lys Asn Trp Ala Leu Lys Asn Ala Thr Phe Val Thr Leu Tyr Glu
                325                 330                 335

Pro Leu Phe Ala Ser Ile Asn Gln Gly Pro Thr Gln Asp Ser Gln Glu
                340                 345                 350

Glu Thr Asn Lys Ala
        355

(2) INFORMATION FOR SEQ ID NO:31:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (iv) ANTI-SENSE: NO (vi) ORIGINAL SOURCE:
        (A) ORGANISM: C1V2000

(xi) SEQUENCE DESCRIPTION: SEQ ID NO:31:

GGGTCTACGT CTCTAATGAC GTTGTACC                                      28

(2) INFORMATION FOR SEQ ID NO:32:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (vi) ORIGINAL SOURCE:
        (A) ORGANISM: PTYC2V1499
```

(xi) SEQUENCE DESCRIPTION: SEQ ID NO:32:

ATTTGTGGAT CCCATTACCT TCCTGATGTT GTGG                              34

(2) INFORMATION FOR SEQ ID NO:33:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (vi) ORIGINAL SOURCE:
        (A) ORGANISM: PTYARIv466

(xi) SEQUENCE DESCRIPTION: SEQ ID NO:33:

TTAGGATCCT ATATCTGTTG TAAGGGC                                      27

(2) INFORMATION FOR SEQ ID NO:34:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (vi) ORIGINAL SOURCE:
        (A) ORGANISM: PTYARIc1046

(xi) SEQUENCE DESCRIPTION: SEQ ID NO:34:

TTAACTAATG CAGGATCCTA CATTCCAGAG GGC                               33

(2) INFORMATION FOR SEQ ID NO:35:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (vi) ORIGINAL SOURCE:
        (A) ORGANISM: PTYC2c1814

(xi) SEQUENCE DESCRIPTION: SEQ ID NO:35:

AAACGGATCC TTGAAAAATT GGGC                                         24

(2) INFORMATION FOR SEQ ID NO:36:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (vi) ORIGINAL SOURCE:
            (A) ORGANISM: PYTV1v1164

(xi) SEQUENCE DESCRIPTION: SEQ ID NO:36:

GTACGAGAAC CATACTGAAA ACGCCT                                                26

(2) INFORMATION FOR SEQ ID NO:37:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide Primer"

(iii) HYPOTHETICAL: NO (vi) ORIGINAL SOURCE:
            (A) ORGANISM: PTYC1c2196

(xi) SEQUENCE DESCRIPTION: SEQ ID NO:37:

AAATCTGCAG ATGAACTAGA AGAGTGGG                                              28

(2) INFORMATION FOR SEQ ID NO:38:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide Primer
                PTYC3c1320"

(iii) HYPOTHETICAL: NO (xi) SEQUENCE DESCRIPTION: SEQ ID NO:38:

GGTTCTGCAG CAGAGCAGTT GATCATGTAT TG                                         32

(2) INFORMATION FOR SEQ ID NO:39:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide Primer
                PTYC1v2182"

(iii) HYPOTHETICAL: NO (xi) SEQUENCE DESCRIPTION: SEQ ID NO:39:

TAGGCCATGG CCGCGCAGCG GAATACACG                                             29

(2) INFORMATION FOR SEQ ID NO:40:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: other nucleic acid (A) DESCRIPTION: /desc = "Oligonucleotide Primer
               PTYC1V2406"

(iii) HYPOTHETICAL: NO (xi) SEQUENCE DESCRIPTION: SEQ ID NO:40:

GGTTCTGCAG CTTCGGCATA TGCGTCGT                                          28

(2) INFORMATION FOR SEQ ID NO:41:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Oligonucleotide Primer
             PTYC1c2140"

(iii) HYPOTHETICAL: NO (xi) SEQUENCE DESCRIPTION: SEQ ID NO:41:

ATTTCCATGG AGACCCATAA GTATTGTC                                          28

(2) INFORMATION FOR SEQ ID NO:42:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = ""Oligonucleotide Primer
             PTYCv1707""

(iii) HYPOTHETICAL: NO (xi) SEQUENCE DESCRIPTION: SEQ ID NO:42:

GGTAGTATGA GGATCCACAG TCTAGGTCT                                         29

(2) INFORMATION FOR SEQ ID NO:43:

(i) SEQUENCE CHARACTERISTICS:
        (A) LENGTH: 1183 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
         (A) ORGANISM: Bean Golden Mosaic Geminivirus
         (B) STRAIN: Type II Isolates
         (C) INDIVIDUAL ISOLATE: Guatemala (ix) FEATURE:
(A) NAME/KEY: CDS
(B) LOCATION: 1..1059

(x) PUBLICATION INFORMATION:
(A) AUTHORS: Faria, JC
Gilbertson, RL
Hanson, SF
Morales, FJ
Ahlquist, P
Loniello, AO
Maxwell, D (B) TITLE: Bean Golden Mosaic Geminivirus Type II
    Isolates from the Dominican Republic and
    Guatemala: Nucleotide Sequences, Infectious
    Pseudorecombinants, and Phylogenetic Relationships
(C) JOURNAL: Phytopathology
(D) VOLUME: 84
(E) ISSUE: 3
(F) PAGES: 321-329
(G) DATE: 1994

(xi) SEQUENCE DESCRIPTION: SEQ ID NO:43:

```
ATG CCA CCA CCT CAA AGA TTT AGA GTT CAG TCG AAA AAC TAT TTC CTC      48
Met Pro Pro Pro Gln Arg Phe Arg Val Gln Ser Lys Asn Tyr Phe Leu
 1               5                  10                  15

ACT TAT CCT CGT TGC CCT ATA CCG AAA GAA GAA GTT CTT TCG CAA CTT      96
Thr Tyr Pro Arg Cys Pro Ile Pro Lys Glu Glu Val Leu Ser Gln Leu
            20                  25                  30

CAG AAG ATT CAT ACA GCC ACG AAT AAA AAA TTC ATC AAA GTC TGT GAG     144
Gln Lys Ile His Thr Ala Thr Asn Lys Lys Phe Ile Lys Val Cys Glu
        35                  40                  45

GAA CGT CAC GAG AAT GGT GAA CCT CAT CTT CAT GCG CTT ATT CAA TTC     192
Glu Arg His Glu Asn Gly Glu Pro His Leu His Ala Leu Ile Gln Phe
    50                  55                  60

GAA GGT AAA TTC GTC TGC ACA AAT AAA AGA TTG TTC GAC CTG GTA TCC     240
Glu Gly Lys Phe Val Cys Thr Asn Lys Arg Leu Phe Asp Leu Val Ser
65                  70                  75                  80

TCA ACC AGG TCA GCA CCT TTC CAT CCG AAC ATT CAG GGA GCT AAA TCA     288
Ser Thr Arg Ser Ala Pro Phe His Pro Asn Ile Gln Gly Ala Lys Ser
                85                  90                  95

AGT TCA GAC GTC AAG GCA TAC ATC GAC AAA GAT GGA GTC ACA ATC GAA     336
Ser Ser Asp Val Lys Ala Tyr Ile Asp Lys Asp Gly Val Thr Ile Glu
            100                 105                 110

TGG GGA CAA TTC CAA GTC GAC GGC AGA TCT GCA AGA GGA GGT CAG CAG     384
Trp Gly Gln Phe Gln Val Asp Gly Arg Ser Ala Arg Gly Gly Gln Gln
        115                 120                 125

TCT GCC AAC GAC TCA TAT GCA AAG GCA TTA AAC GCA GAT TCA ATT GAA     432
Ser Ala Asn Asp Ser Tyr Ala Lys Ala Leu Asn Ala Asp Ser Ile Glu
    130                 135                 140

TCT GCC TTG ACA ATA TTG AAG GAA GAA CAA CCG AAA GAT TAC GTC CTT     480
Ser Ala Leu Thr Ile Leu Lys Glu Glu Gln Pro Lys Asp Tyr Val Leu
145                 150                 155                 160

CAA CAT CAC AAC ATC CGT TCT AAT CTC GAA CGG ATC TTC GTC AAA GTG     528
Gln His His Asn Ile Arg Ser Asn Leu Glu Arg Ile Phe Val Lys Val
                165                 170                 175

CCG GAA CCA TGG GTT CCT CCA TTT CCG TTG TCA TCA TTC ATC AAT GTT     576
Pro Glu Pro Trp Val Pro Pro Phe Pro Leu Ser Ser Phe Ile Asn Val
            180                 185                 190

CCG GTT GTT ATG CAA GAA TGG GTT GAC GAC TAT TTC GGA AGG GGT TCC     624
Pro Val Val Met Gln Glu Trp Val Asp Asp Tyr Phe Gly Arg Gly Ser
        195                 200                 205

GCT GCG CGG CCG GAA AGA CCT ATT AGT ATC ATC GTC GAA GGT GAT TCA     672
Ala Ala Arg Pro Glu Arg Pro Ile Ser Ile Ile Val Glu Gly Asp Ser
    210                 215                 220

CGA ACC GGA AAG ACA ATG TGG GCT CGT GCA TTA GGA CCA CAT AAT TAT     720
Arg Thr Gly Lys Thr Met Trp Ala Arg Ala Leu Gly Pro His Asn Tyr
225                 230                 235                 240

TTG AGC GGT CAT TTG GAC TTT AAT TCA CGT GTC TAT TCC AAC GCA GTG     768
Leu Ser Gly His Leu Asp Phe Asn Ser Arg Val Tyr Ser Asn Ala Val
                245                 250                 255

GAA TAC AAC GTC ATT GAT GAC ATA AGC CCC AAT TAT TTG AAG TTA AAG     816
Glu Tyr Asn Val Ile Asp Asp Ile Ser Pro Asn Tyr Leu Lys Leu Lys
            260                 265                 270
```

```
CAC TGG AAA GAA CTA ATT GGG GCA CAA AAG GAC TGG CAA TCT AAC TGT       864
His Trp Lys Glu Leu Ile Gly Ala Gln Lys Asp Trp Gln Ser Asn Cys
        275                 280                 285

AAA TAT GGA AAG CCG GTT CAA ATT AAA GGA GGA ATA CCA TCA ATC GTG       912
Lys Tyr Gly Lys Pro Val Gln Ile Lys Gly Gly Ile Pro Ser Ile Val
        290                 295                 300

TTG TGC AAT CCA GGT GAG GGT TCC AGT TAT AAA GAC TTC CTC GAC AAA       960
Leu Cys Asn Pro Gly Glu Gly Ser Ser Tyr Lys Asp Phe Leu Asp Lys
305                 310                 315                 320

GAA GAA AAC CGA GCT TTA CAC AAC TGG ACT ATT CAT AAT GCG ATC TTC      1008
Glu Glu Asn Arg Ala Leu His Asn Trp Thr Ile His Asn Ala Ile Phe
                325                 330                 335

GTC ACC CTC ACA GCC CCC CTC TAT CAA AGC ACA ACA CAG GAT TGC CAA      1056
Val Thr Leu Thr Ala Pro Leu Tyr Gln Ser Thr Thr Gln Asp Cys Gln
        340                 345                 350

ACG TAGAGCCATT CGTCGACGAC GCATTGACTT GAACTGCGGC TGTTCCATAT           1109
Thr

TTTACCATAT CAAGTGCGCA GATCATGGAT TCACGCACAG GGAGAACAT CACTGCGCAT     1169

CAGGCAGAGA ATTC                                                      1183

(2) INFORMATION FOR SEQ ID NO:44:

(i) SEQUENCE CHARACTERISTICS:
        (A) LENGTH: 353 amino acids
        (B) TYPE: amino acid
        (D) TOPOLOGY: linear (ii) MOLECULE TYPE: protein (xi) SEQUENCE DESCRIPTION: SEQ ID NO:44:

Met Pro Pro Gln Arg Phe Arg Val Gln Ser Lys Asn Tyr Phe Leu
  1               5                  10                  15

Thr Tyr Pro Arg Cys Pro Ile Pro Lys Glu Val Leu Ser Gln Leu
                 20                  25                  30

Gln Lys Ile His Thr Ala Thr Asn Lys Lys Phe Ile Lys Val Cys Glu
             35                  40                  45

Glu Arg His Glu Asn Gly Glu Pro His Leu His Ala Leu Ile Gln Phe
 50                  55                  60

Glu Gly Lys Phe Val Cys Thr Asn Lys Arg Leu Phe Asp Leu Val Ser
 65                  70                  75                  80

Ser Thr Arg Ser Ala Pro Phe His Pro Asn Ile Gln Gly Ala Lys Ser
                 85                  90                  95

Ser Ser Asp Val Lys Ala Tyr Ile Asp Lys Asp Gly Val Thr Ile Glu
                100                 105                 110

Trp Gly Gln Phe Gln Val Asp Gly Arg Ser Ala Arg Gly Gln Gln
            115                 120                 125

Ser Ala Asn Asp Ser Tyr Ala Lys Ala Leu Asn Ala Asp Ser Ile Glu
    130                 135                 140

Ser Ala Leu Thr Ile Leu Lys Glu Glu Gln Pro Lys Asp Tyr Val Leu
145                 150                 155                 160

Gln His His Asn Ile Arg Ser Asn Leu Glu Arg Ile Phe Val Lys Val
                165                 170                 175

Pro Glu Pro Trp Val Pro Pro Phe Pro Leu Ser Ser Phe Ile Asn Val
                180                 185                 190

Pro Val Val Met Gln Glu Trp Val Asp Asp Tyr Phe Gly Arg Gly Ser
                195                 200                 205
```

-continued

```
Ala Ala Arg Pro Glu Arg Pro Ile Ser Ile Ile Val Glu Gly Asp Ser
    210                 215                 220

Arg Thr Gly Lys Thr Met Trp Ala Arg Ala Leu Gly Pro His Asn Tyr
225                 230                 235                 240

Leu Ser Gly His Leu Asp Phe Asn Ser Arg Val Tyr Ser Asn Ala Val
                245                 250                 255

Glu Tyr Asn Val Ile Asp Asp Ile Ser Pro Asn Tyr Leu Lys Leu Lys
                260                 265                 270

His Trp Lys Glu Leu Ile Gly Ala Gln Lys Asp Trp Gln Ser Asn Cys
            275                 280                 285

Lys Tyr Gly Lys Pro Val Gln Ile Lys Gly Gly Ile Pro Ser Ile Val
290                 295                 300

Leu Cys Asn Pro Gly Glu Gly Ser Ser Tyr Lys Asp Phe Leu Asp Lys
305                 310                 315                 320

Glu Glu Asn Arg Ala Leu His Asn Trp Thr Ile His Asn Ala Ile Phe
                325                 330                 335

Val Thr Leu Thr Ala Pro Leu Tyr Gln Ser Thr Thr Gln Asp Cys Gln
                340                 345                 350

Thr
```

(2) INFORMATION FOR SEQ ID NO:45:

(i) SEQUENCE CHARACTERISTICS:
        (A) LENGTH: 1183 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Bean Golden Mosaic Geminivirus
        (B) STRAIN: Type II
        (C) INDIVIDUAL ISOLATE: Guatemala (ix) FEATURE:
        (A) NAME/KEY: CDS
        (B) LOCATION: 1..1059

(xi) SEQUENCE DESCRIPTION: SEQ ID NO:45:

```
ATG CCA CCA CCT CAA AGA TTT AGA GTT CAG TCG AAA AAC TAT TTC CTC      48
Met Pro Pro Pro Gln Arg Phe Arg Val Gln Ser Lys Asn Tyr Phe Leu
 1               5                  10                  15

ACT TAT CCT CGT TGC CCT ATA CCG AAA GAA GAA GTT CTT TCG CAA CTT      96
Thr Tyr Pro Arg Cys Pro Ile Pro Lys Glu Glu Val Leu Ser Gln Leu
            20                  25                  30

CAG AAG ATT CAT ACA GCC ACG AAT AAA AAA TTC ATC AAA GTC TGT GAG     144
Gln Lys Ile His Thr Ala Thr Asn Lys Lys Phe Ile Lys Val Cys Glu
         35                  40                  45

GAA CGT CAC GAG AAT GGT GAA CCT CAT CTT CAT GCG CTT ATT CAA TTC     192
Glu Arg His Glu Asn Gly Glu Pro His Leu His Ala Leu Ile Gln Phe
 50                  55                  60

GAA GGT AAA TTC GTC TGC ACA AAT AAA AGA TTG TTC GAC CTG GTA TCC     240
Glu Gly Lys Phe Val Cys Thr Asn Lys Arg Leu Phe Asp Leu Val Ser
 65                  70                  75                  80

TCA ACC AGG TCA GCA CCT TTC CAT CCG AAC ATT CAG GGA GCT AAA TCA     288
Ser Thr Arg Ser Ala Pro Phe His Pro Asn Ile Gln Gly Ala Lys Ser
                 85                  90                  95
```

```
AGT TCA GAC GTC AAG GCA TAC ATC GAC AAA GAT GGA GTC ACA ATC GAA        336
Ser Ser Asp Val Lys Ala Tyr Ile Asp Lys Asp Gly Val Thr Ile Glu
            100                 105                 110

TGG GGA CAA TTC CAA GTC GAC GGC AGA TCT GCA AGA GGA GGT CAG CAG        384
Trp Gly Gln Phe Gln Val Asp Gly Arg Ser Ala Arg Gly Gly Gln Gln
            115                 120                 125

TCT GCC AAC GAC TCA TAT GCA AAG GCA TTA AAC GCA GAT TCA ATT GAA        432
Ser Ala Asn Asp Ser Tyr Ala Lys Ala Leu Asn Ala Asp Ser Ile Glu
            130                 135                 140

TCT GCC TTG ACA ATA TTG AAG GAA GAA CAA CCG AAA GAT TAC GTC CTT        480
Ser Ala Leu Thr Ile Leu Lys Glu Glu Gln Pro Lys Asp Tyr Val Leu
145                 150                 155                 160

CAA CAT CAC AAC ATC CGT TCT AAT CTC GAA CGG ATC TTC GTC AAA GTG        528
Gln His His Asn Ile Arg Ser Asn Leu Glu Arg Ile Phe Val Lys Val
            165                 170                 175

CCG GAA CCA TGG GTT CCT CCA TTT CCG TTG TCA TCA TTC CGC AAT GTT        576
Pro Glu Pro Trp Val Pro Pro Phe Pro Leu Ser Ser Phe Arg Asn Val
            180                 185                 190

CCG GTT GTT ATG CAA GAA TGG GTT GAC GAC TAT TTC GGA AGG GGT TCC        624
Pro Val Val Met Gln Glu Trp Val Asp Asp Tyr Phe Gly Arg Gly Ser
            195                 200                 205

GCT GCG CGG CCG GAA AGA CCT ATT AGT ATC ATC GTC GAA GGT GAT TCA        672
Ala Ala Arg Pro Glu Arg Pro Ile Ser Ile Ile Val Glu Gly Asp Ser
210                 215                 220

CGA ACC GGA AAG ACA ATG TGG GCT CGT GCA TTA GGA CCA CAT AAT TAT        720
Arg Thr Gly Lys Thr Met Trp Ala Arg Ala Leu Gly Pro His Asn Tyr
225                 230                 235                 240

TTG AGC GGT CAT TTG GAC TTT AAT TCA CGT GTC TAT TCC AAC GCA GTG        768
Leu Ser Gly His Leu Asp Phe Asn Ser Arg Val Tyr Ser Asn Ala Val
            245                 250                 255

GAA TAC AAC GTC ATT GAT GAC ATA AGC CCC AAT TAT TTG AAG TTA AAG        816
Glu Tyr Asn Val Ile Asp Asp Ile Ser Pro Asn Tyr Leu Lys Leu Lys
            260                 265                 270

CAC TGG AAA GAA CTA ATT GGG GCA CAA AAG GAC TGG CAA TCT AAC TGT        864
His Trp Lys Glu Leu Ile Gly Ala Gln Lys Asp Trp Gln Ser Asn Cys
            275                 280                 285

AAA TAT GGA AAG CCG GTT CAA ATT AAA GGA GGA ATA CCA TCA ATC GTG        912
Lys Tyr Gly Lys Pro Val Gln Ile Lys Gly Gly Ile Pro Ser Ile Val
            290                 295                 300

TTG TGC AAT CCA GGT GAG GGT TCC AGT TAT AAA GAC TTC CTC GAC AAA        960
Leu Cys Asn Pro Gly Glu Gly Ser Ser Tyr Lys Asp Phe Leu Asp Lys
305                 310                 315                 320

GAA GAA AAC CGA GCT TTA CAC AAC TGG ACT ATT CAT AAT GCG ATC TTC       1008
Glu Glu Asn Arg Ala Leu His Asn Trp Thr Ile His Asn Ala Ile Phe
            325                 330                 335

GTC ACC CTC ACA GCC CCC CTC TAT CAA AGC ACA ACA CAG GAT TGC CAA       1056
Val Thr Leu Thr Ala Pro Leu Tyr Gln Ser Thr Thr Gln Asp Cys Gln
            340                 345                 350

ACG TAGAGCCATT CGTCGACGAC GCATTGACTT GAACTGCGGC TGTTCCATAT           1109
Thr

TTTACCATAT CAAGTGCGCA GATCATGGAT TCACGCACAG GGAGAACAT CACTGCGCAT     1169

CAGGCAGAGA ATTC                                                      1183

(2) INFORMATION FOR SEQ ID NO:46:

(i) SEQUENCE CHARACTERISTICS:
        (A) LENGTH: 353 amino acids
        (B) TYPE: amino acid
        (D) TOPOLOGY: linear
```

(ii) MOLECULE TYPE: protein (xi) SEQUENCE DESCRIPTION: SEQ ID NO:46:

Met Pro Pro Pro Gln Arg Phe Arg Val Gln Ser Lys Asn Tyr Phe Leu
 1               5                  10                  15

Thr Tyr Pro Arg Cys Pro Ile Pro Lys Glu Glu Val Leu Ser Gln Leu
                20                  25                  30

Gln Lys Ile His Thr Ala Thr Asn Lys Lys Phe Ile Lys Val Cys Glu
            35                  40                  45

Glu Arg His Glu Asn Gly Glu Pro His Leu His Ala Leu Ile Gln Phe
        50                  55                  60

Glu Gly Lys Phe Val Cys Thr Asn Lys Arg Leu Phe Asp Leu Val Ser
 65                  70                  75                  80

Ser Thr Arg Ser Ala Pro Phe His Pro Asn Ile Gln Gly Ala Lys Ser
                85                  90                  95

Ser Ser Asp Val Lys Ala Tyr Ile Asp Lys Asp Gly Val Thr Ile Glu
            100                 105                 110

Trp Gly Gln Phe Gln Val Asp Gly Arg Ser Ala Arg Gly Gly Gln Gln
        115                 120                 125

Ser Ala Asn Asp Ser Tyr Ala Lys Ala Leu Asn Ala Asp Ser Ile Glu
130                 135                 140

Ser Ala Leu Thr Ile Leu Lys Glu Glu Gln Pro Lys Asp Tyr Val Leu
145                 150                 155                 160

Gln His His Asn Ile Arg Ser Asn Leu Glu Arg Ile Phe Val Lys Val
                165                 170                 175

Pro Glu Pro Trp Val Pro Pro Phe Pro Leu Ser Ser Phe Arg Asn Val
            180                 185                 190

Pro Val Val Met Gln Glu Trp Val Asp Asp Tyr Phe Gly Arg Gly Ser
        195                 200                 205

Ala Ala Arg Pro Glu Arg Pro Ile Ser Ile Ile Val Glu Gly Asp Ser
        210                 215                 220

Arg Thr Gly Lys Thr Met Trp Ala Arg Ala Leu Gly Pro His Asn Tyr
225                 230                 235                 240

Leu Ser Gly His Leu Asp Phe Asn Ser Arg Val Tyr Ser Asn Ala Val
                245                 250                 255

Glu Tyr Asn Val Ile Asp Asp Ile Ser Pro Asn Tyr Leu Lys Leu Lys
            260                 265                 270

His Trp Lys Glu Leu Ile Gly Ala Gln Lys Asp Trp Gln Ser Asn Cys
        275                 280                 285

Lys Tyr Gly Lys Pro Val Gln Ile Lys Gly Gly Ile Pro Ser Ile Val
        290                 295                 300

Leu Cys Asn Pro Gly Glu Gly Ser Ser Tyr Lys Asp Phe Leu Asp Lys
305                 310                 315                 320

Glu Glu Asn Arg Ala Leu His Asn Trp Thr Ile His Asn Ala Ile Phe
                325                 330                 335

Val Thr Leu Thr Ala Pro Leu Tyr Gln Ser Thr Thr Gln Asp Cys Gln
            340                 345                 350

Thr (2) INFORMATION FOR SEQ ID NO:47:

(i) SEQUENCE CHARACTERISTICS:
        (A) LENGTH: 22 base pairs
        (B) TYPE: nucleic acid
        (C) STRANDEDNESS: single (D) TOPOLOGY: linear (ii) MOLECULE TYPE: other nucleic acid
            (A) DESCRIPTION: /desc = "Oligonucleotide Primer"

(iii) HYPOTHETICAL: NO (iv) ANTI-SENSE: NO (vi) ORIGINAL SOURCE:
            (A) ORGANISM: SHGA191

(xi) SEQUENCE DESCRIPTION: SEQ ID NO:47:

CATCATTCCG CAATGTTCCG GT                                        22

(2) INFORMATION FOR SEQ ID NO:48:

(i) SEQUENCE CHARACTERISTICS:
            (A) LENGTH: 1062 base pairs
            (B) TYPE: nucleic acid
            (C) STRANDEDNESS: single
            (D) TOPOLOGY: circular (ii) MOLECULE TYPE: DNA (genomic)

(iii) HYPOTHETICAL: NO (iv) ANTI-SENSE: NO (vi) ORIGINAL SOURCE:
            (A) ORGANISM: Bean Golden Mosaic Geminivirus
            (B) STRAIN: Type II
            (C) INDIVIDUAL ISOLATE: Guatemala (ix) FEATURE:
            (A) NAME/KEY: CDS
            (B) LOCATION: 1..1059

(xi) SEQUENCE DESCRIPTION: SEQ ID NO:48:

```
ATG CCA CCA CCT CAA AGA TTT AGA GTT CAG TCG AAA AAC TAT TTC CTC       48
Met Pro Pro Pro Gln Arg Phe Arg Val Gln Ser Lys Asn Tyr Phe Leu
 1               5                  10                  15

ACT TAT CCT CGT TGC CCT ATA CCG AAA GAA GAA GTT CTT TCG CAA CTT       96
Thr Tyr Pro Arg Cys Pro Ile Pro Lys Glu Glu Val Leu Ser Gln Leu
            20                  25                  30

CAG AAG ATT CAT ACA GCC ACG AAT AAA AAA TTC ATC AAA GTC TGT GAG      144
Gln Lys Ile His Thr Ala Thr Asn Lys Lys Phe Ile Lys Val Cys Glu
        35                  40                  45

GAA CGT CAC GAG AAT GGT GAA CCT CAT CTT CAT GCG CTT ATT CAA TTC      192
Glu Arg His Glu Asn Gly Glu Pro His Leu His Ala Leu Ile Gln Phe
 50                  55                  60

GAA GGT AAA TTC GTC TGC ACA AAT AAA AGA TTG TTC GAC CTG GTA TCC      240
Glu Gly Lys Phe Val Cys Thr Asn Lys Arg Leu Phe Asp Leu Val Ser
 65                  70                  75                  80

TCA ACC AGG TCA GCA CCT TTC CAT CCG AAC ATT CAG GGA GCT AAA TCA      288
Ser Thr Arg Ser Ala Pro Phe His Pro Asn Ile Gln Gly Ala Lys Ser
                85                  90                  95

AGT TCA GAC GTC AAG GCA TAC ATC GAC AAA GAT GGA GTC ACA ATC GAA      336
Ser Ser Asp Val Lys Ala Tyr Ile Asp Lys Asp Gly Val Thr Ile Glu
            100                 105                 110

TGG GGA CAA TTC CAA GTC GAC GGC AGA TCT GCA AGA GGA GGT CAG CAG      384
Trp Gly Gln Phe Gln Val Asp Gly Arg Ser Ala Arg Gly Gly Gln Gln
        115                 120                 125

TCT GCC AAC GAC TCA TAT GCA AAG GCA TTA AAC GCA GAT TCA ATT GAA      432
Ser Ala Asn Asp Ser Tyr Ala Lys Ala Leu Asn Ala Asp Ser Ile Glu
130                 135                 140

TCT GCC TTG ACA ATA TTG AAG GAA GAA CAA CCG AAA GAT TAC GTC CTT      480
```

```
Ser Ala Leu Thr Ile Leu Lys Glu Glu Gln Pro Lys Asp Tyr Val Leu
145                 150                 155                 160

CAA CAT CAC AAC ATC CGT TCT AAT CTC GAA CGG ATC TTC GTC AAA GTG      528
Gln His His Asn Ile Arg Ser Asn Leu Glu Arg Ile Phe Val Lys Val
                165                 170                 175

CCG GAA CCA TGG GTT CCT CCA TTT CCG TTG TCA TCA TTC ATC AAT GTT      576
Pro Glu Pro Trp Val Pro Pro Phe Pro Leu Ser Ser Phe Ile Asn Val
            180                 185                 190

CCG GTT GTT ATG CAA GAA TGG GTT GAC GAC TAT TTC GGA AGG GGT TCC      624
Pro Val Val Met Gln Glu Trp Val Asp Asp Tyr Phe Gly Arg Gly Ser
        195                 200                 205

GCT GCG CGG CCG GAA AGA CCT ATT AGT ATC ATC GTC AGA GGT GAT TCA      672
Ala Ala Arg Pro Glu Arg Pro Ile Ser Ile Ile Val Arg Gly Asp Ser
    210                 215                 220

CGA ACC GGA AAG ACA ATG TGG GCT CGT GCA TTA GGA CCA CAT AAT TAT      720
Arg Thr Gly Lys Thr Met Trp Ala Arg Ala Leu Gly Pro His Asn Tyr
225                 230                 235                 240

TTG AGC GGT CAT TTG GAC TTT AAT TCA CGT GTC TAT TCC AAC GCA GTG      768
Leu Ser Gly His Leu Asp Phe Asn Ser Arg Val Tyr Ser Asn Ala Val
                245                 250                 255

GAA TAC AAC GTC ATT GAT GAC ATA AGC CCC AAT TAT TTG AAG TTA AAG      816
Glu Tyr Asn Val Ile Asp Asp Ile Ser Pro Asn Tyr Leu Lys Leu Lys
            260                 265                 270

CAC TGG AAA GAA CTA ATT GGG GCA CAA AAG GAC TGG CAA TCT AAC TGT      864
His Trp Lys Glu Leu Ile Gly Ala Gln Lys Asp Trp Gln Ser Asn Cys
        275                 280                 285

AAA TAT GGA AAG CCG GTT CAA ATT AAA GGA GGA ATA CCA TCA ATC GTG      912
Lys Tyr Gly Lys Pro Val Gln Ile Lys Gly Gly Ile Pro Ser Ile Val
    290                 295                 300

TTG TGC AAT CCA GGT GAG GGT TCC AGT TAT AAA GAC TTC CTC GAC AAA      960
Leu Cys Asn Pro Gly Glu Gly Ser Ser Tyr Lys Asp Phe Leu Asp Lys
305                 310                 315                 320

GAA GAA AAC CGA GCT TTA CAC AAC TGG ACT ATT CAT AAT GCG ATC TTC     1008
Glu Glu Asn Arg Ala Leu His Asn Trp Thr Ile His Asn Ala Ile Phe
                325                 330                 335

GTC ACC CTC ACA GCC CCC CTC TAT CAA AGC ACA ACA CAG GAT TGC CAA     1056
Val Thr Leu Thr Ala Pro Leu Tyr Gln Ser Thr Thr Gln Asp Cys Gln
            340                 345                 350

ACG TAG                                                              1062
Thr (2) INFORMATION FOR SEQ ID NO:49:

(i) SEQUENCE CHARACTERISTICS:
        (A) LENGTH: 353 amino acids
        (B) TYPE: amino acid
        (D) TOPOLOGY: linear (ii) MOLECULE TYPE: protein (xi) SEQUENCE DESCRIPTION: SEQ ID NO:49:

Met Pro Pro Gln Arg Phe Arg Val Gln Ser Lys Asn Tyr Phe Leu
 1               5                  10                  15

Thr Tyr Pro Arg Cys Pro Ile Pro Lys Glu Val Leu Ser Gln Leu
                20                  25                  30

Gln Lys Ile His Thr Ala Thr Asn Lys Lys Phe Ile Lys Val Cys Glu
            35                  40                  45

Glu Arg His Glu Asn Gly Glu Pro His Leu His Ala Leu Ile Gln Phe
        50                  55                  60

Glu Gly Lys Phe Val Cys Thr Asn Lys Arg Leu Phe Asp Leu Val Ser
```

```
                65                  70                  75                  80
Ser Thr Arg Ser Ala Pro Phe His Pro Asn Ile Gln Gly Ala Lys Ser
                    85                  90                  95
Ser Ser Asp Val Lys Ala Tyr Ile Asp Lys Asp Gly Val Thr Ile Glu
            100                 105                 110
Trp Gly Gln Phe Gln Val Asp Gly Arg Ser Ala Arg Gly Gly Gln Gln
        115                 120                 125
Ser Ala Asn Asp Ser Tyr Ala Lys Ala Leu Asn Ala Asp Ser Ile Glu
    130                 135                 140
Ser Ala Leu Thr Ile Leu Lys Glu Glu Gln Pro Lys Asp Tyr Val Leu
145                 150                 155                 160
Gln His His Asn Ile Arg Ser Asn Leu Glu Arg Ile Phe Val Lys Val
                165                 170                 175
Pro Glu Pro Trp Val Pro Pro Phe Pro Leu Ser Ser Phe Ile Asn Val
            180                 185                 190
Pro Val Val Met Gln Glu Trp Val Asp Asp Tyr Phe Gly Arg Gly Ser
        195                 200                 205
Ala Ala Arg Pro Glu Arg Pro Ile Ser Ile Ile Val Arg Gly Asp Ser
    210                 215                 220
Arg Thr Gly Lys Thr Met Trp Ala Arg Ala Leu Gly Pro His Asn Tyr
225                 230                 235                 240
Leu Ser Gly His Leu Asp Phe Asn Ser Arg Val Tyr Ser Asn Ala Val
                245                 250                 255
Glu Tyr Asn Val Ile Asp Asp Ile Ser Pro Asn Tyr Leu Lys Leu Lys
            260                 265                 270
His Trp Lys Glu Leu Ile Gly Ala Gln Lys Asp Trp Gln Ser Asn Cys
        275                 280                 285
Lys Tyr Gly Lys Pro Val Gln Ile Lys Gly Gly Ile Pro Ser Ile Val
    290                 295                 300
Leu Cys Asn Pro Gly Glu Gly Ser Ser Tyr Lys Asp Phe Leu Asp Lys
305                 310                 315                 320
Glu Glu Asn Arg Ala Leu His Asn Trp Thr Ile His Asn Ala Ile Phe
                325                 330                 335
Val Thr Leu Thr Ala Pro Leu Tyr Gln Ser Thr Thr Gln Asp Cys Gln
            340                 345                 350
Thr (2) INFORMATION FOR SEQ ID NO:50:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (iv) ANTI-SENSE: NO (vi) ORIGINAL SOURCE:
        (A) ORGANISM: SHGA221

(xi) SEQUENCE DESCRIPTION: SEQ ID NO:50:

TCATCGTCAG AGGTGATTCA C                                          21
```

-continued (2) INFORMATION FOR SEQ ID NO:51:

(i) SEQUENCE CHARACTERISTICS:
        (A) LENGTH: 1062 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Bean Golden Mosaic Geminivirus
        (B) STRAIN: Type II
        (C) INDIVIDUAL ISOLATE: Guatemala (ix) FEATURE:
        (A) NAME/KEY: CDS
        (B) LOCATION: 1..1059

(xi) SEQUENCE DESCRIPTION: SEQ ID NO:51:

```
ATG CCA CCA CCT CAA AGA TTT AGA GTT CAG TCG AAA AAC TAT TTC CTC        48
Met Pro Pro Pro Gln Arg Phe Arg Val Gln Ser Lys Asn Tyr Phe Leu
  1               5                  10                  15

ACT TAT CCT CGT TGC CCT ATA CCG AAA GAA GAA GTT CTT TCG CAA CTT        96
Thr Tyr Pro Arg Cys Pro Ile Pro Lys Glu Glu Val Leu Ser Gln Leu
             20                  25                  30

CAG AAG ATT CAT ACA GCC ACG AAT AAA AAA TTC ATC AAA GTC TGT GAG       144
Gln Lys Ile His Thr Ala Thr Asn Lys Lys Phe Ile Lys Val Cys Glu
         35                  40                  45

GAA CGT CAC GAG AAT GGT GAA CCT CAT CTT CAT GCG CTT ATT CAA TTC       192
Glu Arg His Glu Asn Gly Glu Pro His Leu His Ala Leu Ile Gln Phe
 50                  55                  60

GAA GGT AAA TTC GTC TGC ACA AAT AAA AGA TTG TTC GAC CTG GTA TCC       240
Glu Gly Lys Phe Val Cys Thr Asn Lys Arg Leu Phe Asp Leu Val Ser
 65                  70                  75                  80

TCA ACC AGG TCA GCA CCT TTC CAT CCG AAC ATT CAG GGA GCT AAA TCA       288
Ser Thr Arg Ser Ala Pro Phe His Pro Asn Ile Gln Gly Ala Lys Ser
                 85                  90                  95

AGT TCA GAC GTC AAG GCA TAC ATC GAC AAA GAT GGA GTC ACA ATC GAA       336
Ser Ser Asp Val Lys Ala Tyr Ile Asp Lys Asp Gly Val Thr Ile Glu
            100                 105                 110

TGG GGA CAA TTC CAA GTC GAC GGC AGA TCT GCA AGA GGA GGT CAG CAG       384
Trp Gly Gln Phe Gln Val Asp Gly Arg Ser Ala Arg Gly Gly Gln Gln
        115                 120                 125

TCT GCC AAC GAC TCA TAT GCA AAG GCA TTA AAC GCA GAT TCA ATT GAA       432
Ser Ala Asn Asp Ser Tyr Ala Lys Ala Leu Asn Ala Asp Ser Ile Glu
    130                 135                 140

TCT GCC TTG ACA ATA TTG AAG GAA GAA CAA CCG AAA GAT TAC GTC CTT       480
Ser Ala Leu Thr Ile Leu Lys Glu Glu Gln Pro Lys Asp Tyr Val Leu
145                 150                 155                 160

CAA CAT CAC AAC ATC CGT TCT AAT CTC GAA CGG ATC TTC GTC AAA GTG       528
Gln His His Asn Ile Arg Ser Asn Leu Glu Arg Ile Phe Val Lys Val
                165                 170                 175

CCG GAA CCA TGG GTT CCT CCA TTT CCG TTG TCA TCA TTC ATC AAT GTT       576
Pro Glu Pro Trp Val Pro Pro Phe Pro Leu Ser Ser Phe Ile Asn Val
            180                 185                 190

CCG GTT GTT ATG CAA GAA TGG GTT GAC GAC TAT TTC GGA AGG GGT TCC       624
Pro Val Val Met Gln Glu Trp Val Asp Asp Tyr Phe Gly Arg Gly Ser
        195                 200                 205

GCT GCG CGG CCG GAA AGA CCT ATT AGT ATC ATC GTC GAA GGT GAT TCA       672
Ala Ala Arg Pro Glu Arg Pro Ile Ser Ile Ile Val Glu Gly Asp Ser
```

```
                 210                 215                 220
CGA ACC GGA CAC ACA ATG TGG GCT CGT GCA TTA GGA CCA CAT AAT TAT       720
Arg Thr Gly His Thr Met Trp Ala Arg Ala Leu Gly Pro His Asn Tyr
225                     230                 235                 240

TTG AGC GGT CAT TTG GAC TTT AAT TCA CGT GTC TAT TCC AAC GCA GTG       768
Leu Ser Gly His Leu Asp Phe Asn Ser Arg Val Tyr Ser Asn Ala Val
                245                 250                 255

GAA TAC AAC GTC ATT GAT GAC ATA AGC CCC AAT TAT TTG AAG TTA AAG       816
Glu Tyr Asn Val Ile Asp Asp Ile Ser Pro Asn Tyr Leu Lys Leu Lys
                260                 265                 270

CAC TGG AAA GAA CTA ATT GGG GCA CAA AAG GAC TGG CAA TCT AAC TGT       864
His Trp Lys Glu Leu Ile Gly Ala Gln Lys Asp Trp Gln Ser Asn Cys
            275                 280                 285

AAA TAT GGA AAG CCG GTT CAA ATT AAA GGA GGA ATA CCA TCA ATC GTG       912
Lys Tyr Gly Lys Pro Val Gln Ile Lys Gly Gly Ile Pro Ser Ile Val
        290                 295                 300

TTG TGC AAT CCA GGT GAG GGT TCC AGT TAT AAA GAC TTC CTC GAC AAA       960
Leu Cys Asn Pro Gly Glu Gly Ser Ser Tyr Lys Asp Phe Leu Asp Lys
305                 310                 315                 320

GAA GAA AAC CGA GCT TTA CAC AAC TGG ACT ATT CAT AAT GCG ATC TTC      1008
Glu Glu Asn Arg Ala Leu His Asn Trp Thr Ile His Asn Ala Ile Phe
                325                 330                 335

GTC ACC CTC ACA GCC CCC CTC TAT CAA AGC ACA ACA CAG GAT TGC CAA      1056
Val Thr Leu Thr Ala Pro Leu Tyr Gln Ser Thr Thr Gln Asp Cys Gln
                340                 345                 350

ACG TAG                                                               1062
Thr (2) INFORMATION FOR SEQ ID NO:52:

(i) SEQUENCE CHARACTERISTICS:
        (A) LENGTH: 353 amino acids
        (B) TYPE: amino acid
        (D) TOPOLOGY: linear (ii) MOLECULE TYPE: protein (xi) SEQUENCE DESCRIPTION: SEQ ID NO:52:

Met Pro Pro Gln Arg Phe Arg Val Gln Ser Lys Asn Tyr Phe Leu
1               5                   10                  15

Thr Tyr Pro Arg Cys Pro Ile Pro Lys Glu Val Leu Ser Gln Leu
                20                  25                  30

Gln Lys Ile His Thr Ala Thr Asn Lys Lys Phe Ile Lys Val Cys Glu
            35                  40                  45

Glu Arg His Glu Asn Gly Glu Pro His Leu His Ala Leu Ile Gln Phe
    50                  55                  60

Glu Gly Lys Phe Val Cys Thr Asn Lys Arg Leu Phe Asp Leu Val Ser
65                  70                  75                  80

Ser Thr Arg Ser Ala Pro Phe His Pro Asn Ile Gln Gly Ala Lys Ser
                85                  90                  95

Ser Ser Asp Val Lys Ala Tyr Ile Asp Lys Asp Gly Val Thr Ile Glu
            100                 105                 110

Trp Gly Gln Phe Gln Val Asp Gly Arg Ser Ala Arg Gly Gly Gln Gln
        115                 120                 125

Ser Ala Asn Asp Ser Tyr Ala Lys Ala Leu Asn Ala Asp Ser Ile Glu
    130                 135                 140

Ser Ala Leu Thr Ile Leu Lys Glu Glu Gln Pro Lys Asp Tyr Val Leu
145                 150                 155                 160
```

```
Gln His His Asn Ile Arg Ser Asn Leu Glu Arg Ile Phe Val Lys Val
                165                 170                 175

Pro Glu Pro Trp Val Pro Pro Phe Pro Leu Ser Ser Phe Ile Asn Val
                180                 185                 190

Pro Val Val Met Gln Glu Trp Val Asp Asp Tyr Phe Gly Arg Gly Ser
                195                 200                 205

Ala Ala Arg Pro Glu Arg Pro Ile Ser Ile Ile Val Glu Gly Asp Ser
    210                 215                 220

Arg Thr Gly His Thr Met Trp Ala Arg Ala Leu Gly Pro His Asn Tyr
225                 230                 235                 240

Leu Ser Gly His Leu Asp Phe Asn Ser Arg Val Tyr Ser Asn Ala Val
                245                 250                 255

Glu Tyr Asn Val Ile Asp Asp Ile Ser Pro Asn Tyr Leu Lys Leu Lys
                260                 265                 270

His Trp Lys Glu Leu Ile Gly Ala Gln Lys Asp Trp Gln Ser Asn Cys
                275                 280                 285

Lys Tyr Gly Lys Pro Val Gln Ile Lys Gly Gly Ile Pro Ser Ile Val
                290                 295                 300

Leu Cys Asn Pro Gly Glu Gly Ser Ser Tyr Lys Asp Phe Leu Asp Lys
305                 310                 315                 320

Glu Glu Asn Arg Ala Leu His Asn Trp Thr Ile His Asn Ala Ile Phe
                325                 330                 335

Val Thr Leu Thr Ala Pro Leu Tyr Gln Ser Thr Thr Gln Asp Cys Gln
                340                 345                 350

Thr (2) INFORMATION FOR SEQ ID NO:53:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (iv) ANTI-SENSE: NO (vi) ORIGINAL SOURCE:
        (A) ORGANISM: SHGA228

(xi) SEQUENCE DESCRIPTION: SEQ ID NO:53:

GAACCGGACA CACAATGTGG GC                                                22

(2) INFORMATION FOR SEQ ID NO:54:

(i) SEQUENCE CHARACTERISTICS:
        (A) LENGTH: 1062 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Bean Golden Mosaic Geminivirus
        (B) STRAIN: Type II
```

(C) INDIVIDUAL ISOLATE: Guatemala (ix) FEATURE:
    (A) NAME/KEY: CDS
    (B) LOCATION: 1..1059

(xi) SEQUENCE DESCRIPTION: SEQ ID NO:54:

```
ATG CCA CCA CCT CAA AGA TTT AGA GTT CAG TCG AAA AAC TAT TTC CTC      48
Met Pro Pro Pro Gln Arg Phe Arg Val Gln Ser Lys Asn Tyr Phe Leu
 1               5                  10                  15

ACT TAT CCT CGT TGC CCT ATA CCG AAA GAA GAA GTT CTT TCG CAA CTT      96
Thr Tyr Pro Arg Cys Pro Ile Pro Lys Glu Glu Val Leu Ser Gln Leu
            20                  25                  30

CAG AAG ATT CAT ACA GCC ACG AAT AAA AAA TTC ATC AAA GTC TGT GAG     144
Gln Lys Ile His Thr Ala Thr Asn Lys Lys Phe Ile Lys Val Cys Glu
        35                  40                  45

GAA CGT CAC GAG AAT GGT GAA CCT CAT CTT CAT GCG CTT ATT CAA TTC     192
Glu Arg His Glu Asn Gly Glu Pro His Leu His Ala Leu Ile Gln Phe
 50                  55                  60

GAA GGT AAA TTC GTC TGC ACA AAT AAA AGA TTG TTC GAC CTG GTA TCC     240
Glu Gly Lys Phe Val Cys Thr Asn Lys Arg Leu Phe Asp Leu Val Ser
 65                  70                  75                  80

TCA ACC AGG TCA GCA CCT TTC CAT CCG AAC ATT CAG GGA GCT AAA TCA     288
Ser Thr Arg Ser Ala Pro Phe His Pro Asn Ile Gln Gly Ala Lys Ser
                85                  90                  95

AGT TCA GAC GTC AAG GCA TAC ATC GAC AAA GAT GGA GTC ACA ATC GAA     336
Ser Ser Asp Val Lys Ala Tyr Ile Asp Lys Asp Gly Val Thr Ile Glu
            100                 105                 110

TGG GGA CAA TTC CAA GTC GAC GGC AGA TCT GCA AGA GGA GGT CAG CAG     384
Trp Gly Gln Phe Gln Val Asp Gly Arg Ser Ala Arg Gly Gly Gln Gln
        115                 120                 125

TCT GCC AAC GAC TCA TAT GCA AAG GCA TTA AAC GCA GAT TCA ATT GAA     432
Ser Ala Asn Asp Ser Tyr Ala Lys Ala Leu Asn Ala Asp Ser Ile Glu
130                 135                 140

TCT GCC TTG ACA ATA TTG AAG GAA GAA CAA CCG AAA GAT TAC GTC CTT     480
Ser Ala Leu Thr Ile Leu Lys Glu Glu Gln Pro Lys Asp Tyr Val Leu
145                 150                 155                 160

CAA CAT CAC AAC ATC CGT TCT AAT CTC GAA CGG ATC TTC GTC AAA GTG     528
Gln His His Asn Ile Arg Ser Asn Leu Glu Arg Ile Phe Val Lys Val
                165                 170                 175

CCG GAA CCA TGG GTT CCT CCA TTT CCG TTG TCA TCA TTC ATC AAT GTT     576
Pro Glu Pro Trp Val Pro Pro Phe Pro Leu Ser Ser Phe Ile Asn Val
            180                 185                 190

CCG GTT GTT ATG CAA GAA TGG GTT GAC GAC TAT TTC GGA AGG GGT TCC     624
Pro Val Val Met Gln Glu Trp Val Asp Asp Tyr Phe Gly Arg Gly Ser
        195                 200                 205

GCT GCG CGG CCG GAA AGA CCT ATT AGT ATC ATC GTC GAA GGT GAT TCA     672
Ala Ala Arg Pro Glu Arg Pro Ile Ser Ile Ile Val Glu Gly Asp Ser
210                 215                 220

CGA ACC GGA AAG ACA ATG TGG GCT CGT GCA TTA GGA CCA CAT AAT TAT     720
Arg Thr Gly Lys Thr Met Trp Ala Arg Ala Leu Gly Pro His Asn Tyr
225                 230                 235                 240

TTG AGC GGT CAT TTG GAC TTT AAT TCA CGT GTC TAT TCC AAC GCA GTG     768
Leu Ser Gly His Leu Asp Phe Asn Ser Arg Val Tyr Ser Asn Ala Val
                245                 250                 255

GAA TAC AAC GTC ATT AGA GAC ATA AGC CCC AAT TAT TTG AAG TTA AAG     816
Glu Tyr Asn Val Ile Arg Asp Ile Ser Pro Asn Tyr Leu Lys Leu Lys
            260                 265                 270

CAC TGG AAA GAA CTA ATT GGG GCA CAA AAG GAC TGG CAA TCT AAC TGT     864
His Trp Lys Glu Leu Ile Gly Ala Gln Lys Asp Trp Gln Ser Asn Cys
        275                 280                 285
```

```
AAA TAT GGA AAG CCG GTT CAA ATT AAA GGA GGA ATA CCA TCA ATC GTG         912
Lys Tyr Gly Lys Pro Val Gln Ile Lys Gly Gly Ile Pro Ser Ile Val
    290             295                 300

TTG TGC AAT CCA GGT GAG GGT TCC AGT TAT AAA GAC TTC CTC GAC AAA         960
Leu Cys Asn Pro Gly Glu Gly Ser Ser Tyr Lys Asp Phe Leu Asp Lys
305                 310                 315                 320

GAA GAA AAC CGA GCT TTA CAC AAC TGG ACT ATT CAT AAT GCG ATC TTC        1008
Glu Glu Asn Arg Ala Leu His Asn Trp Thr Ile His Asn Ala Ile Phe
                325                 330                 335

GTC ACC CTC ACA GCC CCC CTC TAT CAA AGC ACA ACA CAG GAT TGC CAA        1056
Val Thr Leu Thr Ala Pro Leu Tyr Gln Ser Thr Thr Gln Asp Cys Gln
        340                 345                 350

ACG TAG                                                                 1062
Thr
```

(2) INFORMATION FOR SEQ ID NO:55:

(i) SEQUENCE CHARACTERISTICS:
        (A) LENGTH: 353 amino acids
        (B) TYPE: amino acid
        (D) TOPOLOGY: linear (ii) MOLECULE TYPE: protein (xi) SEQUENCE DESCRIPTION: SEQ ID NO:55:

```
Met Pro Pro Gln Arg Phe Arg Val Gln Ser Lys Asn Tyr Phe Leu
  1               5                  10                  15

Thr Tyr Pro Arg Cys Pro Ile Pro Lys Glu Val Leu Ser Gln Leu
             20                  25                  30

Gln Lys Ile His Thr Ala Thr Asn Lys Lys Phe Ile Lys Val Cys Glu
         35                  40                  45

Glu Arg His Glu Asn Gly Glu Pro His Leu His Ala Leu Ile Gln Phe
     50                  55                  60

Glu Gly Lys Phe Val Cys Thr Asn Lys Arg Leu Phe Asp Leu Val Ser
 65                  70                  75                  80

Ser Thr Arg Ser Ala Pro Phe His Pro Asn Ile Gln Gly Ala Lys Ser
                 85                  90                  95

Ser Ser Asp Val Lys Ala Tyr Ile Asp Lys Asp Gly Val Thr Ile Glu
            100                 105                 110

Trp Gly Gln Phe Gln Val Asp Gly Arg Ser Ala Arg Gly Gly Gln Gln
            115                 120                 125

Ser Ala Asn Asp Ser Tyr Ala Lys Ala Leu Asn Ala Asp Ser Ile Glu
    130                 135                 140

Ser Ala Leu Thr Ile Leu Lys Glu Glu Gln Pro Lys Asp Tyr Val Leu
145                 150                 155                 160

Gln His His Asn Ile Arg Ser Asn Leu Glu Arg Ile Phe Val Lys Val
                165                 170                 175

Pro Glu Pro Trp Val Pro Phe Pro Leu Ser Ser Phe Ile Asn Val
            180                 185                 190

Pro Val Val Met Gln Glu Trp Val Asp Asp Tyr Phe Gly Arg Gly Ser
        195                 200                 205

Ala Ala Arg Pro Glu Arg Pro Ile Ser Ile Val Glu Gly Asp Ser
    210                 215                 220

Arg Thr Gly Lys Thr Met Trp Ala Arg Ala Leu Gly Pro His Asn Tyr
225                 230                 235                 240

Leu Ser Gly His Leu Asp Phe Asn Ser Arg Val Tyr Ser Asn Ala Val
                245                 250                 255
```

```
Glu Tyr Asn Val Ile Arg Asp Ile Ser Pro Asn Tyr Leu Lys Leu Lys
            260                 265                 270

His Trp Lys Glu Leu Ile Gly Ala Gln Lys Asp Trp Gln Ser Asn Cys
            275                 280                 285

Lys Tyr Gly Lys Pro Val Gln Ile Lys Gly Gly Ile Pro Ser Ile Val
            290                 295                 300

Leu Cys Asn Pro Gly Glu Gly Ser Ser Tyr Lys Asp Phe Leu Asp Lys
305                 310                 315                 320

Glu Glu Asn Arg Ala Leu His Asn Trp Thr Ile His Asn Ala Ile Phe
            325                 330                 335

Val Thr Leu Thr Ala Pro Leu Tyr Gln Ser Thr Thr Gln Asp Cys Gln
            340                 345                 350

Thr (2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (iv) ANTI-SENSE: NO (vi) ORIGINAL SOURCE:
        (A) ORGANISM: SHGA262

(xi) SEQUENCE DESCRIPTION: SEQ ID NO:56:

ACGTCATTAG AGACATAAGC                                              20

(2) INFORMATION FOR SEQ ID NO:57:

(i) SEQUENCE CHARACTERISTICS:
        (A) LENGTH: 198 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (vi) ORIGINAL SOURCE:
        (A) ORGANISM: Tomato-Infecting Geminivirus from Guatemala
            (TGV-GA1)

(xi) SEQUENCE DESCRIPTION: SEQ ID NO:57:

AGATGAAGCT ATTGAAATGC TTCAAAATCT GCCATGGTCA GTCGTCAAAC CAACGTACAT    60

ACGAGTCGCC AGAGAGGAAC ACGCAGATGG ATTTCCGCAC CTCCACTGTC TCATCCAACT   120

CTCCGGGAAG TCCAACATCA AGGATGCTAG ATTTTTCGAC CTCACTCACC CAGAAGGTCT   180

GCCAATTTTC ATCCAAAC                                                198

(2) INFORMATION FOR SEQ ID NO:58:

(i) SEQUENCE CHARACTERISTICS:
        (A) LENGTH: 379 base pairs
        (B) TYPE: nucleic acid
        (C) STRANDEDNESS: single
        (D) TOPOLOGY: circular
```

(ii) MOLECULE TYPE: DNA (genomic)

(iii) HYPOTHETICAL: NO (vi) ORIGINAL SOURCE:
             (A) ORGANISM: Tomato-Infecting Geminivirus from Guatemala
                 (TGV-GA1)

(xi) SEQUENCE DESCRIPTION: SEQ ID NO:58:

```
AGGGTTCCGT GGCATTTTTG CAAATATGAG CCAGGACACC AGGGGAGCT CTCTCTAAAA       60

CTTTATTTTG CTGGTGTCCT GGTGTCCCAT TTATACTAAA ACCCTCTTGG GGACACCAAG      120

GGCAAATTCG GCCATCCGCA ATAATATTAC CGGATGGCCG CGATTTTTTT TGGACCTGGC      180

CCACTATCAG AAATTGCGTT GGGCCTTTCT GGATAAGTTA ACCAATCAAT ACACGTTTGG      240

GTAGTCTAAT TATTACAACT TGGTCACCAA GTTGTTTTAT GGTCTATAAA TTTGTCGTTA      300

TGTGTGTGGT CCAACCACGT AAATATTGAT AATGCCTAAG CGTGATGCCC CATGGCGCTT      360

AATGGCGGGT ACCCTAAGG                                                    379
```

(2) INFORMATION FOR SEQ ID NO:59:

(i) SEQUENCE CHARACTERISTICS:
            (A) LENGTH: 2744 base pairs
            (B) TYPE: nucleic acid
            (C) STRANDEDNESS: single
            (D) TOPOLOGY: circular (ii) MOLECULE TYPE: DNA (genomic)

(iii) HYPOTHETICAL: NO (vi) ORIGINAL SOURCE:
             (A) ORGANISM: Tomato Leaf Curl Geminivirus from Southern
                 India (xi) SEQUENCE DESCRIPTION: SEQ ID NO:59:

```
ACCGGATGGC CGCGATTTTT TTTGTGGGCC CCTCAACGCA CTAACTGACA AGGACATGCT       60

AACCAATCAC ATGACGCGCT CAAAGCTTAA TTGTTTTGTG GTCCCCTATT TAAACTTCGG      120

CACCAAGTAT TGTATTTTGC ACTATGTGGG ATCCATTGTT AAACGAGTTT CCTGAAACCG      180

TTCACGGTTT TAGATGTATG TTAGCAGTTA AATATCTGCA ATTAGTAGAA AAGACCTATT      240

CTCCCGACAC ATTAGGTTAC GATTTAATTA GGGATTTAAT TTCAGTTATT AGGGCTAGAA      300

ATTATGTCGA AGCGACCAGC AGATATAATC ATTTCCACTC CCGCTTCGAA GGTACGTCGC      360

CGTCTCAACT TCGACAGCCC ATATGTGAGC CGTGCTGTTG CCCCCATTGT CCGCGTCACC      420

AAAGCAAAAG CATGGGCGAA CAGGCCCATG AACAGAAAGC CAGGATGTA CAGGATGTAC       480

AGAAGTCCAG ATGTCCCTAG AGGATGTGAA GGCCCATGTA AGGTCCAGTC GTTTGAGTCC      540

AGACACGATG TAGTCCATAT AGGCAAGGTC ATGTGTATTA GTGATGTCAC TCGTGGAACC      600

GGGCTGACCC ATAGAGTTGG TAAGCGTTTT TGTGTTAAGT CTGTTTACGT TTTGGGGAAG      660

ATATGGATGG ACGAAAATAT AAAGACCAAG AATCATACGA ACAGTGTCAT GTTTTTTCTT      720

GTTCGTGACC GTCGTCCTGT TGACAAGCCA CAAGACTTTG GAGAGGTGTT CAATATGTTT      780

GACAACGAGC CTAGCACTGC TACTGTTAAG AATATGCACA GAGATCGTTA TCAGGTGTTG      840

AGGAAGTGGC ATGCAACTGT CACCGGTGGA CAGTACGCTT CAAAGGAACA GGCATTAGTG      900

AAGAAGTTTG TTAGGGTTAA TAATTATGTT GTTTATAACC AGCAAGAGGC TGGGAAATAT      960

GAGAATCATA CTGAAAATGC ATTGATGTTG TATATGGCGT GTACTCACGC CTCTAACCCT     1020

GTGTATGCTA CTTTGAAGAT ACGGATCTAT TTTTATGATT CAGTATCGAA TTAATAAATA     1080
```

```
TTGAATTTTA TTGAATATGT TTGGTCTACA TATACAACGT GGTGTAATAC ATTCCATAAT      1140

ACATAATCAA CGGCTCTGAT TACATTGTTA ATACTGATAA CTCCTAAATT ATTTAAGTAC      1200

TTAAGCACTT GGGTCTTAAA TACCCTTAAG AAGCGACCAG TCGGAGGCTG TGAGGTCATC      1260

CGGATTCGGT AGATTAGGAA ACATTTGTGT ATCCCCAACA CTTTCCTCAG GTTGTGATTG      1320

AACTGTACTT GGTCGGTGAT GATGTCTTGG TTCATCAGGA ATGGCCGGTT GTGATGCTCT      1380

GTTATCTTGA AATATAGGGG ATTTTGAATC TCCCAGATAA ACACGCCATT CTCTGCTTGA      1440

GCTGCAGTGA TGAGTTCCCC TGTGCGTGAA TCCATGGTCG TGGCAGGCTA ATGCTATGAA      1500

GTAAGAACAG CCGCACGGTA GATCAACTCG TCGACGTCTG GTCCCCTTCT TGGCTAGCCT      1560

GTGCTGCACT TTGATTGGTA CCTGAGTAGA GTGGGCCTTC GAGGGTGACG AAGGTCGCAT      1620

TCTTTATAGC CCAGAATTTT AGTTTAGAAT TCTTTTCTTC ATCCAAGAAT TCTTTATAGC      1680

TGGAGTTGGG TCCTGGATTG CAGAGGAAGA TTGTGGGAAT TCCGCCTTTA ATTTGAACTG      1740

GCTTATTGTA CTTTCTATTT GATTGCCAGT CCCTTTGGGC CCCCATGAAT TCCTTAAAGT      1800

GCTTTAGGTA GTTGGGGTCT ACGTCATCAA TTACGTTATA CCACGCATCA TTACTGTAGA      1860

CCTTTGGGCT AAGGTCTAGA TGACCACACA AATAATTATG TGGTCCCAGT GATCTGGCCC      1920

ACATAGTCTT GCCGGTCCTA CTGTCACCCT CAATCACTAT ACTTACGGGC CTCAAAGGCG      1980

CGCACCTGAC GACGTTCTCG GCAGCCCACT CTTCAAGTTC ATCTGGAACT TGATCAAAGG      2040

AAGAAGAAGA AAAAGGAGAA GCATAAACCT CCATTGGAGG TGTAAAAATC CTATCTAAAT      2100

TACATTTTAA ATTATGATAT TGAAAAATAA AATCTTTAGG GAGTTTTTCC CTAATTATTG      2160

CTAAAGCTGC TTCAGCTGAA CCTGCATTTA AGGCCTCTGC GGCAGCATCA TTAGCTGTCT      2220

GTTGACCTCC TCGTGCAGAT CTTCCATCGA TCTGAAACTC ACCCCAGTCG ATGTAATCAC      2280

TGTCCTTCTC GATGTAGGAC TTGACATCGG AGCTGAGCTT AGCTCCCTGG AAGTTTGGAT      2340

GGAATTGGGT GGAGTTATTA GGGTGAGTGA CATCGAAATG TCTGGGGTTT CGGAACTTGG      2400

ATTTACCCTT GAATTGGATG AGGGCATGGA TATGCATAGA CCCATCTTGG TGTTTCTCTT      2460

GGGCTACTCT GATAAATAAT TTATCAGATG GACAGAAAAT GTTTTTAAGG ATTTCGAGCA      2520

TTTGTTCTTT GGGTATTGGG CATTTGGGAT AAGTAAGGAA GATATTTTTG GCATTAACAC      2580

AAAAAGAGTT AATACGAGGC ATATTGAATT GGGGACACTC AAAACTCTGA GGAATGGGGG      2640

ACTCGGGGGA CGCATTTATA AGGCGTCCCT AAATGGCATT TTTGTAATTT GGGAAAGTAA      2700

TTCAAAATCC TCACGCTCCA AAAAGCGGCC ATCCGTATAA TATT                      2744
```

(2) INFORMATION FOR SEQ ID NO:60:

(i) SEQUENCE CHARACTERISTICS:
        (A) LENGTH: 1403 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (vi) ORIGINAL SOURCE:
        (A) ORGANISM: Tomato-Infecting Geminivirus from Mexico
        (Chino-like sympts)

(ix) FEATURE:
        (A) NAME/KEY: unsure
        (B) LOCATION: 1220..1403

(xi) SEQUENCE DESCRIPTION: SEQ ID NO:60:

-continued

```
AAAGGTGGTC CGATATATCC TGGGCTTGGT GTACATGGGC CTGTTAATTT AACGAGCGGC      60

CTTATCGAAT TTAGGGCCCA TACCCGTGCC ACGTGAATAA TTAGCAGGCG GGAAACCTTG     120

GAGGTCCCCG CCATTAAACG CCATGGGCA TCCCGCTTGG CCATTTTGAA TTAAAGATAT     180

AAATGCACAT GCACGTGCAT TTATAGGACC ACACCTTGGT CACCAAGGCA CAAATATCTA     240

GACTTGACAG CCGGGATGTG ATTGGTCAGT CAAAATCAAA TAATTGGTGG TCCCATCTCT     300

TTATCTCTTT AATCTCAGCC CTCTATTCTG AGTGGTCCCC CAGATACTCC AAAAAATCGC     360

GGCCATCCGG TAATATTATA GGATGGCCGC TTTTGCCCCT GGAGTTCCCC CTGTGTGTTC     420

TAGTATTTAA GGGACTCCAG GACTCCAGAA ACATAGTACG GTTTTATGAG GCACTCTCCT     480

GGAGTCCTAC ACCATATTTG CGAAAATGCC ACTACCCCCA AAGTCATTTC GTTTACAATG     540

TAAAAACATT TTCTTAACAT ATCCACAATG CGATATCCCA AAGGATGAAG CTCTCGAAAT     600

GCTGCAGTCG TTAAAAATGG TCTGTCGTAA AACCCATATA CATAAGGGTA TCACGGGAGG     660

AGCATTCCGA TGGGTTTCCG CACTTGCACT GTCTCATCCA GCTAACTGGA AGTGCAACA     720

TCAAAGATGC TCGGTTCTTC GACATTACTC ACCCCCGGAG ATCTGCCCAG TTTCATCCAA     780

ACGTTCAGGC GGCTAAAGAC ACAAATGCCG TAAAGAATTA TATCACTAAA GATGGCGATT     840

ATTGCGAATC TGGAAAGTAC AAAGTTTCCG GGGGTTCCAA AGCAAATAAA GACGACGTCT     900

ACCATAACGC TGTAAATGCA GCAAGTGCGA CAGAGGCGCT CGACATTATA AGGCTGGAGA     960

TCCAAGAACG TTCATTGTCA GCTATCATAA CGTTAAGTCT AACATCGAGC GCCTGTTCAA    1020

ACCTCCTCCT AAACCATGGA CTCCTCCTTA TCCAATTTCC TCGTTTAATA ACGTTCCTGA    1080

GGATATGCAA ACTTGGGTTG CTGAATATCT TGGTCGGACT TCCGCTGCGC GGCCAGATAG    1140

ACCGATTAGT ATTGTCATTG AGGGCGATTC GCGAAGGCAA GACAATGTGG GCACGTGCAT    1200

TAGGCCCACA TAATTATTTG AGTGTCACCT TGATTTCAAT TCAAAAGTCT ATTCAAACGA    1260

TGTGGAGTAT AACGTCATTG ATGATATCAC GCCCATTATC TAAAGTTGAA ACCTGGAAAG    1320

AGCTTATTGG GGCCCAAAGG GACTGGCAGT CCAACTGTAA ATCGGAAACC AGTTCAAATT    1380

AACGCCGGGA TTCCATCAAT TGT                                           1403
```

(2) INFORMATION FOR SEQ ID NO:61:

(i) SEQUENCE CHARACTERISTICS:
        (A) LENGTH: 780 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (vi) ORIGINAL SOURCE:
        (A) ORGANISM: Tomato-Infecting Geminivirus similar to
            Pepper Hausteco
        (C) INDIVIDUAL ISOLATE: Sinaloa, Mexico (x) PUBLICATION INFORMATION:
        (A) AUTHORS: Torres-Pacheco, I.
            Garzon-Tiznado,
            Herrera-Estrella, L.
            Rivera-Bustmante, R.
        (B) TITLE: Sequence from a new tomato-infecting
            geminivirus from Sinoala, Mexico with some
            similarity to Pepper Hausteco Virus
        (C) JOURNAL: J. General Virology
        (D) VOLUME: 74
        (F) PAGES: 2225-2231
        (G) DATE: 1993

(xi) SEQUENCE DESCRIPTION: SEQ ID NO:61:

```
CCCTGAATGT TCGGATGGAA ATGTGCTGAT CTGGTTGAGG ATACGAGGTC AAAGAATCTG      60
TTGTTCGTGC ATTGGTATTT TCCTTCGAAC TGAATAAGCA CGTGCAGATG AGGTTGCCCA     120
TCTTCATGAG ATTCTTTGCA AATTTTGATG TACTTCTTGT TTACCGGCGT CGAGAGGTTT     180
TGTAGTTGAG CGAGAGCCTC TTCTTTGGAA ATGGAACATT GGGGATAGGT GAGGAAATAA     240
TTCTTGGCAT TTAAACGAAA TCGTTTAGGT AATGGCATAT TTGTAATAAG AGAGGTGTAC     300
ACCGATTGGA GCTCTTTAAC CTGAGCTTAT TGTATCGGTG TATTGGTAGC CAATATATAG     360
TATATGGGAG TTATCTAGGA TCTTCGTACA CGTGGAGGCC ATCCGTTATA ATATTACCGG     420
ATGGCCGACC GCTTACCTTA TCTATCCGTA CAGCTTTATT TTGAATTAAA GATGTTACTT     480
TTATGCTATC CAATGAGCGT GCGTCTGGGA AGCTTAGTTA ACCGTTCCAG ACGTGGGGAC     540
CAAGTAGTGT ATGACCACTT TATTGACTGT CAGCTTTATA AATTCAAATT AACACATAAG     600
TGGTCCATAT ACCTTTAATT CAAAATGCCT AAGCGTGATG CTCCTTGGCG ATTAACGGCG     660
GGGACCGCAA GATTAGCCGA ACTGGCAATA ATTCACGGGC TCTTATCATG GCCCGAGTA      720
CTAGCAGGGC CTCAGCTTGG GTTAATCGCC CAATGTACAG GAAGCCCCGC ATTTATCGTA     780
```

(2) INFORMATION FOR SEQ ID NO:62:

(i) SEQUENCE CHARACTERISTICS:
        (A) LENGTH: 1216 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (vi) ORIGINAL SOURCE:
        (A) ORGANISM: Tomato-Infecting Geminivirus similar to
            Pepper Hausteco
        (C) INDIVIDUAL ISOLATE: Sinaloa, Mexico (xi) SEQUENCE DESCRIPTION: SEQ ID NO:62:

```
TTTTATATTC AAAAGATATT TGGATTTTAA TATTAGCAAT TACAAATAAG CAATTTAATA      60
TGTATTCCAC TAGGTTTAGA CGTGGGTTAT CGTATGGTCC ACGTCGTTCT AATGCACGTA     120
ATTATGGTTT TAAACGCACA TTGGCCGTTA AGCGTTTTGA TGGTAATCGG CGCCAGAAGC     180
AAGTGAAGAA AACCGATGAA GAGTTAAAAA TGTCATCGCA GCGTATGCAT GAAAATCAGT     240
ATGGTCCAGA TTTTGTAATG GCGCATAACA CATCAATATC TACGTTCATC AATTTCCCAC     300
AAATGTGTAA GACTCAGCCC AATCGTAGCA GGTCCTATAT TAAGTTAAAA TGTTTGCATT     360
TTAAGGGAAC CGTTAAGATT GAACGTGTTG GGGCTGAGTT AAATATGGCC GGGTTAAGTC     420
CAAAGATTGA GGGAGTTTTC ACCGTGGTTG TTGTTGTTGA CCGTAAGCCG CATTTGAGTC     480
CCACTGGCAA CTTGCACACA TTTGATGAGT TATTTGGTGC AAGAATTCAT AGTCATGGTA     540
ACTTAGCTGT TACCCCTTCG TTGAAGGAAC GGTTCTACAT TCGTCATGTG TTGAAGAGAG     600
TTATCTCCGT TGAGAAGGAC ACTATGATGC TGGATCTAGA AGGATCCACG TGCCTGTCTA     660
ATCGGCGTTT TAATTGTTGG TCCACATTTA AGGACCTGGA TCCTTCATCA TGTAACGGCG     720
TCTATGACAA TATAAGTAAA AACGCCTTGT TAGTTTATTA TTGCTGGATG TCGGATGCTA     780
TGTCTAAGGC ATCCACATTT GTATCATTTG ATTTGGACTA TGTTGGTTGA GAAATAATAA     840
ACTTGCGCAC TTTGCTCAAA TCTTTATTTT GTCACAAAAT AATATATTTA TTTCAACGAC     900
```

```
                                              -continued

TTAGGCTGTG TCGGATTACA ATTACTGTTA ATACATTCAT GGACCGTAGT CCTTCAAGTT      960

CATTTAATTG GGCCAAGGAC ATAGTTATAT TTGAGTGGGT TCGTGTTAGA CCAACTTGTG     1020

ATGCTGAATC ACCTGGGTCT AGAACACTTC CGCCTAACTG ATGAAGATCT TTATACGGAT     1080

GTAATGCGCT ATGTCCTTGG GAGTCGGGAT TTGTGTGAGT GGTTGCTATG GTGCTTCTAC     1140

ATGCCCATGA TTCACCCGGT TTTAATTCAA TTGGGCCTGT AATGCCGAAC CTTGACATTG     1200

ATGCTGACCT CAATGG                                                    1216

(2) INFORMATION FOR SEQ ID NO:63:

(i) SEQUENCE CHARACTERISTICS:
        (A) LENGTH: 1110 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (vi) ORIGINAL SOURCE:
         (A) ORGANISM: Tomato-Infecting Geminivirus similar to
             Pepper Hausteco
         (C) INDIVIDUAL ISOLATE: Sinoloa, Mexico (xi) SEQUENCE DESCRIPTION: SEQ ID NO:63:

AAATATCTAA CGTTTCAGGG GTGGTAGAGG ACGCTCCACG TCATTACACA TTTCTCCATG       60

TATGGACCAC ACTTTAATTT GAAATGAAGG CGCGCGATTG AACTCATCCA ACGACCCACA      120

TGATGCCACG TACACATAAC TCATAGTGCG CGCCAGCTGT ACCAAAGGAA AGAGAGTGGA      180

AGCGGTCGGC CATCCGGTAA TATTATAACG GATGGCCTCC ACGTGTACGA AGATCCTAGA      240

TAACTCCCAT ATACTATATA TTGGCTACCA ATACACCGAT ACCATCAGCA CAGGTTAAAG      300

AGCTCCAATC GGTGTACACC CTTCTTATTT CATAAATGCC ATTGCAATAT TTCTCTCTCT      360

AAAACCAGCT GCCAATTCTA TATAACGCAG CTGCATGTTC ATTAAATTAA TCATACTAAT      420

TCTCTCTTCT CTCTCTTCTT CAGACGCTCT TGCTTGCTTC CTCACCGGTT TCTTCATAAA      480

TTCTTCATAG AATAGCAATA TCTTAACATC GAAGTAAGCT TATTTTTTGA ACTCTTTCAG      540

CAAATAATAA TTTGTCATTT TCGTTACCAT TATCATTGTT AGGTATAGCT TCTTATTGGC      600

AGCTTCATAC TCGGTAAGCC TTCAGCTGCG CAGCCAATTT TTCATATATG GATTCTAGGT      660

TGGCGAATCC TCCTAGTGCC TTCAATTATA TAGAATCCCA TAGAGATGAA TATCAGCTCT      720

CTCATGACTT AACTGAAATA GTACTTCAAT TTCCGTCAAC GGCGTCACAG TACGCAGCCA      780

GACTTAGTCG TAGCTGTATG AAAATTGACC ATTGCGTTAT CGAGTATAGA CAGCAGGTTC      840

CGATAAACGC AACTGGATCG GTAATAGTGG AAATCCATGA CAAGAGAATG ACTGACAATG      900

AATCATTACA AGCTTCCTGG ACATTTCCAC TAAGATGCAA CATTGATCTC CATTACTTCT      960

CGGCGTCCTT CTTCTCCTTG AAGGACCCCA TACCATGGAA GCTATATTAC CGGGTCTCAG     1020

ATACTAACGT ACATCAGAAC ACACATTTTG CCAAGTTCAA AGGCAAATTG AAGTTGTCCA     1080

CAGCTAAACA CTCTGTGGAT ATACCCTTCA                                     1110
```

TRANSGENIC PLANTS EXPRESSING MUTANT GEMINIVIRUS AC1 OR C1 GENES

This application claims priority from provisional application Ser. No. 60/015,517 filed on Apr. 16, 1996.

This invention was made with United States government support awarded by the following agencies: USDA Project NO. OICD 58-3198-1-006. The United States has certain rights in this invention.

DESCRIPTION OF INVENTION

A variety of geminivirus genes and mutant derivatives were generated and transferred to plant cells. Transgenic plants containing these genes were produced. Transgenic plants containing trans-dominant mutations developed resistance to geminivirus infection.

BACKGROUND OF THE INVENTION

Geminiviruses present the most serious disease problem in many vegetable crops in tropical and subtropical regions. For example, major epidemics of geminivirus infections of beans and tomatoes have occurred in Florida, the Caribbean Basin, Mexico, and Central America. In the past, traditional breeding methods failed to produce cultivars with significant levels of resistance to geminiviruses. An alternative approach lies in producing virus-resistant transgenic plants according to the present invention.

The geminivirus group are single stranded DNA viruses that infect both monocotyledonous (monocot) and dicotyledonous (dicot) plants. A common feature among all gemini viruses is the mode of genomic replication, which involves a rolling circle mechanism.

Tomato mottle virus (ToMoV) is one example of a geminivirus. It has a two component (bipartite) genome, an ability to infect dicot plants and is transmitted by whitefly. The DNA of its two genomic components, DNA-A and DNA-B, has previously been cloned and sequenced. Isolated clones of DNA-A and DNA-B of ToMoV are themselves infectious when mechanically inoculated into tomato and $N.$ benthamiana, or when delivered to either host by agroinoculation. An invariant geminiviral DNA sequence required for replication is present in an intergenic, common region (CR) in each genomic component.

The ToMoV DNA-A genomic component has four ORF, one of which, AC1, must be expressed for efficient replication of both A and B components. The AC1 ORF encodes a protein having several functional activities: a DNA binding site specific to the DNA-A CR; a DNA nicking activity; and a NTP binding activity. The DNA binding region mediates an initiator protein function during rolling circle replication.

AC3 protein is a second ToMoV-coded function involved in DNA replication and production of single-stranded circular DNA.

Tomato yellow leaf curl virus (TYLCV) is another example of a geminivirus. TYLCV has a monopartite genome organization, infects monocot plants, and is leafhopper transmitted. The TYLCV Cl protein is required for replication, encoded by the C1 ORF.

Being DNA viruses, geminiviruses offer advantages for antiviral strategies. Several geminiviruses have been cloned and sequenced. Transgenic plants having mutant viral genes can be produced, e.g., by introducing expression cassettes comprising mututated virus genes directly into plants with a particle gun, or into plant suspension cells or protoplasts by electroporation, or by Agrobacterium transfection.

SUMMARY OF THE INVENTION

The invention involves production of transgenic plants containing DNA encoding AC1/C1 wildtype and mutant sequences that negatively interfere in trans with geminiviral replication during infection. The resulting transgenic plants are resistant to viral infection.

DETAILED DESCRIPTION OF THE INVENTION

A. Production of Infectious Clones

Figure 1:
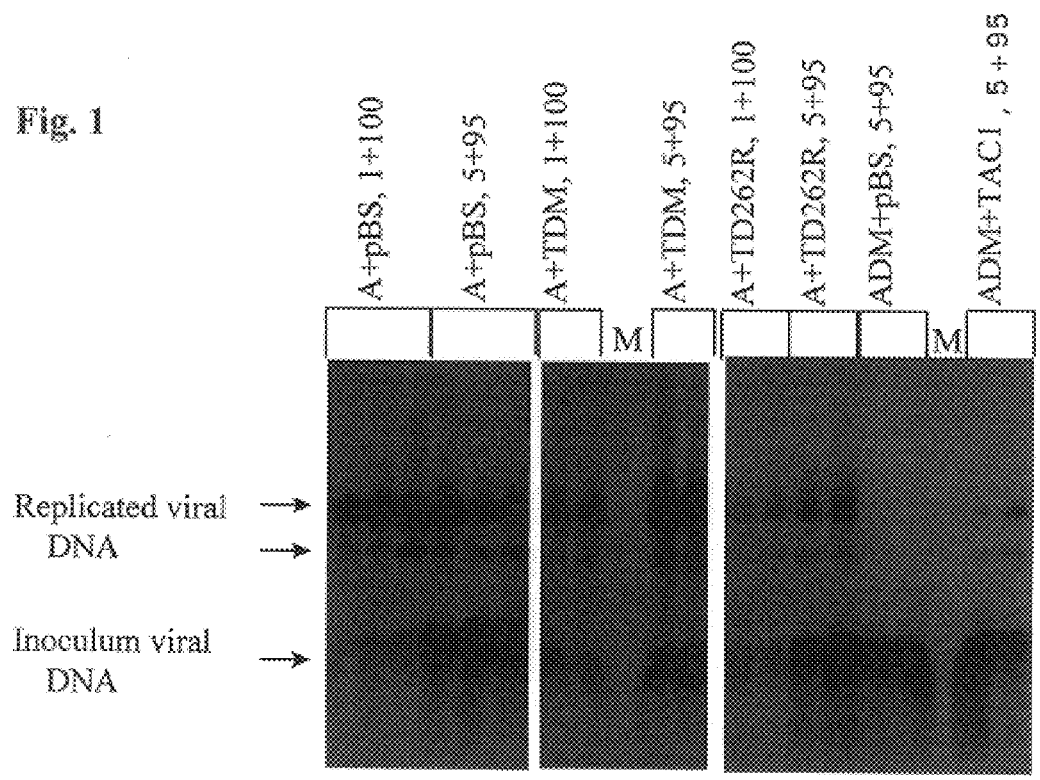
FIG. 1 shows the results of a transient assay for transdominance done with BGMV-GA in NT-1 cells.

Infectious clones of geminiviruses are produced by methods known to the skilled worker. Geminivirus DNA is extracted from tissue as follows. Young tissue is collected from infected plants, frozen in liquid nitrogen and ground in a mortar in the presence of extraction buffer (10 mM Tris-Cl, pH 7.5, 10 mM EDTA, and 1% SDS, 1:4 wt/vol ratio) and centrifuged for about $10^5$ g minutes. The supernatant is adjusted to about 1 M NaCl and stored at about 4° C. for about 12 hr, then centrifuged for about $10^7$ g minutes. After phenol extraction, the solution is adjusted to 0.3 M sodium acetate, and the DNA is precipitated in alcohol. Viral nucleic acids are isolated by agarose gel electrophoresis.

These viral nucleic acid fractions are digested with restriction enzymes and isolated by agarose gel electrophoresis. The DNA is cloned in a suitable cloning vector, e.g., pBluescript KS+, and its identity is confirmed by sequencing.

Full-length clones of the geminivirus genome are constructed, e.g., by a PCR-based cloning strategy. Primers are synthesized that will amplify the entire ORF plus about ten nucleotides on each side of the ORF. The primers should include mismatched bases to create restriction sites before and after the C1 or AC1 ORF which will allow convenient cloning without altering initiation and termination codons of C1 or AC1 ORFs.

Primer 1 is complementary to and anneals with the viral sense strand of the geminiviral genome. The 5' end of the primer is located 40–50 base pairs 3' of the translation start, and the 3' end is located 10–20 base pairs 3' of the translation start site. Translation start is defined by CAT on the viral sense strand; AC1 or C1 ORFs are located on the complementary strand of the viral genome and sequence coordinates are given for the viral sense polarity strands.

Primer 2 is complementary to and anneals with the strand (complementary sense polarity) of the geminiviral genome. The 5' end of the primer is located 40–50 base pairs 3' of the AC1 or C1 termination condon, and the 3' end of the primer is located 10–20 base pairs 3' of the translation stop as determined on the complementary sense polarity strand. The primers are used in a PCR reaction to amplify the C1 or AC1 ORF from cloned viral DNA or purified geminivirus DNA. The amplified DNA is digested with appropriate restriction enzymes to cut sites engineered in the ends of the PCR fragment and the resulting fragment is cloned into a suitable vector. C1- or AC1-containing clones are identified and sequenced to confirm the presence and integrity of the cloned C1 or AC1 ORF.

The sequence of the AC1/C1 ORF is used for designing the primers for amplification of the PCR fragment of AC1/C1 ORF. For example, these primers are designed so that this ORF is cloned into the BamHI and HindIII sites of pBluescript KS+. The BamHI site is located at the 5' end of the complementary sense primer, which amplifies the amino terminal end of the ORF. A HindIII site is located at the 5' end of the viral sense primer which anneals to the carboxy end of the ORF.

Infectious clones preferably are selected. The infectivity of the clones are determined by construction of Agrobacterium having greater-than-full-length viral genes with at least two common regions of DNA-A and DNA-B. Infectivity is determined by microparticle inoculation. Seeds are germinated on moist filter paper to produce 1–3 cm long radicles of a host, and this tissue is bombarded by DNA-coated particles with a particle gun. Inoculated plants are placed in a growth chamber at about 26° C. with about 14 hour photoperiods. Infectivity is confirmed by PCR with primers specific for geminiviruses or Southern blot analysis. For example, 1.3-kb PCR products are expected when primers PAL2v1978 and PAV1c715 are used.

Cloned viral DNA is digested with restriction enzymes and analyzed on agarose gels to produce a unique 2.5 to 2.7-kb fragment. The DNA bands are removed from the gel and cloned into an appropriate vector. For monopartite geminiviruses, the insert preferably includes the entire genome. For bipartite geminiviruses, entire inserts of both genomic components are preferable. The single insert of the monopartite geminivirus or both cloned components of bipartite geminiviruses are introduced into a host plant and tested for infectivity by biolistic delivery or agroinoculation.

The cloned C1 (monopartite viruses) or AC1 (bipartite viruses) ORF are isolated by selecting for the following characteristics:

A. The AC1 or C1 ORF encodes a protein product of about 42 Kd.

B. The nucleotide sequence of the C1 or AC1 ORF is at least 60% homologous to the AC1 ORF of a previously identified geminiviruses (e.g., BDMV, ToMoV, or TYLCV). The deduced amino acid sequence of the ORF will contain several characteristic sequences which are similar in sequence and relative position within the ORF i.e., motifs within the C1 or AC1 sequences.

B. Introducing Mutations

Mutations are introduced by site-directed mutagenesis of cloned C1 or AC1 ORF by methods known in the art, e.g., using the method of Kunkel et al. (Recombinant a DNA Methodology, 1989, pp. 587–601) (herein, "Kunkel mutagenesis").

In particular, mutations are introduced into amino acid sequence motifs in C1 or AC1 ORF that are highly conserved among all gemini viruses. Four motifs are preferred in the DNA-nicking domain of the protein. These include (capital letters denote high conservation of amino acid, lower case denotes some conservation, and "x" denotes a variable position in the motif):

(1) FLTYpxC
(2) HlHvliQ
(3) vKxYxdKd; and
(4) FHPNIQxak.

Additionally two motifs are preferred in the NTP-binding domain of the protein. These include:

(5) EGx$_2$RTGKt; and
(6) NviDDi.

The individual codons specifying the most highly conserved amino acids within these motifs are mututated. For example, one or more of the following mutations introduced to the C1 or AC1 ORF:

(1) vKxYxdKd to
  (a) vKxFxdKd;
  (b) vKxAxdKd;
  (c) vKxYxdRd;
(2) EGx$_2$RTGKt to
  (a) EGx$_2$RTGHt;
  (b) EGX$_2$RTGAt;
  (c) RGx$_2$RTGKht;
(3) NviDDi to
  (a) NviRDi;
  (b) NviKDi; or
  (c) NviDYi, (herein mutations 1(a), 1(b), 1(c), 2(a), 2(b), 2(c), and 3(a), 3(b), 3(c), respectively). Acidic or basic amino acids are changed to the opposite charge, to alanine (alanine scanning) or to other neutral amino acids. Combinations of mutants are also made. For example, a single C1 or AC1 ORF containing codon changes corresponding to vKxFxdKd and EGx$_2$RTGHt (double mutations 1(a) and 2(a), above) are constructed and tested. Other mutants in motifs within AC1/C1 are possible and are used. The presence of the codon change is confirmed by DNA sequencing. Agrobacterium-mediated transfer of the plant expressible mutated AC1/C1 ORF is done using procedures known to those skilled in the art.

If an infectious clone of the geminivirus is available, effects of mutations on replication can be tested. The mutation is introduced into the C1 or AC1 ORF of an infectious clone. Mutant DNA is transferred to plant cells. Replication of wild type viruses is tested for infection as a positive control. Mutations which create transdominant molecules generally abolish replication when engineered into infectious clones. A number of mutations which change codons for conserved amino acids within these motifs will be lethal and potentially transdominant. Other mutations in C1 or AC1 which abolish replication should also be considered potentially transdominant. Any non-functional C1 or AC1 molecule has the potential to be transdominant.

Mutated C1 or AC1 ORFs are installed into a suitable plant transformation vector in the sense orientation and under the control of a strong constitutive promoter sequence and suitable terminator for high level expression in the target plant species. This step is performed for each of the C1/AC1 mutants created.

C. Assays

A transient assay is useful to screen candidate constructs for transdominant interference activity. This is done by first coinoculating protoplasts or a plant cell suspension culture with the infectious geminivirus clone and a plasmid containing mutant C1 or AC1 ORF under control of a strong constitutive plait promoter. Control treatments are inoculated with an infectious clone. Total DNA is harvested from inoculated cells, and is assayed for viral replication. Transdominant C1 or AC1 mutants are identified as those which suppress geminiviral replication relative to control treatments after coinoculation.

In vitro assays for transdominance correlate lethal mutations and transdominant activity in transient assays. This is exemplified in a BGMV-GA model system. These results are readily applicable to produce a transdominant C1 or AC1 ORFs from other geminiviruses. Transgenic plants resistant to ToMoV were created by transforming them with an AC1 ORF derived from ToMoV and engineered to contain similar mutations.

Expression cassettes constructed above are installed into binary plasmids and transformed into Agrobacterium strains for plant transformation protocols. Plants are transformed by methods tailored to the specific variety or line.

Transgenic status of $R_0$ and later generation plants and their segregating progeny is verified by routine methods, including: ELISA assays for NPTII protein detection; DNA assays such as PCR amplification with the AC1/C1 primers of plants and Southern blot hybridization for detection of transgenes using AC1/C1 as viral probes; and Southern blot hybridization to detect AC1 or C1 transgenes. Demonstration that $R_1$ plants transformed with geminivirus gene constructions express NPTII protein is done by ELISA. Protein in leaf tissue samples taken from $R_1$ transgenic plant seedlings is extracted and analyzed for NPTII protein by ELISA.

Geminivirus transgene expression is also measured by Northern blot analysis. Transgene expression in a number of $R_o$ and $R_1$ plants was done by Northern blot hybridization. Total RNA extracted from leaves of transgenic plants is separated by agarose gel electrophoresis. After electrophoresis, RNA is pressure blotted onto membrane. Membranes are hybridized with radiolabeled probes, washed, and autoradiographed.

D. Identification of Gemini-Resistant Transgenic Plants

Geminivirus-resistant transgenic plants are identified by challenging transgenic plants and progeny. $R_1$ plants from self pollinated $R_0$ primary regenerants are agroinoculated about 3 weeks after sowing. Alternative methods include biolistic inoculation, sap transmission from infected tissue (if the isolate is mechanically transmissible), insect transmission, or grafting. For bipartite geminiviruses, agroinoculation preferably involves delivery of greater-that-full-length (i.e., at least 2 common regions) DNA-A and DNA-B components into the seedlings using Agrobacterium strains, e.g., containing a binary vector having in its T-DNA a partial or full tandem duplication of infectious geminivirus DNA. Geminivirus-resistant plants are incorporated into traditional breeding programs to develop elite breeding lines that include the resistance-conferring transgene. These changes produce C1 or AC1 molecules when made alone or in combination with a mutant.

Plants showing the highest steady state levels of transgene RNA are challenged by Agrobacterium-mediated inoculation. Resistance is determined by lack or delay of symptom expression and low levels of viral DNA in plants as determined by squash blot hybridization tests with viral probes (Gilbertson et al., 1991. Plant Disease 75:336–342.). Resistance is also determined by inoculation with viruliferous *Bemisia tabaci* as described. It is expected that plants with low levels of mRNA accumulation for the mutated AC1/C1 ORF have symptoms and those with high levels have no symptoms.

Since the A1/C1 proteins have domains required for DNA-nicking and NTP-binding that are conserved among all geminiviruses, an antiviral strategy involving mutated AC1/C1 protein is applicable to plant-geminivirus systems in general.

Other viruses include:

| Virus | Genes/Regions | SEQ ID NO. |
|---|---|---|
| TGV-GA1 | AC1 ORF DNA-A (complementary seq) | 57 |
| TGV-GA1 | Common & Intergenic Region (viral) | 58 |
| TLCV-IND | Full Length Sequence (stemloop begin) | 59 |
| "Chino" | Partial AC1, Common region, AV1 | 60 |
| PHV | AC1, Common region, Intergenic, AV1 | 61 |
| PHV | BV1 ORF | 62 |
| PHV | BC1, Hypervar., Common, & Interg. Reg | 63 |

The following examples are offered by way of illustration and not by way of limitation.

EXAMPLE 1

Gene Expression Vectors

All *E. coli* culture and plasmid DNA isolation methods were carried out according to standard methods. Restriction digestions, filling in of 5' end overhangs, calf intestinal alkaline phosphatase treatments of DNA and ligation of DNA fragments and gel electrophoretic separation of DNA fragments and their isolation from gels were done according to manufacturers' recommendations and methods. Agrobacterium large plasmid DNA was isolated. Agrobacterium transformation and culture is performed according to general methods known to those skilled in the art.

Tables 1A and 1B list geminiviral transcribed sequences, expression vectors, binary plasmids, and Agrobacterium strains described in the Examples.

TABLE 1A

Constructs used to Create Transgenic Plants

| Transcribed Seq. (open reading frame or antisense seq.) | Expression Vector Used | Binary Vector Used | *Agrobacterium tumefaciens* designation |
|---|---|---|---|
| ToMoV-Ac1as | pRT101e | pJTS246Δ | RTAC |
| ToMoV-AC1 | pRT101e | pJTS246Δ | RTSC |
| ToMoV-AC1as | DH51 | pJTS235 | DHAC |
| ToMoV-AC1 | DH51 | pJTS235 | DHSC |
| ToMoV-AC1-AC2-AC3as | pRT101e | pJTS246Δ | RT3AA |
| ToMoV-AC1as | pRT101e | pJTS246Δ | RTFS |
| ToMoV-AC1 | pLAT | pJTS246Δ | LASD, LASU |
| ToMoV-AC1dlm | pRT101e | pJTS246Δ | MEU |
| ToMoV-AC1dlm | pRT101e | pJTS246Δ | MEU2 |

TABLE 1A-continued

Constructs used to Create Transgenic Plants

| Transcribed Seq. (open reading frame or antisense seq.) | Expression Vector Used | Binary Vector Used | Agrobacterium tumefaciens designation |
|---|---|---|---|
| ToMoV-AC1dlm1 | pRT101e | pJTS246Δ | MUA |
| ToMoV-AC1dlm23 | pRT101e | pJTS246Δ | MUB |
| ToMoV-AC1 | pΔ1CO35 | pJTS246Δ | COALS |
| ToMoV-AC1dlm | pΔ1CO35 | pJTS246Δ | CODLM |
| ToMoV-AC1dlm1 | pRTIN | pJTS246Δ | MUAIN |
| ToMoV-AC1dlm23 | pRTIN | pJTS246Δ | MUBIN |
| TYLCV-C1as | pRT101e | pJTS246Δ | LCA |
| TYLCV-ΔC2as TYLCV-C1as | pRT101e | pJTS246Δ | LCR' |
| TYLCV-V1as | pRT101e | pJTS246Δ | LCR" |
| TYLCV-C1-ΔC2-ΔC3as | pRT101e | pJTS246Δ | RT3CA |
| TYLCV-C1-ΔC2-ΔC3as | pΔ1CO35 | pJTS246Δ | CO3CA |
| TYLCV-C104 | $eP_{mas} - T_{phas}$ | pGA482Δ+HYG$^R$ | C104 |
| TYLCV-C225 | $eP_{mas} - T_{phas}$ | pGA482Δ+HYG$^R$ | C225 |
| TYLCV-C259 | $eP_{mas} - T_{phas}$ | PGA482Δ+HYG$^R$ | C259 |
| TYLCV-C1-ΔC2-ΔC3 | pRT101e | pJTS246Δ | RT3CS |

TABLE 1B

Constructs for Agrobacterium Inoculation

| Geminivirus strain and Sequence | Binary Vector Used | Agrobacterium Designation |
|---|---|---|
| ToMoV-A dimer | pJTS222 | A.t. ToMoV-A |
| ToMoV-B 1.67mer | pJTS222 | A.t. ToMoV-B |
| TYLCV-EG dimer | pJTS222 | A.t. TYLC-EG |

Example 1.1

Synthesis of Expression Vector pRT101e

The pRT101e expression vector listed in Table 1A was made by removing a 325-bp HindIII-EcoRV fragment from pUC8-CaMVCAT (Pharmacia) and inserting it into HincII-HindIII-digested pRT101 (Dr. Topfer, Max Planck-Institut fur Zuchtungsforschung, 5000 Koln 30, Germany), thereby adding a segment of the 35S promoter containing the upstream enhancer (Kay et al., Science, 1987, 236:1299–1302) to the 5' end of the 35S promoter sequence of PRT101.

Example 1.2

Expression Vector pDH51

The pDH51 expression vector of Table 1A (T. Hohn, Friedrich Miescher Institute, P.O. Box 2543, CH-4002, Basel, Switzerland) is comprised of a CaMV 35S promoter-35S terminator expression cassette.

Example 1.3

Synthesis of Expression Vector pΔ1CO35

The pΔ1CO35 expression vector of Table 1A was derived from pCO1bam (Dr. Neil Olszewski, University of Minnesota-Twin Cities, College of Biological Sciences). The 1.0-kb EcoR1-SalI fragment of pCO1bam, containing the promoter controlling expression of the commelina yellow mottle virus (CoYMV) transcript (Medberry et al., Plant Cell, 1992, 4:185–92), was inserted into EcoR1-SalI-digested pSL1180 (Pharmacia). A 1.1-kb EcoRI-DraI fragment of the resulting construct was inserted into EcoRI-HincII-digested pRT101, thereby replacing the CaMV 35S promoter of pRT101 with the COYMV promoter. Some restriction sites, including BamHI and BglII, were removed by partially digesting this plasmid with HindIII and recircularizing it with T4 DNA ligase to produce pΔ1CO35.

Example 1.4

Synthesis of Expression Vector pRTIN

The pRTIN expression vector of Table 1A is a derivative of pRT101e and pCOIN, in which the 35S terminator of pRT101e was replaced with the protease inhibitor gene terminator/polyadenylation site ($T_{INH}$) of pCOIN. To produce pCOIN, the 760-bp HindIII-XbaI fragment of pTPI-1 (Dr. C. Ryan, Washington State University, Pullman, Wash.) containing T. was inserted into HindIII-XbaI-digested Bluescript II KS+ (Stratagene). The 770-bp XbaI-KpnI fragment of the resulting construct was inserted into XbaI-KpnI-digested pUC19. The 800-bp PstI-KpnI terminator fragment of the resulting plasmid was ligated with the KpnI-PstI fragment of pΔ1CO35 to produce pCOIN. The 805-bp SphI-SspI fragment of pCOIN was inserted into SphI-SmaI-digested pRT101e, thereby replacing the 35S terminator of pRT101e with $T_{INH}$. The resulting plasmid was further modified by inserting into a EcoRI site a DNA fragment with EcoRI ends and internal restriction sites including BamHI to produce pRTIN.

Example 1.5

Synthesis of Expression Vector $eP_{mas}-T_{phas}$

The expression vector $eP_{mas}-T_{phas}$ of Table 1A was assembled by combining an octopine synthase upstream activating sequence (ocs UAS) and a mannopine synthase promoter (mas2').

The ocs UAS was excised from pAL1050 (Dr. Paul J. J. Hooykaas, State Univ. of Leiden, 2333 AL Leiden, The Netherlands), which was isolated from *Agrobacterium tumefaciens* strain LBA4404 (Dr. P. J. J. Hooykaas). A 2.8-kb EcoRI fragment of pAL1050, containing nt 13362-16202 of ocs UAS was inserted into the EcoRI site of pSL1180 (Pharmacia). A 311-bp SacI-BamHI fragment of the resulting plasmid, containing nt 13774-14085 of the ocs UAS, was ligated into SacI-BamHI-digested pBluescript II KS+. A 285-bp XhoI-MfeI fragment containing the ocs UAS was ligated with the EcoRI-XhoI fragment of pBluescript II KS+ with ocs UAS to produce a plasmids having tandemly repeated ocs UAS element structure. A EcoRI-XhoI fragment of the recombinant plasmid was ligated with another MfeI-XhoI fragment to produce a recombinant plasmid, pBluescript+UAS$^3$, having three tandemly repeated ocs UAS elements.

The mas2' promoter element was isolated as follows. Plasmid pE93 (Dr. Stan Gelvin, Purdue University) is derived from pRK290 (Ditta et al., 1980). EcoRI fragment #13 of pE93 contains nt 16202-21634 of the octopine Ti plasmid, and lacks an internal ClaI fragment at nt 8672-20128 (Eco13ΔC1a). A 4-kb EcoRi-XhoI fragment was ligated with the SalI-EcoRI fragment of pBR322, to produce pJTS213. This plasmid was introduced into *E. coli* GM119 (Dr. Gurnam Gill, Pharmacia & Upjohn, Kalamazoo, Mich.), which is deficient in DNA adenine methylation. Thus, normally undigestible ClaI site beginning at nt 20128 in Eco13ΔCla is cleavable by ClaI. A 951-bp ClaI-NcoI fragment of pJTS213 containing nt 21079-20128 was isolated and ligated with the ClaI-NcoI fragment of pSL1180 to produce pSL1180+P$_{mas}$.

A ocs UAS-enhanced mannopine synthase promoter cassette (Ep$_{mas}$) was assembled as follows. A 365-bp ClaI-FspI mas2' fragment from pSL1180+P$_{mas}$ was ligated with the ClaI-EcoRV fragment of pBluescript+VAS$^3$. Clones in which the mas2' was inserted downstream of the ocs UAS repeat were identified by restriction digestion. To facilitate the addition of the phaseolin transcription terminator, a 250-bp multiple cloning site (mcs) XhoI-SalI fragment from pSL1180 was ligated into the XhoI-digested recombinant plasmid. Two plasmids, pBluescript+UAS$^3$+P$_{mas}$+mcs (orientations I and II), containing a construct with the mcs inserted in the two possible orientations were isolated.

The phaseolin terminator was added to pBluescript+ UAS$^3$+P$_{mas}$+mcs, completing the assembly of Ep$_{mas}$–mcs–T$_{phas}$, as follows. A 1.1-kb PstI-EcoRI fragment of pUC19–hph–T$_{phas}$ (described below in the assembly of pGA482Δ+HYG$^R$), which contains the phaseolin transcription terminator (T$_{phas}$), was ligated with PstI-EcoRI-digested pBluescript II KS+. A 1.2-kb SacII-ClaI fragment of the resulting plasmid was ligated with the SacII-ClaI fragment of pBluescript+UAS$^3$+P$_{mas}$+mcs (orientation I) to produce a plasmid having the eP$_{mas}$-T$_{phas}$ insert.

Example 1.6

Synthesis of Expression Vector pLAT

The expression vector pLAT of Table 1A was produced as follows. The promoter of the LAT52 gene (Twell et al., Development, 1990, 109:705–13) was used to construct an AC1 gene construct in sense orientation that does not express in vegetative tissue. A 600-bp NcoI-SalI fragment of pLAT52-7a (Dr. S. McCormick, Plant Gene Expression Center, USDA ARS, Albany, Calif.), which contains the LAT52 promoter, was ligated with NcoI-SalI-digested pSL1180 to produce pLAT.

Example 2.1

Synthesis of Binary Vector pJTS246Δ

The binary vector pJTS246Δ of Table 1A was produced as as a derivative of pGA482 (Dr. G. An, Washington State University, Pullman, Wis.), by replacing the nopaline synthase controlled NPTII sequence with a CaMV 35S promoter-NPTII-phaseolin terminator selectable marker. The selectable marker was situated at the left T-DNA border to insure that the passenger gene, inserted at the right T-DNA border, would be transferred into the plant cell.

A BamHI fragment of pUC8-CaMVCAT was ligated with a 2.2-kb BamHI fragment of pDOB513ro4.6K (J. L. Slightom, Pharmacia & Upjohn), containing the NPTII coding region and octopine Ti plasmid T-DNA ORF No. 26 transcription terminator, to produce pJTS228. The pJTS228 construct has the 2.2-kb fragment, inserted as a transcription fusion unit immediately downstream of the CaMV 35S promoter of pUC8-CaMVCAT. Most of the CAT gene of pUC8-CaMVCAT was deleted from pJTS228 by digesting with EcoRI to produce pJTS228Δ. A 4.0-kb BamHI-NcoI fragment from pJTS228 was ligated with a 1.55kb BamHI-NcoI fragment from pkanPhas (J. L. SLightom, Pharmacia & Upjohn) containing the NPTII coding sequences 5' distal to the NcoI site and the phaseolin terminator. A resulting plasmid, in which the T-DNA transcription terminator fused to the NPTII ORF was replaced with the phaseolin storage protein terminator from *Phaseolus vulgaris*, was designated pJTS233.

pJTS233 was digested with HindIII and flush ended. A 2.8-kb EcoRI fragment containing the 35S promoter, NPTII coding region and phaseolin terminator was isolated and ligated in a 3-part reaction with SmaI-BamHI fragment of pUC9 and an 8.0-kb BamHI-EcoRI fragment of pGA482 containing the broad host range replicon, left and right nopaline Ti T-DNA borders and nopaline synthase promoter. The desired construct, pJTS246, was cloned and isolated. pJTS246 was modified to eliminate the ampicillin drug resistance contributed by pUC9. The plasmid was digested with ScaI and HindIII, and treated with HindIII linkers followed by HindIII digestion. The resulting plasmid, pJTS246Δ, had 1730-bp of pUC sequence deleted from pJTS246.

Example 2.2

Synthesis of Binary Vector pJTL222 pJTS222 is pGA492 (Dr. G. An) in which a 2.2-kb BamHI-HindIII fragment replaced by the 430 bp BamHI-HindIII fragment of pUC8-CamVCAT containing the CaMV 35S promoter.

Example 2.3

Synthesis of Binary Vector pJTS235 pJTS235 was a binary plasmid derived from pGA492 in which the NPTII coding sequence and its transcription terminator were removed and replaced with a CaMV 35S promoter-NPTII coding sequence-phaseolin terminator selectable marker. pJTS235 was constructed by ligating a 2.1-kb BamHI fragment of pJTS233 containing the NPTII coding sequence and phaseolin terminator into the BamHI fragment of pJTS222. The resulting plasmid, pJTS235 had the NPTII structural gene under the control of 35S promoter.

Example 2.4

Synthesis of Binary Vector pJTS250 pJTS250 was assembled as follows. A 353-bp PstI-BamHI fragment of pLG90 (provided by Dr. L. Gritz, Biogen, S. A., 46 Route des Acacias,-Geneva, Switzerland), which includes the entire hygromycin phosphotransferase gene (hph) coding region from the ATG translation start codon to 15 bp distal to the translation terminator, was ligated with the PstI-BamHI digest of pUC9 to produce pUC9+hph-a. Another aliquot of AvaI-digested pLG90 with AvaI flush ended. The 670-bp PstI fragment was cloned into the SmaI-PstI fragment of pUC9 to produce pUC9+hph-b, creating a 670-bp fragment PstI-EcoRI fragment. A 1.18-kb NaeI-BamHI fragment containing the phaseolin terminator (J. L. Slightom) was cloned into the BamHI-SmaI fragment of pUC9 to create pUC9+$T_{phas}$. The above three fragments (353-, 670- and 1180-bp) were ligated with the BamHI digest of pJTS222. The resulting binary plasmid, pJTS250, was produced comprised of a $P_{35S}$-hph-$T_{phas}$ plant selectable marker, and the capability to transform plant tissue to hygromycin resistance via Agrobacterium-mediated gene transfer.

Example 2.5

Synthesis of Binary Vector pGA482Δ+HYG$^R$ pGA482Δ+HYG$^R$ was produced from the following plasmids: pGA470 (Dr. G. An); pJTS262, including the entire T-DNA of pGA470 and a broad host range replicon; pJTS222; pJTS250, a binary plasmid that includes HYG$^R$ constructed by ligation of four fragments, including 353-bp PstI-BamHI fragment encoding part of the hph coding region, 670-bp PstI fragment encoding the remainder of the hph coding region, 1180-bp NaeI-BamHI fragment constituting $T_{phas}$ and pJTS222 digested with BamHI; pUC19B2-$P_{nos}$; pUC19B2+hph-$T_{phas}$; $p_{nos}$-hph-$T_{phas}$ expression cassette; and pGA482G (Dr. G. An).

The pGA482Δ+HYG$^R$ was constructed as follows: SalI fragments of pGA470 were ligated into SalI-digested pBR322. The resulting construct, pJTS262, is comprised of the entire T-DNA of pGA470 (from right to left border) and a second fragment containing part of the broad host range replicon. The 345-bp BclI-BamHI fragment of the resulting plasmid, having the nopaline synthase promoter ($P_{nos}$) fused to the 5' 42-bp of nopaline synthase (14 N-terminal amino acids), was inserted into the BamHI site of pUC19B2, having the SmaI site of pUC19 converted to a BglII site. The resultant recombinant plasmid, pUC19B2+$P_{nos}$ had the $P_{nos}$ segment within the BamHI-BglII fragment.

A 2.2-kb BamHI fragment containing the hph coding region from bacterial transposon Tn5 and the phaseolin transcription terminator (hph-$T_{phas}$) was isolated from pJTS250. The 2.2-kb hph-$T_{phas}$ fragment was inserted into the BamHI site of pUC19B2. The pUC19B2-$P_{nos}$ was digested with BamHI and HindIII. pUC19B2+hph-$T_{phas}$ was partially digested with BamHI and completely with HindIII to produce a 2.2-kb fragment with BamHI-HindIII ends. The fragment was ligated with BamHI-HindIII digested pUC19B2-$P_{nos}$ plasmid. The resulting construct, a $P_{nos}$-hph-$T_{phas}$ expression cassette, pUC19B2+HYG$^R$, was partially digested with BamHI; a resulting 5.3-kb fragment was digested with BglII to produce a 2.6-kb fragment. Separately, HindIII-EcoRI-digested pGA482 was ligated with HindIII-EcoRI-digested pSL1180, lacking a mcs. The resulting construct was further restricted to delete 2.5-kb of the original T-DNA containing the mcs. This binary was digested with BglII and ligated with the BamHI-BglII-ended 2.6-kb $P_{nos}$-hph-$T_{phas}$ fragment to produce pGA482Δ+HYG$^R$.

EXAMPLE 3

Geminivirus DNA Insertion Into Expression Vector Constructs

Example 3.1

Synthesis of Wild-Type ToMoV-FL AC1 ORF

ToMoV was collected from infected tomato plants in Bradenton, Fla. and inoculated into *Nicotiana benthamiana* and tomato. DNA was isolated from infected plants and viral DNA was isolated by preparative agarose gels. Viral DNA was digested with BglII, inserted into BglII-digested pSP72 to produce a full-length A-component clone (Seq ID 17). Similarly, a full-length DNA-B clone was produced from viral DNA digested with BamHI and inserted into BamBI-digested pBluescript II KS+ (Seq ID 18). DNA of either clone inoculated into *N. benthamiana* produced symptoms similar to the original virus.

A dimer clone in which DNA-A was inserted as a direct, tandem duplicate into the cloning vector was made by removing the single insert from its original vector with BglII and reinserting it into BglII-digested pSP72. The ApaI fragment of the resulting plasmid comprising the cloned DNA-A was inserted into the ApaI site of pBluescript II KS+.

Example 3.3

Synthesis of ToMoV-AC1

Wild type AC1 sense ORF and antisense (as) ORF of Table 1A were constructed from the AC1 ORF (SEQ ID 1 and 2) and part of the intergenic region was amplified by PCR from ToMoV-infected *N. benthamiana* DNA using primers PFL-2549B (SEQ ID 9) (5'-GGATCCGAGTAACTCATCTGGAGTACC-3') and PFL-1108B (SEQ ID 10) (5'-GGATCCGGAAGTAGATGGAGCACCCGC-3'). The 1.1-kb PCR product was BamHI-digested and inserted into the BamHI site pBluescript II KS+ to produce pTFAC1.

Example 3.4

Synthesis of ToMoV-AC1dlm

For the production of the mutated ORF, the AC1 ORF and part of the intergenic region was PCR amplified from ToMoV-infected *N. benthamiana* DNA by PCR using primers PFL-2549H (SEQ ID 16) (5'-TATCAAAGCTTGAGTAACTCATCTGGAGTACC-3') and PFL-1108B (SEQ ID 10) (5'-TATCGGATCCGGAAGTAGATGGAGCACCCGC-3') to produce a HindIII site near the translation start codon and a BamHI site near the translation terminator codon. The HindIII-BamHI-digested product was ligated with HindIII-BamHI-digested pBluescript II KS+ in a sense orientation relative to the f1 origin of replication. Mutations were generated in the NTP binding motifs of AC1 of this clone.

Trans-dominant lethal mutants (dlm) of AC1 protein (SEQ ID 3 and 4) were created by Kunkel mutagenesis. The above pBluescript plasmid was transformed into CJ236 (Invitrogen Co.), a dut-, ung- strain, so that the amplified plasmid DNA contains uracil. Single-stranded DNA was produced by transfecting the above transformed cells with helper phage M13-K07. The complementary sense strand of the ssDNA was synthesized in vitro using deoxynucleotides, including dTTP, and two mutagenic primers: PFAC1-680c (SEQ ID 11) (5'-CAAGAACAGGGcAcACGATGTGGG-3') and PFAC1-781c (SEQ ID 12) (5'-GTATAACGTCATTaAatACATCGCACCGC-3'). The lower case letters indicate altered nucleotides. The product was treated with T4 DNA ligase and transformed into XL1 Blue *E. coli* (Stratagene) to amplify plasmids containing the mutations produced by the mutagenic primers, which resulted in the mutations 2(a), 3(b) and 3(c), described above.

Example 3.5

Synthesis of ToMoV-AC1dlm1

The 1.1-kb BamHI fragment of pTFAC1, containing wild type AC1 ORF, was inserted to the BamHI site of pRT101e to produce a sense (pRTAC1-S) construct. The AC1 triple mutant (AC1 dlm) ORF was removed as a 1.1-kb XhoI-BamHI fragment from its vector and inserted in the sense orientation into XhoI-BamHI-digested pRT101e to produce pRT101e+AC1dlm. Plasmids pRTAC1-S and pRT101e+AC1dlm were cleaved at the unique PmlI site. After an additional digestion with ScaI, 1.6- and 3.2-kb fragments were isolated from each digest. The 1.6-kb fragment from pRTAC1-S was ligated with the 3.2-kb fragment from pRT101e+AC1dlm to produce a construct comprising the sequence designated as ToMoV-AC1dlm1 (SEQ ID 5 and 6) in Table 1A, mutation 2a described above.

Example 3.6

Synthesis of ToMoV-AC1dlm23

Plasmids pRTAC1-S and pRT101e+AC1dlm were cleaved at the unique PmlI site. After an additional digestion with ScaI, 1.6- and 3.2-kb fragments were isolated from each digest. The 3.2-kb fragment from pRTAC1-S was ligated with the 1.6-kb fragment from pRT101e+AC1dlm to produce a construct comprising the sequence designated as ToMoV-AC1dlm23 (SEQ ID 7 and 8) in Table 1A, double mutations 3(b) and 3(c) described above.

Example 3.7

Synthesis of ToMoV-AC1-AC2-AC3

A construct containing the AC1-AC2-AC3 fragments was produced by ligating a BamHI-HindIII fragment of a binary plasmid comprised of a dimer of the full-length, infectious ToMoV A-component with BamHI-HindIII-digested pJTS222. The BamHI-HindIII fragment from this construct was inserted into BamHI-HindIII-digested pBluescript II KS+. A 1.24 kb BglII-SphI fragment of the resulting plasmid, containing the complete AC2 and AC3 coding sequences and the C-terminal two-thirds of the AC1 ORF (SEQ ID 15), was ligated into BglII-SphI-digested pSL1180. The resulting plasmid contained the ΔAC1-AC2-AC3 fragment from ToMoV-A.

EXAMPLE 4

TYLCV-IS-EG Wild Type and Mutant Sequences

Example 4.1

Synthesis of TYLCV-C1

Tomato leaves with TYLCV symptoms were collected in Fayoum, Giza and Ismailia, Egypt. They were grafted to Geneva 80 tomatoes and *N. benthamiana*. The tomatoes and tobacco developed symptoms typical of TYLCV. Infectious TYLCV (TYLCV-IS-EG1) DNA was isolated from the infected *N. benthamiana*. The C1 ORF of TYLCV-IS-EG1 (SEQ ID 19 and 20) was produced as a 1.1-kb fragment by PCR amplification of infected plant DNA. The primers used were pTYIRc4 (SEQ ID 21) (5'-GGCCATAGAGCTTTGAGGGATCC CGATTCATTTC-3') and PTYC2v1679 (SEQ ID 22) (5'-GGTAGTAT GAGGATCCACAGTCTAGGTCT-3'). After BamHI-digesting the PCR products, they were ligated with BamHI-digested pBluescript II KS+ to produce pEGAL1-AS1, which contained the C1 ORF, as TYLCV-C1.

Example 4.2

Synthesis of TYLCV-ΔC2as

A truncated C2 ORF (ΔC2) was produced as a 365 bp fragment by PCR amplification of TYLCV-IS-EG1-infected *N. benthamiana* DNA. The primers PTYC2v1499 (SEQ ID 32) (5'-ATTTGTGGATCCTGATTACCTTCCTGATG TTGTGG-3') and PTYC2c1814 (SEQ ID 35) (5'-AAACGGATCCTTGAAAAATTGGGC-3') were used. The primers were BamHI-digested and ligated into BamHI-digested pBluescript II KS+ to produce pTYC2-25-1, which contained the AC2 ORF in antisense orientation.

Example 4.3

Synthesis of TYLCV-V1

A truncated V1 ORF was produced as a 625-bp fragment by PCR amplification of TYLCV-IS-EG1 infected *N. benthamiana* DNA. The primers used were PTYAR1v466 (SEQ ID 33) (5'-TTAGGATCCTATATCTGTTGTAAGGGC-3') and PTYAR1c1046 (SEQ ID 34) (5'-TTAACTAATGCAGGATCCTACATTCCAGAGGGC-3').

The primers were BamHI-digested and ligated into BamHI-digested pBluescript II KS+ to produce pTYV1-6-1, which contains the V1 ORF.

Example 4.4

Synthesis of TYLCV-C1-ΔC2-ΔC3

A 1.3-kb fragment of the TYLCV-IS-EG1 genome from nt 1471 to nt 20 via nt 2787 (Navot et al 1991) was produced by PCR amplification of infected *N. benthamiana* DNA. The primers used were PTYIRc4 and PTYC2v1499. The primers were BamHI-digested and inserted into BamHI-digested pBluescript II KS+ to produce pTYEGC4.

Example 4.5

Synthesis of TYLCV ORF Mutations

A full-length infectious clone of TYLCV-IS-EG1 (pTYEG14) was created to serve as the basis for TYLCV ORF constructs and for agroinoculation (see below). DNA from a tomato infected with TYLCV-IS-EG1 was used as template in two PCR amplification reactions. The first used primers PTYC1c2196 (SEQ ID 37) (5'-AAATCTGCAGATGAACTAGAAGAGTGGG-3') and PTYV1v1164 (SEQ ID 36) (5'-GTACGAGAACCATACTGAAAACGCCT-3') to amplify a fragment. The PstI-SphI-digested fragment was ligated with PstI-SphI-digested pGEM-5zf+ (Promega) to produce plasmid pEGI1A.

The second amplification reaction employed primers PTYC1v2182 (SEQ ID 39) (5'-TAGGCCATGGCCGCGCAGCGGAATACACG-3') and PTYC3c1320 (SEQ ID 38) (5'-GGTTCTGCAGCAGAGCAGTTGATCATGTATrG-3'). The PstI-NcoI-digested fragment was ligated with PstI-NcoI-digested pGEM-5zf+ to produce pEGI1-7B.

To assemble the full-length virus, the PstI-NcoI fragment of pEGI1-7B was ligated with the PstI-NcoI fragment of pEGI1A to produce a construct comprising full-length 2.7-kb viral DNA. The full-length construct was tested for infectivity by biolistic delivery into tobacco cells and found to create symptoms identical to the original disease. This clone was called pTYEG14. Orientation of insertion with respect to the f1 origin of replication was confirmed by DNA sequencing.

Three mutant C1 ORFs were constructed, each having one or two base changes altering the amino acid specificity of one codon by Kunkel mutagenesis using the plasmid representing the full-length infectious clone of TYLCV-IS-EG1 (pTYEG14) as template. The mutagenic primers (all viral sense) were: PC1v2467 (SEQ ID 25) (5'-GTTTCCGTCTcgCTCCACGTAGG-3'); PC1v2101 (SEQ ID 28) (5'-GGCCCACATTGTTgCGCCTGTTCTGC-3'); and PC1v2000 (SEQ ID 31) (5'-GGGTCTACGTCTctAATGACGTTGTACC-3'). (Lower case letters indicate altered nucleotides.) The resulting DNA was treated with T4 DNA ligase and transformed into XLI Blue *E. coli* cells to produce the following constructs: pTYK$^{104}$R #1 (SEQ ID 23 and 24), mutation 1(c); pTYK$^{225}$A #4 (SEQ ID 26 and 27), mutation 2(b); and pTYD$^{259}$R #5 (SEQ ID 29 and 30), mutation 3(a), described above.

The three mutant C1 ORFs were cloned into pCRII (Invitrogen). The C1 ORF for each mutant was PCR amplified using primers PTYIRc4 (SEQ ID 21) (5'-GGCCATAGAGCTTTGAGGATCCCGATTCATTTC-3') and PTYCv1707 (SEQ ID 42) (5'-GGTAGTATGAGGATCCACAGTCTAGGTCT-3'). The amplified fragments were ligated with PCRII to produce: pC1K$^{104}$R #2, mutation 1(c); pC1K$^{225}$A #4, mutation 2(b); and pC1D259R #2, mutation 3(a), described above.

These three ORF in BamHI fragments of their respective vectors provided the mutant C1 ORFs for expression cassettes for Agrobacterium mediated transformation.

EXAMPLE 5

BGMV Constructions

Wild-type and mutated versions of BGMV C1 (replication protein) ORF have been prepared. The wild-type sequence (SEQ ID 43 and 44) was mutated by Kunkel mutagenesis. Mutations in BGMV-C1 disclosed here include:

| ORF | Mutant | SEQ ID | Mutagenic Primer |
| --- | --- | --- | --- |
| BGAC190 | control | 45 | 47 |
| BGAC221 | mutation 2(c) | 48 | 50 |
| BGAC228 | mutation 2(a) | 51 | 53 |
| BGAC262 | mutation 3(a) | 54 | 56 |

SEQ ID NOS. 45, 48, 51, and 54, refer to mutagenized BGMV-C1 ORF DNA sequences presented in the Sequence Listing. These encode protein sequences 46, 49, 52, and 55, respectively. The mutant sequences were derived from wild-type DNA by Kunkel mutagenesis with mutagenic primers 47, 50, 53, and 56, respectively.

A 1.8 Kb BamHI-XhoI fragment containing the 35S promoter transcriptionally fused to a mutated AC1 ORF from BGMV-GA followed by the nopaline synthase transcription terminator was removed from WRG2398 (Dr. D. R. Russell, Agracetus Corp., Middleton, Wis.). The AC1 coding sequence was mutated in vitro using Kunkel mutagenesis to produce double mutations 2(c) and 2(a). This fragment was ligated with pRT101e digested with the same enzymes and the ligation mix used to transform *E. coli* DHS cells. Some transformants yielded desired recombinant plasmids that had the entire expression cassette from WRG2398 inserted into PRT101e (pJTS364). The new expression cassette was removed as a 2.9-Kb fragment from one of the recombinant plasmids by partial digestion with HindIII. It was ligated with pJTS246Δ that has been digested with HindIII and treated with CIAP. After transformation of DH5 cells, one recombinant among the transformants was identified that had the expression cassette inserted in the binary vector. DNA of this binary vector was transformed into *A. tumefaciens* LBA4404 and one transformant containing the binary was called strain At$^{364}$.

Plasmid pJTS364 was digested with EcoRV to eliminate the duplicated 35S promoters (P$_{35S}$) and the cleaved DNA ligated. A fraction of the rejoined molecules have a deletion for the fragment between the EcoRV sites which contains the 35S enhancer (e$_{35S}$) from WRG2398 and P$_{35S}$ from pRT101e. The ligation mix was used to transform DH5 cells. Among the transformants, the desired deleted plasmid was found and called pJTS365. The 2.5-Kb expression cassette was removed and ligated with HindIII-digested, CIAP treated pJTS246Δ. The ligation mix was used to transform DH5 cells. Recombinant binary plasmids were identified among the transformants and one of these was used as a source of DNA which was transformed into *A. tumefaciens* LBA4404. The transformed agrobacterium having the recombinant binary was called At$^{365}$.

The listed BGMV ORF are installed into appropriate promoter vectors and then into binary plasmids for Agrobacterium-mediated transformation into Phaseolus plants. Additionally, expression vectors are delivered into plants by biolistic acceleration or other methods by which plants can be transformed. Regenerated transformed plants are evaluated for levels of transgene RNA accumulation by RNA blot analysis to verify activity of the transgene. Subsequently, progeny are evaluated for ability to resist BGMV infection.

EXAMPLE 6

Expression Cassettes and Agrobacterium Strains

The following ToMoV constructs were produced.

Example 6.1

RTSC and RTAC

The 1.1-kb BamHI fragment of pTFAC1, containing wild type AC1 ORF was inserted to the BamHI site of pRT101e. Antisense (pRTAC1-A) and sense (pRTAC1-S) constructs were produced. HindIII fragments of each plasmid were each inserted into the HindIII site of pJTS246Δ in the same transcriptional direction as the NPTII selectable marker. The binary vectors were transformed into LBA4404 to produce RTAC (antisense) and RTSC (sense).

Example 6.2

DHSC and DHAC

The wild type AC1 CRF was also inserted as a BamHI fragment into BamHI-digested pDH51 in both orientations creating pDHAC1-S (sense) and pDHAC1-AS (antisense). The expression cassette of each recombinant was removed with EcoRI and inserted into EcoRI-digested pJTS235. Recombinant binary plasmids were selected that had the expression cassette inserted such that the directions of transcription as the selectable marker. These binary plasmids were introduced into LBA4404 by transformation to produce DHSC (sense) and DHAC (antisense)

Example 6.3

RTSFS pRTAC1-S was digested with BglII and flush ended by filling out. The resulting plasmid, pRTAC1-SΔBglII, lacked a BglII site but retained a core 4-base Sau3A site. This mutation shifted the translation reading frame by adding four nucleotides thereby producing a translation stop codon, and truncating the polypeptide (SEQ ID 13 and 14). A 2.1-kb HindIII fragment of pRTAC1-SΔBglII, which contains the expression cassette, was inserted in both orientations into the HindIII site of pJTS246Δ, unidirectional or divergent respecting the sense of selectable marker. A plasmid having an unidirectional orientation was introduced into LBA4404 by transformation to produce RTSFS.

Example 6.4

RT3AA

The 1.24-kb BglII-KpnI fragment of pSL1180+ΔAC1-AC2-AC3 was ligated into BglII-KpnI-digested pRTAC1-A to produce, pRT3AA, a pRT101e-like construct with the AC1, AC2 and AC3 ORFs inserted in antisense orientation. The 2.7 kb HindIII fragment of the pRT3AA was inserted into the HindIII site of pJTS246Δ in unidirectional orientation. The construct was introduced into LBA4404 by transformation to produce RT3AA.

Example 6.5

LASD and LASU

The 600-bp EcoRI-HincII fragment of pSL1180+PLAT52 was ligated with EcoRI-HincII-digested pRTAC1-S to replace the 800-bp 35S EcoRI-HincII promoter fragment by the 600-bp LAT52 EcoRI-HincII promoter fragment. After linearizing the plasmid with NcoI, the ATG start codon was destroyed by mung bean nuclease. The resulting plasmid contained an EcoRI and HindIII, but lacked a NcoI site. Accordingly, the sequences flanking the mutated NcoI site were the same as in the original LAT52 promoter untranslated 5' leader. The 5' untransformed leader was lengthened to 181 bp and included 68% k A/T nucleotides. HindIII cut plasmid fragment containing the expression cassette was inserted into the HindIII site of pJTS246Δ in both unidirectional and divergent orientations respecting the sense of the selectable marker. One binary of each type was transformed into LBA4404 creating strains LASU and LASD, respectively.

Example 6.6

MEU and MEU2

The AC1 triple mutant (dlmAC1) ORF was removed as a 1.1-kb Xho I-BamHI fragment from its vector and inserted in the sense orientation into Xho I-Bam HI-digested pRT101e. A 2.1-kb expression cassette thus created was removed from pRT101e+AC1dlm by incompletely digesting the recombinant vector with HindIII and isolating a 2.1-kb fragment. This fragment was inserted into the HindIII site of pJTS246Δ to produce a mutated enhanced unidirectional (MEU) vector. A second binary involving the same expression cassette which was tandemly duplicated in the unidirectional orientation was called MEU2. Both of the above binary vectors were transformed into LBA4404 to produce MEU and MEU2, respectively.

Example 6.7

MUA and MUB

ToMoV-AC1dlm1 was partially digested with HindIII and the 2.1-kb expression cassette was isolated. ToMoV-AC1dlm23 was completely digested with HindIII and the 2.1-kb cassette isolated. Each cassette was inserted into the HindIII site of pJTS246Δ. The recombinants were transformed into LBA4404 creating the Agrobacterium strains MUA and MUB, respectively.

Example 6.8

MUAIN and MUBIN

The 1.2 kb XhoI-BamHI-fragment of pRT101e+AC1 dlm1 containing the AC1dlm1 ORF was ligated with the XhoI-BamHI-fragment of pRTIN+Geneblock in a sense orientation. This construct was incompletely digested with HindIII followed by complete digestion with ScaI to produce a 2.6-kb fragment comprising the expression cassette. They were ligated with HindIII-digested pJTS246Δ in a divergent orientation respecting the selectable marker. The resulting Agrobacterium strain was called MUAIN.

The 2.1 kb BamHI fragment of pRT101e+AC1dlm23, containing the AC1dlm23, was ligated with BamHI-digested OpRTIN+Geneblock plasmid in the sense orientation. This plasmid was digested with HindIII and ScaI producing a 2.6-kb expression cassette fragment which inserted into HindIII-digested pJTS246Δ in an unidirectional direction. Plasmid DNA from this clone was transformed into LBA4404 to produce MUBIN.

Example 6.9

CODLM

The 1.1 kb BamHI fragment containing the wild type AC1 ORF was inserted into the BamHI site of pΔ1CO35 in a sense orientation to produce pΔ1CO35+AC1S. The 4.5 kb ApaI-BglII fragment of pΔ1CO35+AC1S was restricted to delete a 475-bp comprising wild-type AC1 ORF and ligated to the ApaI-BglII fragment of pRT101e+AC1 dlm1 to replace the wild type internal fragment by the mutated fragment. The recombinant (pΔ1CO35+AC1 dlm) was incompletely digested with HindIII, the 2.4-kb fragment containing the expression cassette isolated and inserted into the HindIII site of pJTS246Δ in an unidirectional orientation. The plasmid was transformed into LBA4404 cells to produce CODLM.

EXAMPLE 7

Constructs Containing TYLCV-IS-EG1

Example 7.1

LCA

The 1.1 kb BamHI fragment of pEGAL1-AS1 containing the C1 ORF was inserted in the BamHI site of pRT101e in an antisense orientation to produce pRTLCA1-A. A 2.1 kb HindIII fragment of pRTLCA1-A was inserted into the HindIII of pJTS246Δ in the unidirectional (U) orientation with regard to directions of transcription. LBA4404 cells were transformed with the resulting plasmid to produce LCA.

Example 7.2

LCR'

A 350-bp BamHI fragment encoding part of the C2 ORF of TYLCV-IS-EG1 was removed from pTYC2-25-1 and ligated into the BamHI site of pRT101e. The resulting construct contained the truncated C2 ORF inserted in an antisense orientation with respect to $P_{35S}$. The 1.3-kb expression cassette removed by HindIII digestion was inserted into the HindIII site of pJTS246Δ. Plasmid DNA of the resulting recombinant was partially digested with HindIII and ligated with the C1 antisense expression cassette. The desired plasmid had one copy of each the expression cassette inserted such that the directions of transcription of all cassettes was unidirectional. DNA of this binary plasmid was transformed into LBA4404 to produce a strain, LCR', comprising the two-cassette recombinant binary plasmid.

Example 7.3

LCR"

A 620-bp BamHI fragment of pTYV1-6-1 encoding part of the V1 ORF of TYLCV-IS-EG1 was ligated into the BamHI site of pRT101e in an antisense orientation with respect to the 35S promoter. A HindIII fragment of the resulting plasmid was ligated into the HindIII site of pJTS246Δ in an unidirectional direction respecting the selectable marker. Plasmid DNA of this recombinant was transformed into LBA4404 to produce LCR".

Example 7.4

RT3CA

The 1.3 kb BamHI fragment of pTYEGC4 containing the C1+ΔC2+ΔC3C structure was inserted into the BamHI site of pRT101e in an antisense manner with respect to the direction of transcription of the 35S promoter. The 2.3-kb HindIII fragment of pTYEGC4 the resulting plasmid containing the expression cassette was inserted into the HindIII site of pJTS246Δ in an unidirectional transcription directions. LBA4404 transformed with this plasmid to produce strain RT3CA.

The 1.3 kb BamHI fragment of pTYEGC4 comprising C1+ΔC2+ΔC3 DNA was ligated into the BamHI site of pΔ1Co35 in an antisense orientation with respect to the Commelina yellow mottle virus promoter. The 2.8 kb HindIII fragment of the resulting plasmid containing the expression cassette was inserted into the HindIII site of pJTS246Δ in an unidirectional orientation respecting the selectable marker. Plasmid DNA transformed into LBA4404 produced CO3CA.

The mutated 1.2 kb fragments containing C1 ORF were removed from their pCRII vectors and directionally ligated into the EcoRV-HindIII fragment of $eP_{mas}$–mcs–$T_{phas}$.

The resulting constructs were digested with XhoI and NaeI. HindIII fragments of pGA482Δ+$HYG^R$ were flush ended by filling out, and digested with XhoI. The XhoI-NaeI expression cassettes were ligated into the binary vector that had an XhoI cohesive end and a blunt end to produce three constructs, $C^{104}$, $C^{225}$ and $C^{259}$. DNA of each of the constructs were transformed into LBA4404 to produce the strains LC104, LC225 and LC259 and into Agrobacterium strain EHA105 (Mogen International, N.V.) to produce strains EC104, EC225 and EC259.

Example 7.5

RT3CS

The 1.3 kb BamHI fragment of pTYEGC4 containing the C1+ΔC2+ΔC3C structure was inserted into the BamHI site of pRT101e in an sense manner with respect to the direction of transcription of the 35S promoter. The 2.3-kb HindIII fragment of pTYEGC4 the resulting plasmid containing the expression cassette was inserted into the HindIII site of pJTS246Δ in an unidirectional transcription directions. LBA4404 transformed with this plasmid to produce strain RT3CS.

EXAMPLE 8

Production of Transgenic Plants Containing Disclosed Constructions and Analysis of Transgene Expression Transgenic plant were produced by Agrobacterium-cocultivation procedures well known to those skilled in the art.

The media of compositions used are here defined, for 1 liter:

1/2X basal: 1/2X MS salts (Gibco), 10 g sucrose, 7 g agar, pH 5.8;

TCM: 1X MS salts, 30 g sucrose, 0.2 g $KH_2PO_4$, 1X N&N vitamins (Gibco), 0.1 mg 2,4-D, 0.05 mg kinetin, 20 mg acetosyringone, 7 g agar, pH 5.8

Z: 1X MS salts, 30 g sucrose, 1X N&N vitamins, 1 mg zeatin, 100 mg kanamycine sulfate, 500 mg carbenicillin, 7 g agar, pH 5.8;

TR1: 1X MS salts, 30 g sucrose, 1X N&N vitamins, 3 mg glycine, 0.17 g $NaH_2PO_4$.H2O, 40 mg acetosyringone, pH 5.8;

MK5: 1/2X MS salts, 10 g sucrose, 1X N&N vitamins, 3 mg glycine, 0.17 g $NaH_2PO_4$.H2O, 50 mg kanamycin sulfate, 500 mg carbenicillin, 7 g agar, pH 5.8;

C: 1X MS salts, 30 g sucrose, 1X N&N vitamins, 3 mg glycine, 0.8 g $NH_4NO_3$, 2 mg BAP, 0.5 mg IAA, 100 mg kanamycine sulfate, 250 mg carbenicillin, 7 g agar, pH 5.8.

Seeds were sterilized by briefly rinsing in 70% EtOH and then in a solution of 20% chlorox plus Tween-20. The seeds were dried in vacuo and then rinsed several times with sterile water. Washed seeds were transferred into ½X basal media and incubated in a Magenta box for about 7 days in 16 hour photoperiods daily.

Fully expanded cotyledons were cut aseptically under water. Two cuts were made at the end, and the tip of the cotyledon piece and the center piece was retained and used. A culture of Agrobacterium containing the appropriate binary plasmid was initiated 24 hours before co-cultivation. Bacteria in 4–5 ml of the culture were collected by centrifugation and resuspended in TR1-liquid media. The suspension was poured onto cut cotyledon pieces and incubated for about 25 min. The cotyledon pieces were placed on sterile filter papers and placed compactly on TCM medium. The plates were kept in the dark at room temperature for about 48 hours, after which they were placed on plates containing 1 Z medium. The plates were incubated in 16 hours light daily at about 24° C. for about 21 days.

Calli that formed on cotyledon pieces were transferred to fresh 1 Z plates and shoots were removed as they formed to ½-X MK-5 tubes for rooting. A 4-mm piece of leaf from the shoot was also placed on C medium for callus formation. Twelve to fourteen days after the plating on C medium, calli were scored as "−" or "+". About 60 to 70% of shoots with +callus root in MK5 media. Those that have +callus but did not root were trimmed off at the end and re-rooted on fresh MK5 tubes. About 80% of these will root on the second attempt.

Rooted shoots were removed to potting soil when a strong root system has developed, usually about 3 weeks after rooting. The plants were kept in a closed plastic bags for about 3 days, the bags were opened slowly after that to acclimatize the young plant. A 6- to 8-mm piece of leaf tissue was collected for the NPTII ELISA assay. The NPTII positive plants were transferred to the greenhouse for seed production. About 4 to 5 weeks in the greenhouse leaf tissues were collected for RNA isolation and Northern blots were done for these plants.

EXAMPLE 9

Analysis of Transgenic Plants

Transgene RNA expression in transgenic tomato lines was accomplished by estimating steady state transcription levels using Northern blot hybridization. The level of transgene expression was used to select lines for agroinoculation. Total RNA was isolated from leaves and stems of young plants and electrophoresed on agarose gels.

The appropriate ORF DNA probe was radio-labeled and hybridized to RNA blotted on paper. After washing the RNA was visualized by autoradiography on X-ray film.

The following Tables 2, 3, and 4 summarize results showing plants produced with geminivirus constructs described above. The following symbols are used:

No+ or No−, Northern blot positive or negative;

So+ or So−, Southern blot positive or negative; *, no data;

$R_0$ and $R_1$, primary and progeny lines.

Table 2 summarizes the transgenic tomato plants produced by transfer of wildtype ToMoV ORF DNA into the plant by Agrobacterium infection. For example, several tomato plants (TGM-1 to -17, -20, -24, -28, -29, -33 to -41, -47 to -49, -53, -54, -59 to -67, -70 to -131; TTGV92-1 to -5, -10, -13 to -20) were produced by Agrobacterium containing the RTAC construct. As shown in Table 1A, this construct is comprised of the ToMoV AC1 OFR in an antisense configuration. The predominant characteristic of these RTAC-containing plants is the presence of ToMoV DNA in the plant tissue (i.e., So+), transcribed RNA (i.e., No+), and transmitted these traits to their progeny ($R_1$ RNA). Table 2 also described transgenic plants with DHAC and RT3AA constructs, comprised of ToMoV AC1 and AC1-AC2-AC3 antisense ORF, respectively (Table 1A).

Table 3 describes transgenic tomato plant containing mutant ToMoV ORF. These include the meu, meu2, Codlm, mub, mua, mubin, mauin, rtsfs, lasu, and lasd constructs described in Table 1A.

Table 4 describes transgenic tomato plant containing TYLCV ORF. These include LCA, LCR, RT3CA, RT3CS and Co3CA constructs of Table 1A, comprising TYLCV C1, C2 and C3 ORF.

These results establish that the methods described herein produce transgenic plants using DNA constructs containing gemini virus ORF.

TABLE 2

TOMATO PLANTS TRANSFORMED with ToMoV

| Product | Gene | $R_0$ RNA | $R_1$ RNA | $R_0$ DNA |
|---|---|---|---|---|
| Tgm-1, 10, 12, 14, 20, 29, 39, 53, 54, 64, 66, 70, 71, 80, 81, 82, 127 | RTAC | No + | No + | So + |
| Tgm-3, 8, 13, 16, 17, 24, 28, 33, 34, 36, 40, 41, 47, 48, 49, 65, 114 | RTAC | * | * | So + |
| Tgm-35 | RTAC | * | * | So− |
| Tgm-59, 79, 102, 88, 116 | RTAC | No− | No− | So + |
| Tgm-67 | RTAC | No + | No− | So + |
| Tgm-84, 90, 93, 94, 97, 98, 99, 100, 101, 103, 106, 107, 108, 112, 113, 115, 117, 120, 121, 122, 123, 125, 129, 131 | RTAC | No + | * | So + |
| Tgm-18, 19, 26, 42, 55, 58, 68 | DHAC | * | * | So + |
| Tgm-23, 31, 44, 51 | DHAC | No + | No + | So + |
| Tgm-27 | DHAC | No− | No + | So + |
| 3AA-3, 7, 9, 12, 13, 18, 21, 22, 23, 26, 27, 30 | RT3AA | No + | * | * |
| 3AA-4, 11, 16 | RT3AA | No− | * | * |
| TTGV92-1 | RTAC | No + | No− | So + |
| TTGV92-2, 5, 15, 17 | RTAC | No− | * | So + |
| TTGV92-3, 13, 19 | RTAC | No− | * | So− |
| TTGV92-4, 20 | RTAC | No + | No + | So + |
| TTGV92-6, 20 | DHAC | No + | No + | So + |
| TTGV92-7 | DHAC | * | No + | So + |
| TTGV92-10 | RTAC | No + | No + | * |
| TTGV92-11 | DHAC | No + | * | So + |
| TTGV92-14 | RTAC | No− | * | |
| TTGV92-16 | RTAC | * | * | So− |

TABLE 3

TOMATO PLANTS TRANSFORMED WITH ToMoV REP ORF DOMINANT LETHAL MUTANT CONSTRUCTS

| Product | Construct | $R_0$ RNA | $R_1$ RNA |
|---|---|---|---|
| TTGV92-26, 28, 36 | meu2 | * | * |
| TTGV92-27 | meu2 | No− | * |

TABLE 3-continued

TOMATO PLANTS TRANSFORMED WITH ToMoV
REP ORF DOMINANT LETHAL MUTANT CONSTRUCTS

| Product | Construct | $R_0$ RNA | $R_1$ RNA |
|---|---|---|---|
| TTGV92-42 | meu2 | * | No + |
| DLM2, 39, 42, 46, 47, 48, 49, 51, 52, 55, 58, 60, 62, 64, 66, 68, 70, 72, 74, 76, 79, 80, 81, 82, 83, 85, 88, 89, 90, 91, 93, 95, 96, 97, 98, 99, 100, 101, 102, 104, 106, 107, 108, 109, 110, 112, 116, 117, 118, 119, 120, 122, 124, 126, 127, 130, 133, 135, 136, 137, 139, 144, 148, 149, 151, 180, 155, 159, 162, 167, 170, 172, 173, 177, 192, 198, 200, 201, 204, 206, 211, 215, 217, 219, 220 | meu | No + | * |
| DLM3, 5, 7, 9, 10, 12, 14, 15, 18, 21, 26, 30, 31 | meu | No + | No + |
| DLM16 | meu2 | No− | No− |
| DLM17, 29 | meu | * | * |
| DLM22 | meu | No− | No− |
| DLM24 | meu | No− | No− |
| DLM25 | meu2 | No + | No + |
| DLM27, 28 | meu | No− | No− |
| DLM32 | meu2 | No + | No + |
| DLM37, 38, 44, 57, 59, 61, 75, 115, 129, 131, 138, 150, 166, 174, 179, 189, 208 | meu | No− | * |
| DLM143 | meu | No− | * |
| CODLM2, 4, 5, 6, 8, 9, 10, 13, 14, 15, 16, 18, 21, 24, 26, 28 | Codlm | No + | * |
| CODLM3, 7, 19, 27 | Codlm | No− | * |
| MU-2, 3, 4, 5, 6, 7, 14, 15, 19, 20, 26, 27, 30, 31, 32, 33, 34, 36, 37 | mub | No + | * |
| MU-8, 9, 12, 16, 18, 22, 28, 39, 41 | mua | No + | * |
| MU-11 | mua | No− | * |
| MU-13, 47 | mub | No− | * |
| MUIN-3, 6, 7 | mubin | No + | * |
| MUIN-4, 5 | muain | No + | * |
| MUIN-8, 10, 11, 14, 17, 18 | mubin | * | * |
| MUIN-9, 15, 16, 19 | muain | * | * |
| RTSFS-1, 3, 4, 6, 9, 10 | rtsfs | No + | * |
| RTSFS-7, 8 | rtsfs | No− | * |
| LAS-1 | lasu | No + | * |
| LAS-6, 10 | lasd | No + | * |
| LAS-11 | lasd | No− | * |

TABLE 4

TRANSGENIC TOMATO PLANTS TRANSFORMED
WITH TYLCV GENE CONSTRUCTS

| Product | Construct | $R_0$ DNA | $R_0$ RNA | $R_1$ RNA |
|---|---|---|---|---|
| Lca-1, 2, 37, 39, 43 | lca | So− | * | * |
| Lca-5, 14, 21, 24, 29 | lca | So + | * | No + |
| Lca-6, 35, 36, 46 | lca | So + | * | * |
| Lca-8, 12, 18, 19, 20, 26, 28 | lca | So + | * | No− |
| Lca-25 | lca | * | * | No− |
| Lca-45 | lca | So + | No + | * |
| Lcr-1, 5, 6, 22 | lcr | So + | No + | * |
| Lcr-3, 4, 17, 18, 20, 24 | lcr | So− | No− | * |
| Lcr-12 | lcr | So− | No + | * |
| Lcr-16, 31 | lcr | So + | No− | * |
| Lcr-25 | lcr | So + | * | * |
| Lcr-26, 27, 29, 32 | lcr | So− | * | * |
| 3CA-2, 3, −4, −6, −12, −15, −17, −18, −19, −21, −22 | RT3CA | * | No + | * |
| CO3CA-1, −2, −4, −5, −7, −8, −9, −11, −12, −13, −14, −17, −18, −19 | Co3CA | * | No + | * |
| CO3CA-6, −10 | Co3CA | * | No− | * |
| RT3CS-1 | RT3CS | * | No− | * |

EXAMPLE 10

Viral Challenge of Transgenic Plants

Example 10.1

ToMoV Agroinoculation Vector

A 5.6-kb fragment composed of a dimer of full-length infectious DNA-A was ligated with BamHI-HindIII digested binary plasmid pJTS222 to produce construct comprising the ToMoV-A dimer. The resulting plasmid produced transformed LBA4404 cells, uses as the A-component in agroinoculation experiments.

A 6.9-kb XbaI fragment that includes a full length infectious clone of DNA-B and the complete pBluescript II KS+ plasmid was inserted into the XbaI site of pJTS222. The resulting plasmid produced transformed LBA4404 cells used as the B-component in agroinoculation experiments.

Example 10.2

TYLC-IS-EG1 Agroinoculation Vector

The full length TYLCV-IS-EG1 DNA from infectious clone pTYEG14 was removed from the plasmid by SphI digestion and inserted at high molar excess into the SphI site of pGEM5Zf+ (Promega). The resulting plasmid, pTYEG7, contained a dimer of infectious TYLCV-IS-EG1 DNA. The 6.7-kb fragment of ScaI-PstI fragment of pTYEG7 comprised the dimer and part of pGEMZAf+. The 1.9-kb PstI-ScaI fragment of pSL1180 was ligated with the 6.7-kb fragment from pTYEG to produce a 8.7-kb construct with a single BglII site.

The 7.0 kb ScaI-BamHI fragment of the resulting recombinant plasmid was ligated with HpaI-BamHI-digested pJTS222. A resulting construct was used to transform LBA4404 cells to produce AtLC1, which was used in the TYLCV agroinoculation experiments.

10.3 Agroinoculation Procedure $R_1$ plants from self pollinated $R_0$ primary regenerants were agroinoculated 3 weeks after sowing. For bipartite geminiviruses, agroinoculation involves delivery of greater-than-full-length (must contain 2 common regions) ToMoV DNA-A and DNA-B into the seedlings using Agrobacterium. A small amount of a mixture of two Agrobacterium strains each containing a binary vector having in its T-DNA a partial or full tandem duplication of infectious geminivirus DNA was injected into the plant. For monopartite geminiviruses, only one agrobacterial strain is required if it carries a binary vector comprising a full or partial duplication of a full length infectious DNA.

Overnight cultures of Agrobacteria were diluted, and injected into stems of one month old tomato seedlings. About 100 hours later, a second inoculation identical to the first is performed.

Detection of NPTII by ELISA was taken as an indicium of the presence of the transgene. Agroinoculation experiments, summarized in Tables 5 to 10, show an array of resistance phenotypes. The data show several transgenic tomatoes resistant to ToMoV infection, including DLM12, TTGV92-42, CODLM6, CODLM8, CODLM13, CODLM14, MUA9, MUB20, MUA8, MUA18, MUA29, and MUA41.

TABLE 5

ToMoV Agroinoculations - DLM Transgenics

| Line (Generation) | Days Part Inoculation observation | Fraction of symptom-free and virus-free plants | | | |
|---|---|---|---|---|---|
| | | NPTII positives | | NPTII negatives | |
| | | visual | blot | visual | blot |
| TTGV92-36 (R1) | 20 | 2/16 | 2/16 | 0/2 | 0/2 |
| TTGV92-42 (R1) | 20 | 9/11 | 8/11 | 3/7 | 3/7 |
| untransformed | 20 | * | * | 0/17 | 0/17 |
| DLM3 (R1) | 26 | * | 5/16 | * | 0/2 |
| DLM7 (R1) | 26 | * | 4/15 | * | 1/3 |
| DLM9 (R1) | 26 | * | 0/14 | * | 1/2 |
| DLM10 (R1) | 26 | * | 2/16 | * | 0/2 |
| DLM12 (R1) | 26 | * | 10/17 | * | 0/1 |
| untransformed | 26 | * | * | * | 0/20 |
| DLM12 (R1) | 23 | 8/11 | 6/11 | * | * |
| TTGV92-42-(R2) | 23 | * | * | 3/18 | 2/18 |
| TTGV92-42-(R2) | 23 | 6/13 | 4/13 | 0/5 | 0/5 |
| TTGV92-42 (R1) | 23 | 13/15 | 10/15 | 0/3 | 0/3 |
| untransformed | 23 | * | * | 1/24 | 1/24 |
| DLM12 (R1) | 21 | 12/20 | 13/20 | 1/5 | 1/5 |
| DLM14 (R1) | 21 | 6/18 | 4/18 | * | * |
| DLM15 (R1) | 21 | 0/14 | 0/14 | 0/4 | 0/4 |
| DLM27 (R1) | 21 | 0/15 | 0/15 | 0/3 | 0/3 |
| DLM28 (R1) | 21 | 1/16 | 1/16 | 0/1 | 0/1 |
| untransformed | 21 | * | * | 0/15 | 0/15 |
| DLM5 (R1) | 18 | 0/13 | 1/13 | 0/5 | 0/5 |
| DLM17 (R1) | 18 | 1/5 | 1/5 | 3/9 | 3/9 |
| DLM22 (R1) | 18 | 0/15 | 0/15 | 0/3 | 0/3 |
| DLM26 (R1) | 18 | 2/3 | 2/3 | 1/5 | 1/5 |
| DLM29 (R1) | 18 | 0/13 | 0/13 | 1/3 | 1/3 |

TABLE 5-continued

ToMoV Agroinoculations - DLM Transgenics

| Line (Generation) | Days Part Inoculation observation | Fraction of symptom-free and virus-free plants | | | |
|---|---|---|---|---|---|
| | | NPTII positives | | NPTII negatives | |
| | | visual | blot | visual | blot |
| DLM30 (R1) | 18 | 3/14 | 3/14 | 1/4 | 1/4 |
| DLM31 (R1) | 18 | 4/12 | 4/12 | 0/6 | 0/6 |
| TTGV92-42-17(R2) | 18 | 7/13 | 6/13 | 1/4 | 1/4 |
| TTGV92-42(R2) | 18 | 17/18 | 17/18 | * | * |
| untransformed | 18 | * | * | 0/20 | 0/20 |
| DLM16 (R1) | 18 | 0/13 | 0/13 | 0/5 | 0/5 |
| DLM18 (R1) | 18 | 2/16 | 2/16 | 0/2 | 0/2 |
| DLM21 (R1) | 18 | 0/18 | 0/18 | * | * |
| DLM24 (R1) | 18 | 1/11 | 1/11 | 0/7 | 0/7 |
| DLM25 (R1) | 18 | 7/16 | 6/16 | 0/2 | 0/2 |
| DLM32 (R1) | 18 | 1/16 | 1/16 | 0/2 | 0/2 |
| untransformed | 18 | * | * | 0/13 | 0/13 |
| DLM39 (R1) | 30 | 0/15 | 1/15 | 1/4 | 1/4 |
| DLM46 (R1) | 18 | 0/15 | 0/15 | 0/5 | 0/5 |
| DLM47 (R1) | 18 | 5/17 | 4/17 | 0/3 | 0/3 |
| DLM48 (R1) | 18 | 0/15 | 0/15 | 0/5 | 0/5 |
| DLM49 (R1) | 18 | 1/16 | 9/16 | 0/4 | 0/4 |
| DLM55 (R1) | 18 | 0/14 | 0/14 | 0/6 | 0/6 |
| DLM58 (R1) | 18 | 0/14 | 1/14 | 0/6 | 0/6 |
| untransformed | 30 | * | * | 0/9 | 0/9 |

TABLE 6

ToMoV Agroinoculations: 3AA Transgenics

| Line (Generation) | DPI observation | Fraction of symptom and virus free plants | | | |
|---|---|---|---|---|---|
| | | NPTII positives | | NPTII negatives | |
| | | visual | blot | visual | blot |
| 3AA3 (R1) | 25 | 1/14 | 1/14 | 0/6 | 0/6 |
| 3AA7 (R1) | 25 | 3/18 | 3/18 | 0/2 | 0/2 |
| 3AA9 (R1) | 25 | 1/19 | 1/19 | 0/1 | 0/1 |
| 3AA12 (R1) | 25 | 0/14 | 0/14 | 0/6 | 0/6 |
| 3AA13 (R1) | 25 | 1/4 | 0/4 | 0/4 | 0/4 |
| 3AA16 (R1) | 25 | 1/11 | 1/11 | 0/9 | 0/9 |
| 3AA18 (R1) | 25 | 0/4 | 0/4 | 2/20 | 2/20 |
| untransformed | 25 | * | * | 0/15 | 0/15 |
| 3AA13 (R1) | 22 | 2/19 | 2/19 | 0/1 | 0/1 |
| 3AA21 (R1) | 25 | 3/13 | 3/13 | 0/7 | 0/7 |
| 3AA22 (R1) | 22 | 6/16 | 9/16 | 0/4 | 0/4 |
| 3AA23 (R1) | 25 | 3/9 | 4/9 | 0/1 | 0/1 |
| 3AA26 (R1) | 25 | 0/16 | 0/16 | 0/4 | 0/4 |
| 3AA27 (R1) | 25 | 0/10 | 0/10 | 0/4 | 0/4 |
| 3AA30 (R1) | 25 | 2/18 | 5/18 | 0/2 | 0/2 |
| untransformed | 25 | * | * | 0/15 | 0/15 |

TABLE 7

ToMoV Agroinoculations: LAS Transgenics

| Line (Generation) | DPI observation | Fraction of symptom and virus free plants | | | |
|---|---|---|---|---|---|
| | | NPTII positives | | NPTII negatives | |
| | | visual | blot | visual | blot |
| LAS6 (R1) | 25 | 8/11 | 8/11 | 0/9 | 0/9 |
| LAS1 (R1) | 25 | 0/10 | 0/10 | 0/10 | 0/10 |
| LAS10 (R1) | 25 | 1/14 | 1/14 | 1/6 | 1/6 |
| LAS11 (R1) | 25 | * | * | 0/20 | 0/20 |
| untransformed | 25 | * | * | 0/14 | 0/14 |

TABLE 8

ToMoV Agroinoculations: CODLM Transgenics

| Line (Generation) | DPI observation | Fraction of symptom- and virus-free plants | | | |
|---|---|---|---|---|---|
| | | NPTII positives | | NPTII negatives | |
| | | visual | blot | visual | blot |
| CODLM2 (R1) | 20 | 0/14 | 0/14 | 0/6 | 0/6 |
| CODLM5 (R1) | " | 0/15 | 0/15 | 0/5 | 0/5 |
| CODLM6 (R1) | " | 9/14 | 3/14 | 0/6 | 0/6 |
| CODLM8 (R1) | " | 8/20 | 1/20 | No NPTII- plants | * |
| CODLM9 (R1) | " | 0/18 | 0/18 | 0/2 | 0/2 |
| CODLM10 (R1) | " | 0/17 | 0/17 | 0/3 | 0/3 |
| CODLM13 (R1) | " | 11/20 | 0/20 | No NPTII- plants | * |

TABLE 8-continued

ToMoV Agroinoculations: CODLM Transgenics

| Line | DPI | Fraction of symptom- and virus-free plants | | | |
|---|---|---|---|---|---|
| | | NPTII positives | | NPTII negatives | |
| (Generation) | observation | visual | blot | visual | blot |
| CODLM14 (R1) | " | 7/16 | 0/16 | 0/4 | 0/4 |
| untransformed | " | * | * | 1/9 | 1/9 |

TABLE 9

ToMoV Agroinoculations: MUA and MUB Transgenics

| Line | DPI | Fraction of symptom- and virus-free plants | | | |
|---|---|---|---|---|---|
| | | NPTII positives | | NPTII negatives | |
| (Generation) | observation | visual | blot | visual | blot |
| MUA9 | 22 | 8/14 | 10/14 | 0/6 | 0/6 |
| MUB20 | " | 10/20 | 1/20 | No NPTII⁻ | * |
| MUB37 | " | 1/14 | 0/14 | 0/6 | 0/6 |
| MUB3 | 20 | 0/14 | 0/14 | 0/6 | 0/6 |
| MUB5 | " | 1/7 | 0/17 | 0/3 | 0/3 |
| MUB7 | " | 1/18 | 1/18 | 0/2 | 0/2 |
| MUA8 | " | 6/6 | 5/6 | 0/14 | 0/14 |
| MUA12 | " | No NPTII⁺ | * | 0/20 | 0/20 |
| MUB14 | " | 2/15 | 1/15 | 0/5 | 0/5 |
| MUB15 | " | 5/20 | 3/20 | No NPTII⁻ | * |
| MUA16 | " | 5/14 | 4/14 | 0/6 | 0/6 |
| MUA18 | 22 | * | 6/6 | * | 0/14 |
| MUB19 | " | * | 1/11 | * | No NPTII⁻ |
| MUB26 | " | * | 0/15 | * | 0/5 |
| MUA22 | 21 | * | 11/11 | * | 0/9 |
| MUB33 | " | * | 0/15 | * | 0/5 |
| MUB30 | " | * | 4/12 | * | 0/8 |
| MUA28 | " | * | 12/12 | * | 0/7 |
| MUA41 | " | * | 6/9 | * | 0/11 |
| MUB36 | " | * | 1/15 | * | 0/5 |
| MUA39 | " | * | 5/14 | * | 4/6 |
| MUB31 | " | * | 2/16 | * | 0/4 |
| MUB34 | " | * | NO NPTII⁺ | * | 0/20 |
| MUB32 | " | * | 3/16 | * | 0/4 |
| untransformed | " | * | * | 0/10 | 0/10 |

TABLE 10

ToMoV Agroinoculations: RTFS Transgenics

| Line | DPI | Fraction of symptom- and virus-free plants | | | |
|---|---|---|---|---|---|
| | | NPTII positives | | NPTII negatives | |
| (Generation) | observation | visual | blot | visual | blot |
| RTFS1 | 20 | 5/12 | 2/12 | 0/8 | 0/8 |
| RTFS3 | " | 0/15 | 0/15 | 0/5 | 0/5 |
| RTFS4 | " | 5/16 | 1/16 | 0/4 | 0/4 |
| RTFS6 | " | 10/12 | 10/12 | 0/8 | 0/8 |
| RTFS9 | " | 5/13 | 3/13 | 0/7 | 0/7 |
| RTFS10 | " | No NPTII⁺ | * | 0/20 | 0/20 |
| untransformed | " | * | * | 0/10 | 0/10 |

Example 10.4

Squash Blot Assay of Geminivirus

Approximately 3 weeks after agroinoculation, visible symptoms were monitored and compared to untransformed tomato lines. At the same time, two samples per plant of leaf extract were applied to a hybridization membrane. This was done by squashing a leaf disc about ⅛ inch diameter on the membrane such that leaf sap thoroughly impregnated the membrane. After the membrane was treated to denature the DNA in the extract, it was hybridized according to the same protocol as used for Northern blots with a radioactive probe that would detect the DNA-B component of ToMoV or the C1 ORF of TYLCV. The presence of viral DNA in the plant sap could be detected by autoradiography.

The presence of viral DNA was highly correlated with appearance of symptoms, an indicia of susceptibility to infection. The virus-free phenotype was correlated with the presence of the marker in families of transgenic tomatoes segregating the NPTII marker.

FIG. 1 shows that expression of the ToMoV AC1dlm transgene is required for resistance to ToMoV infection mediated by agroinoculation. High expression is necessary but in itself does not ensure resistance.

Example 10.4

Viruliferous Whitefly Inoculations

Ten whiteflies carrying ToMoV were put on each eight-day old seedling. Twenty-five seedlings were used per family. In those families of seedlings which were not homozygous for the transgene, NPTII assays were correlated with squash blot results. Twenty-one to thirty-one days after inoculation, samples of each plant were taken for biochemical and molecular hybridization assays. The results are-summarized in Table 11. The Visual Rating gives the average of are plants, in which "0" is no symptoms and "4" is with most marked symptoms. The squash blot results give the fraction of the plants that were virus free.

abolished infectivity and replication. In the transient assay for trans-dominance interference, double mutations 1(a) and 1(c) showed trans-dominance interference (Table 12).

TABLE 11

Florida Greenhouse Whitefly ToMoV Inoculations

Fraction of symptom- and virus-free plants

| Line (Generation) | DPI observation | NPTII Positives Blot Blot | NPTII Negatives Blot Blot | Visual Ratings | Squash Blot Results |
| --- | --- | --- | --- | --- | --- |
| TGM44 (R2) | 21 | 7/20 | 0/6 | 2.2 | 13/26 |
| TGM44 (R2) | 21 | 6/17 | 0/9 | 1.6 | 10/26 |
| untransformed | 21 | * | 7/25 | 3.6 | 7/25 |
| DLM12 (R2) | 31 | 10/26 | * | 1.0 | 20/26 |
| DLM12 (R2) | 31 | 8/26 | * | 2.0 | 18/26 |
| untransformed | 31 | * | 1/19 | 3.7 | 3/19 |
| DLM12 (R2) | 31 | 8/20 | * | 0.8 | 8/20 |
| DLM14 (R2) | 31 | 3/11 | * | 1.7 | 3/11 |
| DLM14 (R2) | 31 | 9/23 | * | 3.0 | 12/23 |
| untransformed | 31 | * | 0/16 | 2.9 | 0/16 |
| TTGV92-42 (R2) | 32 | 7/21 | 1/5 | 2.5 | 23/26 |
| TTGV92-42 (R3) | 32 | 22/26 | * | 0 | 26/26 |
| untransf. | 32 | * | * | 3.8 | 6/15 |
| XPH5978 | 32 | * | 10/26 | 2.9 | No Data |
| XPH5979 | 32 | * | 7/26 | 2.7 | No Data |

EXAMPLE 11

Transdominance in Plant Cell Lines

A mutated form of AC1 protein of BGMV inhibits replication of DNA-A in a tobacco suspension cell system. To evaluate AC1 protein mutants for their potential to interfere with viral replication, a transient assay was used to detect trans-dominant interference activity of the mutant viral ORF. (Table 12 and FIG. 2.).

TABLE 12

Effects of BGMV AC1 Mutations on Replication and Transdominance

| Mutation | Replication | Trans-dominance |
| --- | --- | --- |
| WT AC1 | + | 0% |
| mutation 1(a) | − | 90% |
| mutation 1(c) | − | 90% |
| $I^{190}R$ | + | 0% |
| mutation 2(c) | + | 0%* |
| mutation 2(a) | − | 50–80% |
| mutation 3(a) | − | >95% |
| mutations 2(a) and (c) | − | 50–80% |

NT-1 cells were inoculated with wildtype DNA-A or a lethal mutant of DNA-A of BGMV-GA (ADM; double mutations 2(a) and (c) in combination with carrier DNA (PBS) or AC1 transexpression vectors containing mutated forms of AC1 ORF. Total DNA was harvested from the NT-1 tobacco cells at 72 hours after inoculation, electrophoresed in an agarose gel, blotted onto paper and probed with a radiolabeled DNA probe corresponding to the coat protein of BGMV-GA DNA-A. The results demonstrate that wildtype AC1 protein produced in trans can replicate a lethal AC1 mutant of DNA-A. More importantly, the results show that codon changes in the nicking motif of the AC1 ORF Additional experimental treatments included:

A+PBS: wildtype BGMV-DNA-A was introduced into NT-1 cells with PBS at DNA weight ratios of 1:100 and 5:95 wildtype:PBS;

A+TDM: BGMV-DNA-A was introduced into NT-1 cells with transexpression vector coding for double mutations 2(a) and 2(c) at ratios of 1:100 and 5:95;

A+TD$^{262}$R: BGMV-DNA-A was introduced with transexpression vector coding for mutation 3(a) at ratios of 1:100 and 5:95;

ADM+PBS: DNA-A containing double mutations 2(a) and 2(c) with PBS at 5:95;

ADM+TAC1: DNA-A containing double mutations 2(a) and 2(c) with transexpression vector coding for wild-type AC1 at a ratio of 5:95.

The transexpression vectors used in these experiments express AC1 in the proper context for replication.

FIG. 1 represents the results of these experiments. The mutations created in the 35S promoter driven AC1 ORF are listed in the first column. These ORF are used in trans with wild-type DNA-A of BGMV-GA to determine transdominance interference. Replication was tested in an NT-1 cell system. Replication is presented as the amount of reduction in replication in comparison to wild-type replication level. Trans-dominance was determined by engineering each mutation into a AC1 transexpression vectors which contained the AC1 ORF under control of the CaMV 35S promoter. Mutant AC1 expression vectors were coinoculated into NT-1 cells along with WT DNA-A and reductions in DNA-A replication were estimated from autoradiograms. Trans-dominance data are expressed as the observed reduction in DNA-A replication when co-inoculated with each AC1 mutant. Mutation 2(c) confers a temperature sensitive phenotype for replication, supporting replication at 23° C. but not at 28° C.

Replication was observed in inoculations with wildtype BGMV-DNA-A plus carrier DNA (A+PBS) (FIG. 1). No replication was observed in inoculations with a mutant of DNA-A containing double mutations 2(a) and 2(c) coinoculated with carrier DNA (ADM+PBS). Replication of double mutations 2(a) and 2(c) was, however, complemented by transexpression of wildtype AC1 in the transient expression vector (ADM+TAC1). Replication of BGMV-DNA-A in the presence of two different AC1 mutants, treatments A+TDM and A+TD$^{262}$R reduced replication of virus DNA-A compared to the A+PBS treatments. Accordingly, transexpression of AC1 mutants can inhibit replication of BGMV-DNA-A. Further lethal mutants of AC1 inhibit replication when expressed in trans to DNA-A.

The results show that non-lethal mutants do not exhibit detectable transdominant activity. While levels of trans-dominance varied among different AC1 mutants, only replication-lethal mutants exhibited transdominant interference. Levels of AC1 expression directly relate to levels of trans-dominance and replication (FIG. 1). Thus, AC1 expression, results in production of a protein that mediates the "trans"-effective suppression. That is, this protein likely binds to the CR region which mediates its suppressive effect by inhibiting the binding of the wildtype AC1 protein.

We claim:

1. A transgenic plant comprising chromosomal DNA, said plant containing mutated geminivirus DNA integrated into said chromosomal DNA, the mutated geminivirus DNA encoding a protein required for geminivirus replication, wherein the expression of said mutated geminivirus DNA confers to the plant enhanced resistance to geminivirus infection compared to a nontransformed plant and further wherein the mutated geminivirus DNA comprises at least one mutation in the region of an AC1 or C1 open reading frame encoding the amino acid sequence NviDDi when compared with wildtype geminivirus DNA.

2. A transgenic plant comprising chromosomal DNA, said plant containing mutated geminivirus DNA integrated into said chromosomal DNA, the mutated geminivirus DNA encoding a protein required for geminivirus replication, wherein the expression of said mutated geminivirus DNA confers to the plant enhanced resistance to geminivirus infection compared to a nontransformed plant and further wherein the mutated geminivirus DNA is a tomato mottle virus AC1 mutant comprising SEQ ID NO: 7.

3. A transgenic plant comprising chromosomal DNA, said plant containing mutated geminivirus DNA integrated into said chromosomal DNA, the mutated geminivirus DNA encoding a protein required for geminivirus replication, wherein the expression of said mutated geminivirus DNA confers to the plant enhanced resistance to geminivirus infection compared to a nontransformed plant and further wherein the mutated geminivirus DNA is a tomato yellow leaf curl virus C1 mutant comprising SEQ ID NO: 29.

4. A transgenic plant comprising chromosomal DNA, said plant containing mutated geminivirus DNA integrated into said chromosomal DNA, the mutated geminivirus DNA encoding a protein required for geminivirus replication, wherein the expression of said mutated geminivirus DNA confers to the plant enhanced resistance to geminivirus infection compared to a nontransformed plant and further wherein the mutated geminivirus DNA is a bean golden mosaic virus AC1 mutant comprising SEQ ID NO 54.

5. A transgenic plant comprising chromosomal DNA, said plant containing mutated geminivirus DNA integrated into said chromosomal DNA, the mutated geminivirus DNA encoding a protein required for geminivirus replication, wherein the expression of said mutated geminivirus DNA confers to the plant enhanced resistance to geminivirus infection compared to a nontransformed plant and further wherein the mutated geminivirus DNA is selected from the group consisting of SEQ ID NO: 13 and SEQ ID NO:23.

* * * * *